(12) United States Patent
Mousa

(10) Patent No.: US 9,572,831 B2
(45) Date of Patent: Feb. 21, 2017

(54) COMPOSITION AND METHOD FOR SULFATED NON-ANTICOAGULANT LOW MOLECULAR WEIGHT HEPARINS IN CANCER AND TUMOR METASTASIS

(71) Applicant: Shaker A. Mousa, Wynantskill, NY (US)

(72) Inventor: Shaker A. Mousa, Wynantskill, NY (US)

( * ) Notice: Subject to any disclaimer, the term of this patent is extended or adjusted under 35 U.S.C. 154(b) by 0 days.

(21) Appl. No.: 14/526,660

(22) Filed: Oct. 29, 2014

(65) Prior Publication Data

US 2015/0132399 A1 May 14, 2015

Related U.S. Application Data

(60) Provisional application No. 61/896,738, filed on Oct. 29, 2013, provisional application No. 61/896,770, filed on Oct. 29, 2013.

(51) Int. Cl.

| | | |
|---|---|---|
| *A61K 31/704* | (2006.01) | |
| *A61K 31/727* | (2006.01) | |
| *A61K 47/48* | (2006.01) | |
| *A61K 31/7068* | (2006.01) | |
| *A61K 33/24* | (2006.01) | |

(52) U.S. Cl.
CPC .......... *A61K 31/727* (2013.01); *A61K 31/704* (2013.01); *A61K 31/7068* (2013.01); *A61K 33/24* (2013.01); *A61K 47/482* (2013.01); *A61K 47/48215* (2013.01); *A61K 47/48869* (2013.01); *A61K 47/48907* (2013.01); *A61K 47/48915* (2013.01)

(58) Field of Classification Search
None
See application file for complete search history.

(56) References Cited

U.S. PATENT DOCUMENTS

| | | | | |
|---|---|---|---|---|
| 2009/0074828 A1* | 3/2009 | Alexis | ........... | A61K 9/5123 424/422 |
| 2009/0186093 A1* | 7/2009 | Liu | ........... | A61K 9/5026 424/497 |
| 2011/0189299 A1* | 8/2011 | Okubo | ........... | A61K 9/0043 424/491 |
| 2015/0140106 A1* | 5/2015 | Mousa | ........... | A61K 9/5146 424/493 |
| 2015/0150818 A1* | 6/2015 | Mousa | ........... | A61K 31/737 424/451 |

OTHER PUBLICATIONS

Chakravarthi et al., International Journal of Pharmaceutics, 2011, 409, 111-120.*
Phillips et al., Anticancer Research, 2011, 31, 411-420.*

* cited by examiner

*Primary Examiner* — Abigail Fisher
(74) *Attorney, Agent, or Firm* — Schmeiser, Olsen & Watts, LLP

(57) ABSTRACT

A nanoformulation that includes nanoparticles. Each nanoparticle includes a shell in which a glycosaminoglycan (GAG is encapsulated. The GAG is ionically or covalently bonded to the shell. The GAG is selected from the group consisting of sulfated non-anticoagulant heparin (SNACH), super-sulfated non-anticoagulant heparin (S-SNACH), and a combination thereof. The shell includes Poly (lactic-co-glycolic acid) (PLGA), Polyethylene Glycol (PEG)-PLGA, maleimide-PEG-PLGA, chitosan, chitosan-PLGA, methoxy-polyethyleneglycol-poly (lactide-co-glycolide) (MPEG-PLGA)-(maleimide-PEG-PLGA), PLGA-Polycaprolate, or calcium alginate. A method of using the nanoformulation to treat a cancer in a subject includes administering to the patient a therapeutically effective amount of the nanoformulation for treating the cancer.

18 Claims, 48 Drawing Sheets

Figure 1: Comparative inhibitory efficacy of colon cancer to P-selectin adhesion for S-NACH versus heparin, LMWHs or fondaparinux Figure 2: Morphologic characteristics of tumor cell adhesion and invasion in the vessel segment perfusion system

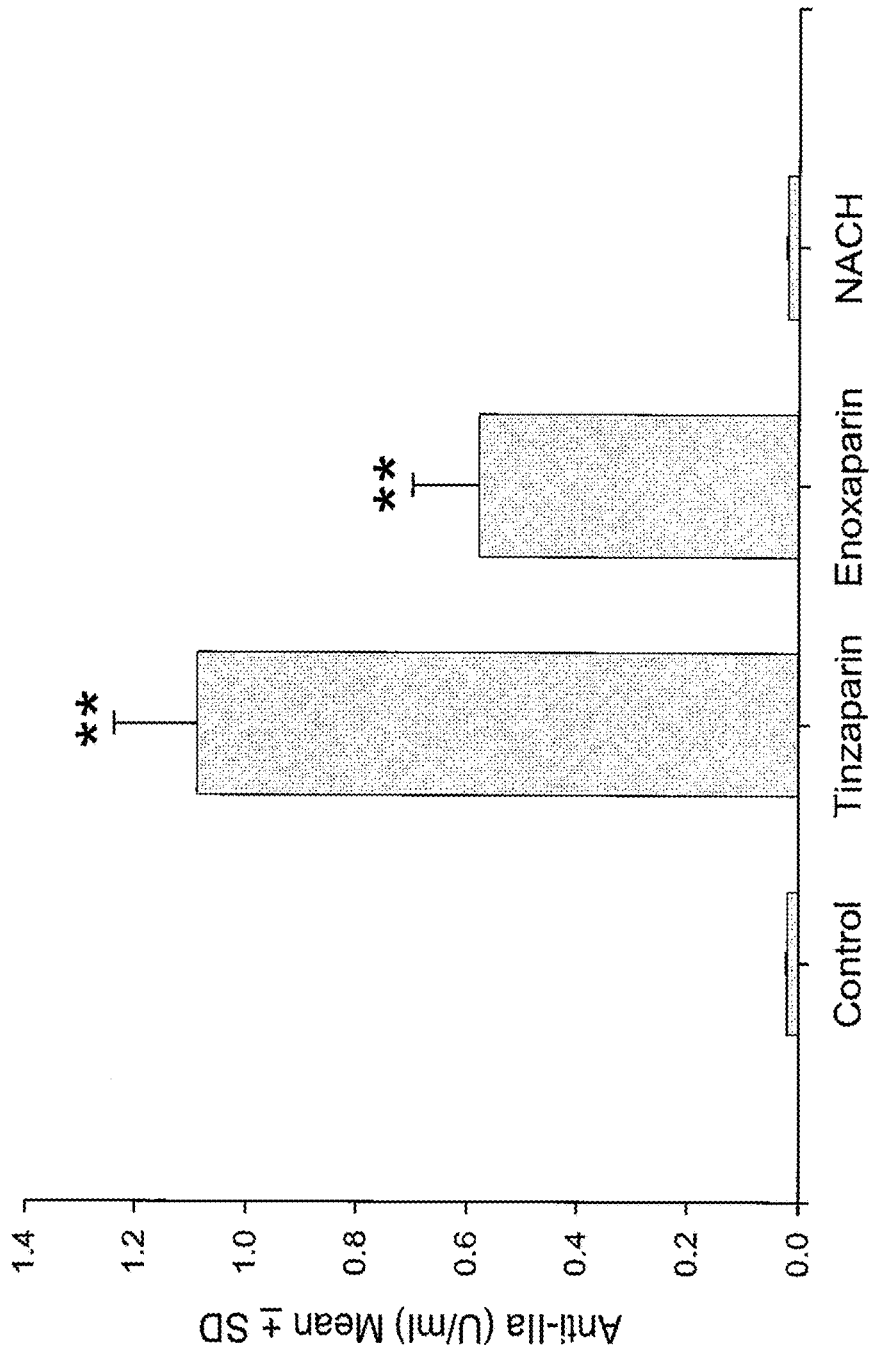

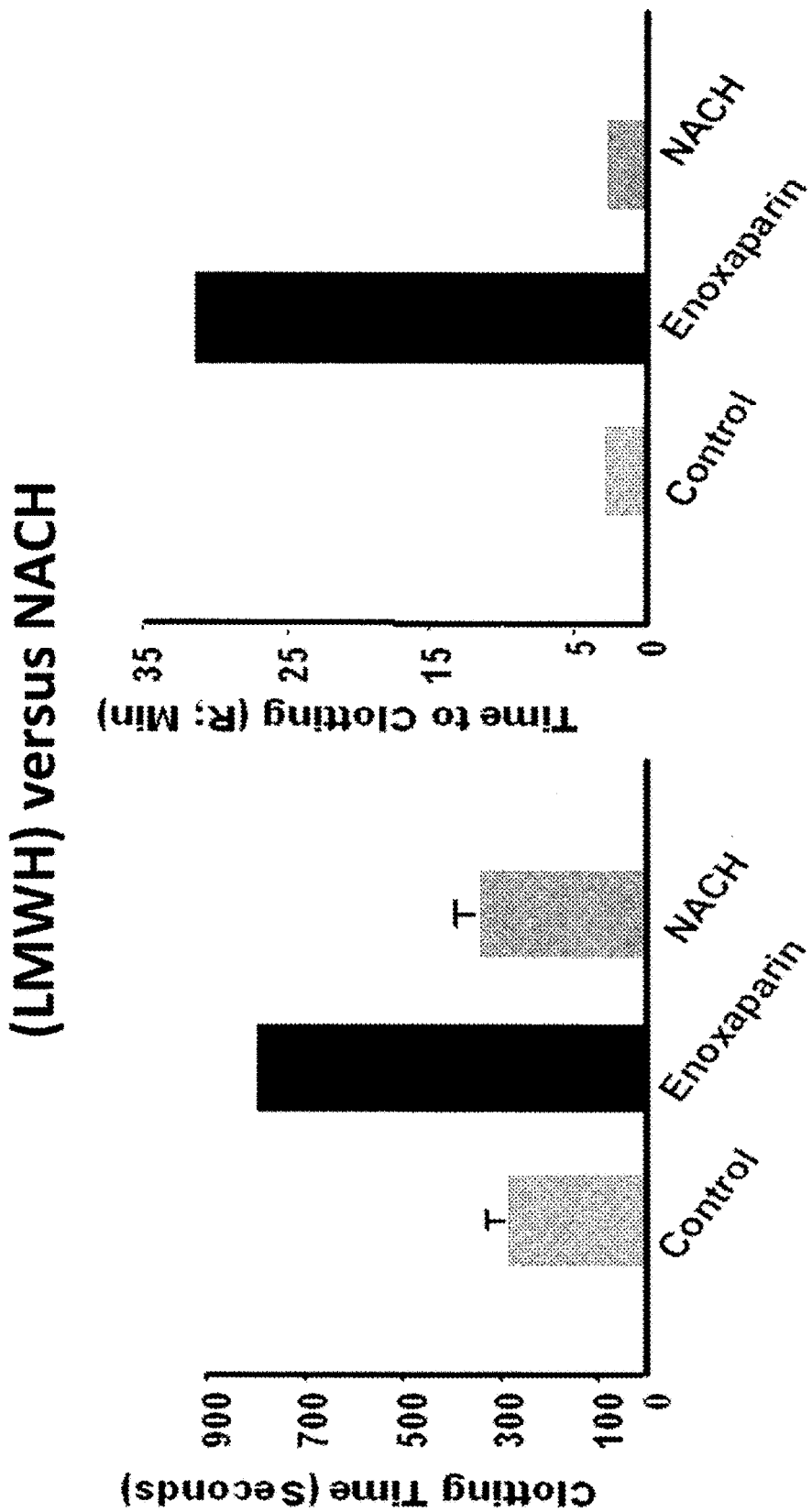
Figure 6: Coagulation analysis of heparins: Enoxaparin (LMWH) versus NACH

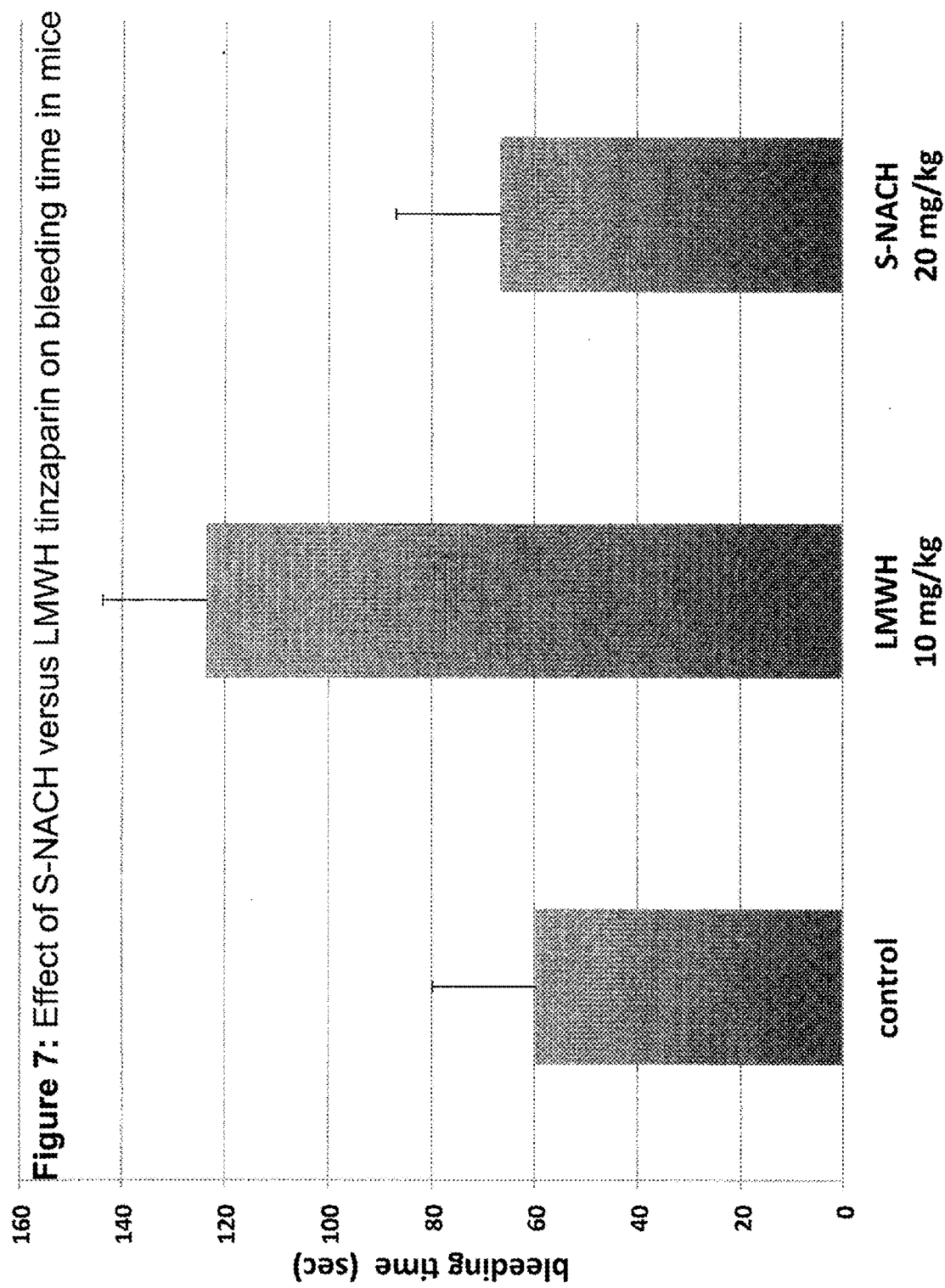

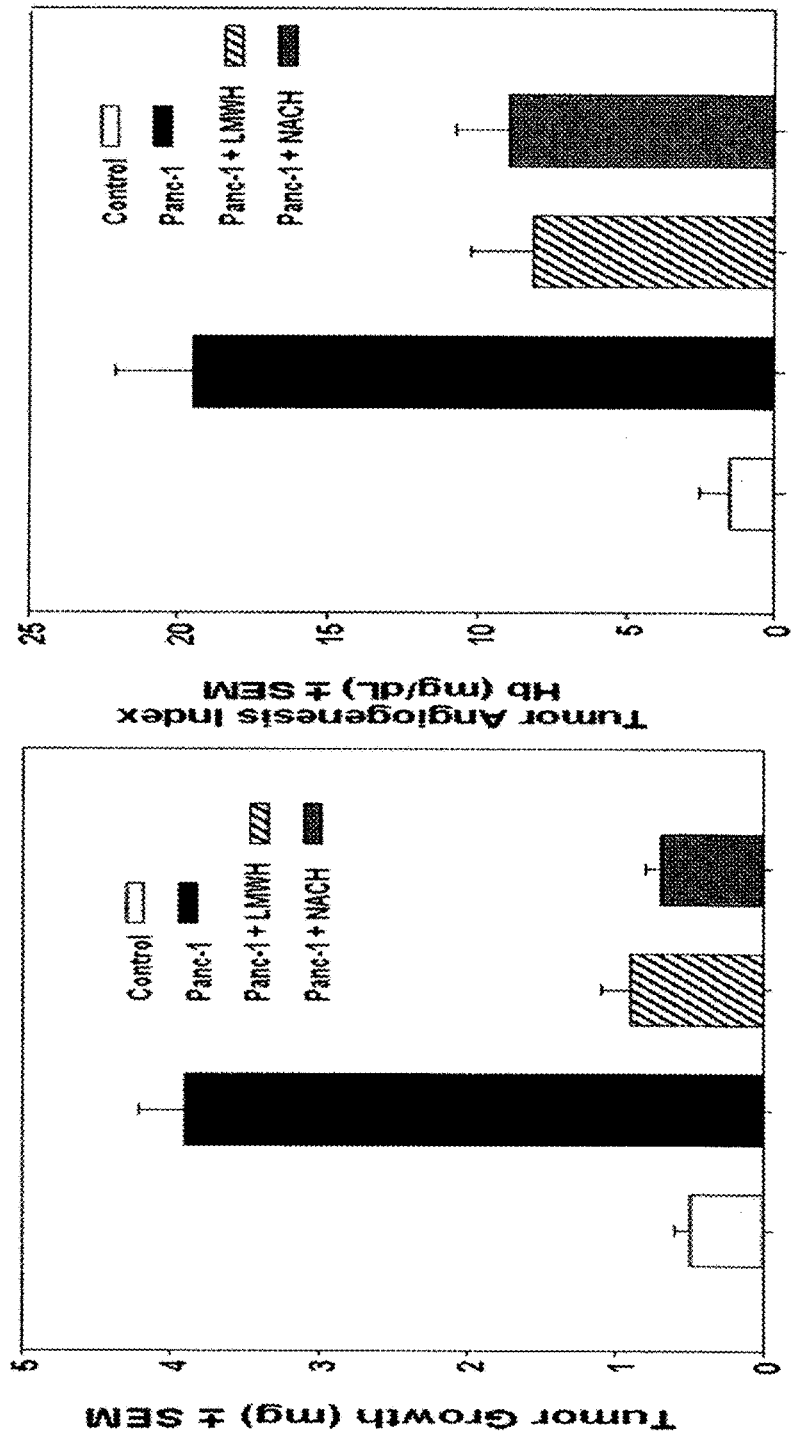
Figure 8: NACH or LMWH inhibit pancreatic tumor growth and angiogenesis in the Chick Chorioallantoic membrane (CAM)-tumor implant model

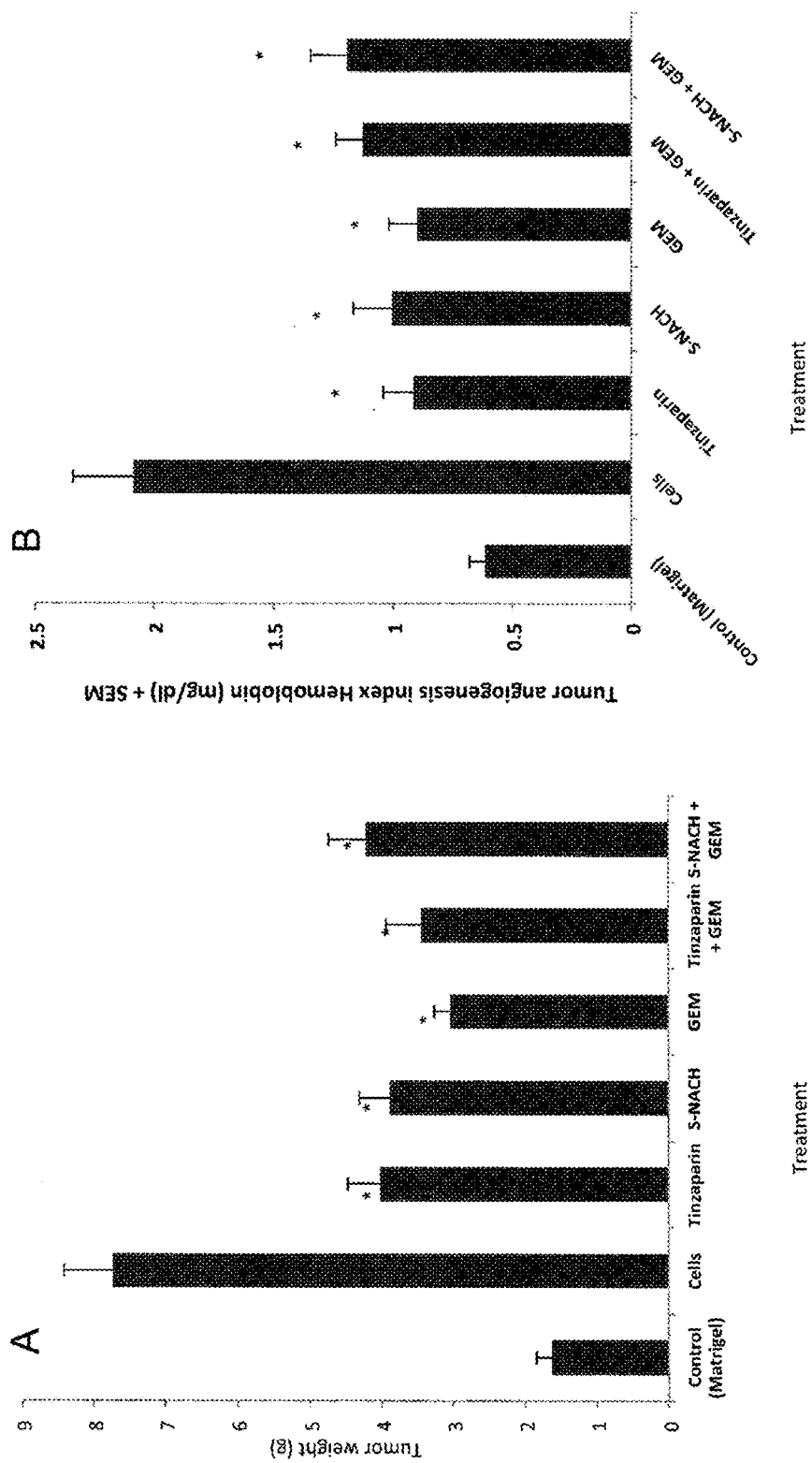
Figure 9: Effect of S-NACH versus the LMWH tinzaparin on pancreatic tumor growth and tumor angiogenesis in the CAM tumor implant model

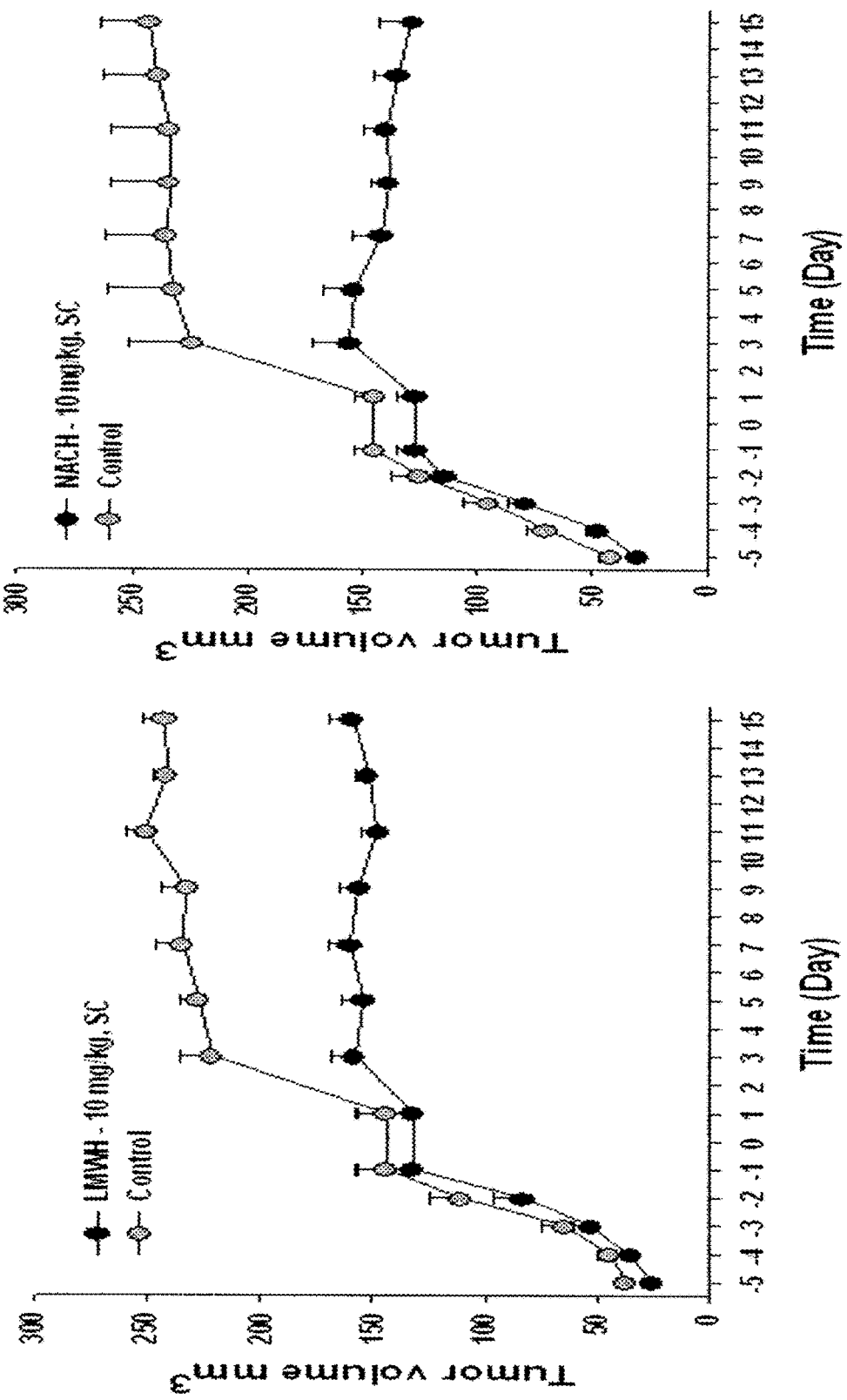
Figure 10: Effect of NACH versus LMWH tinzaparin on tumor growth of MCF7 Doxorubicin Resistant

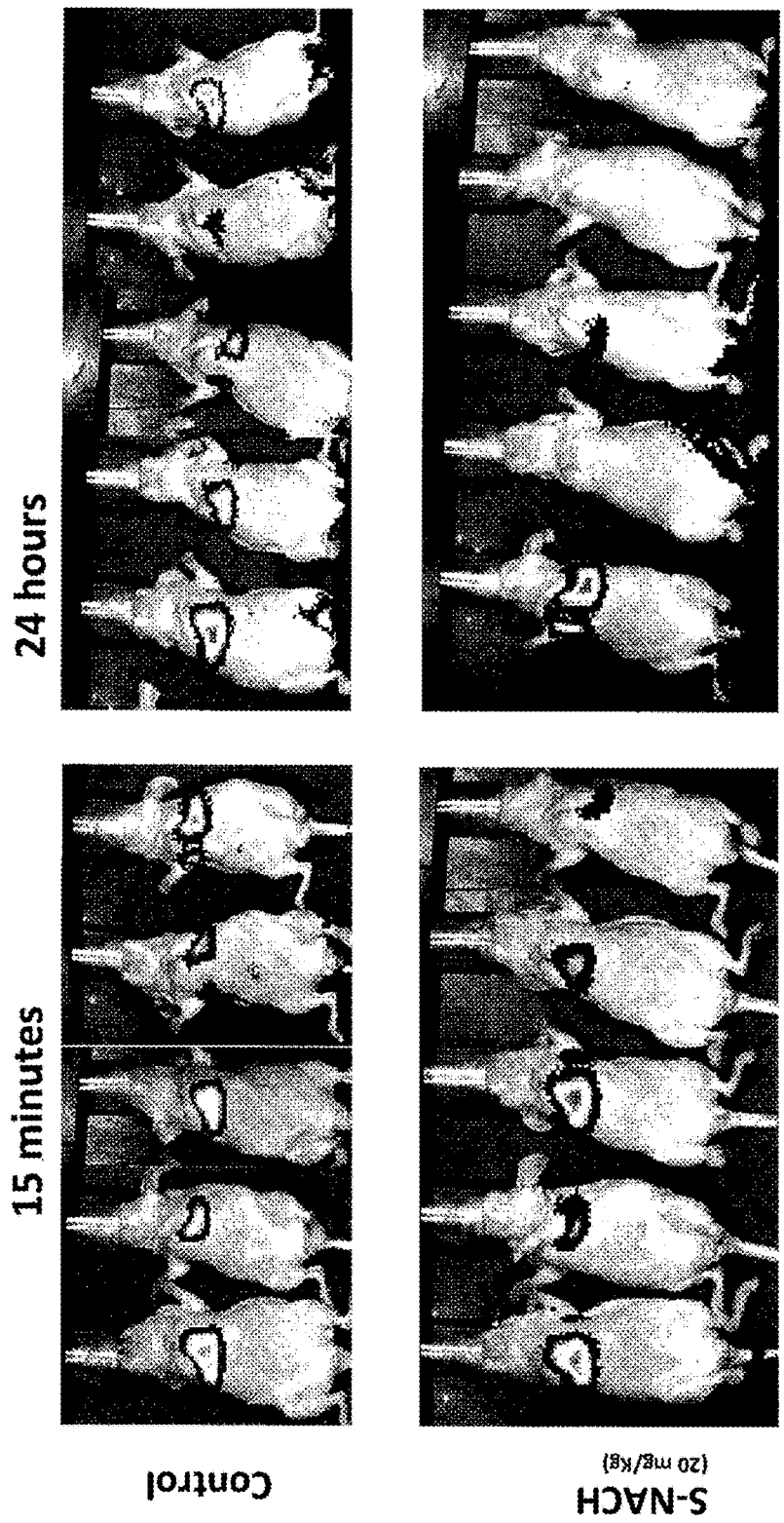
Figure 11: Effect of S-NACH on Pancreatic Cancer Growth 24 hours after Orthotopic implant in Nude Mice

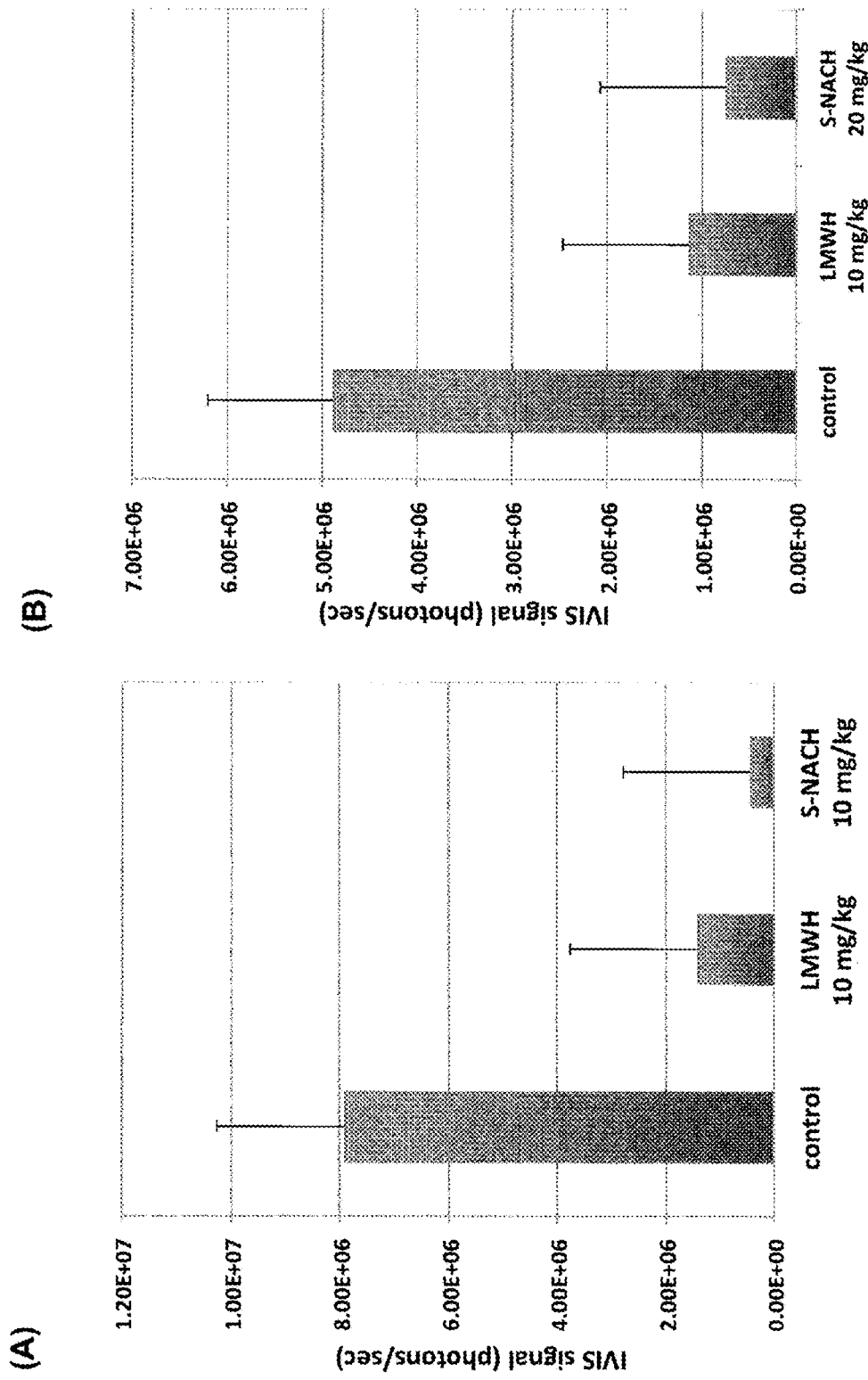
Figure 12: Effect of S-NACH versus the LMWH tinzaparin on the IVIS signal intensity of pancreatic tumor growth in nude mice

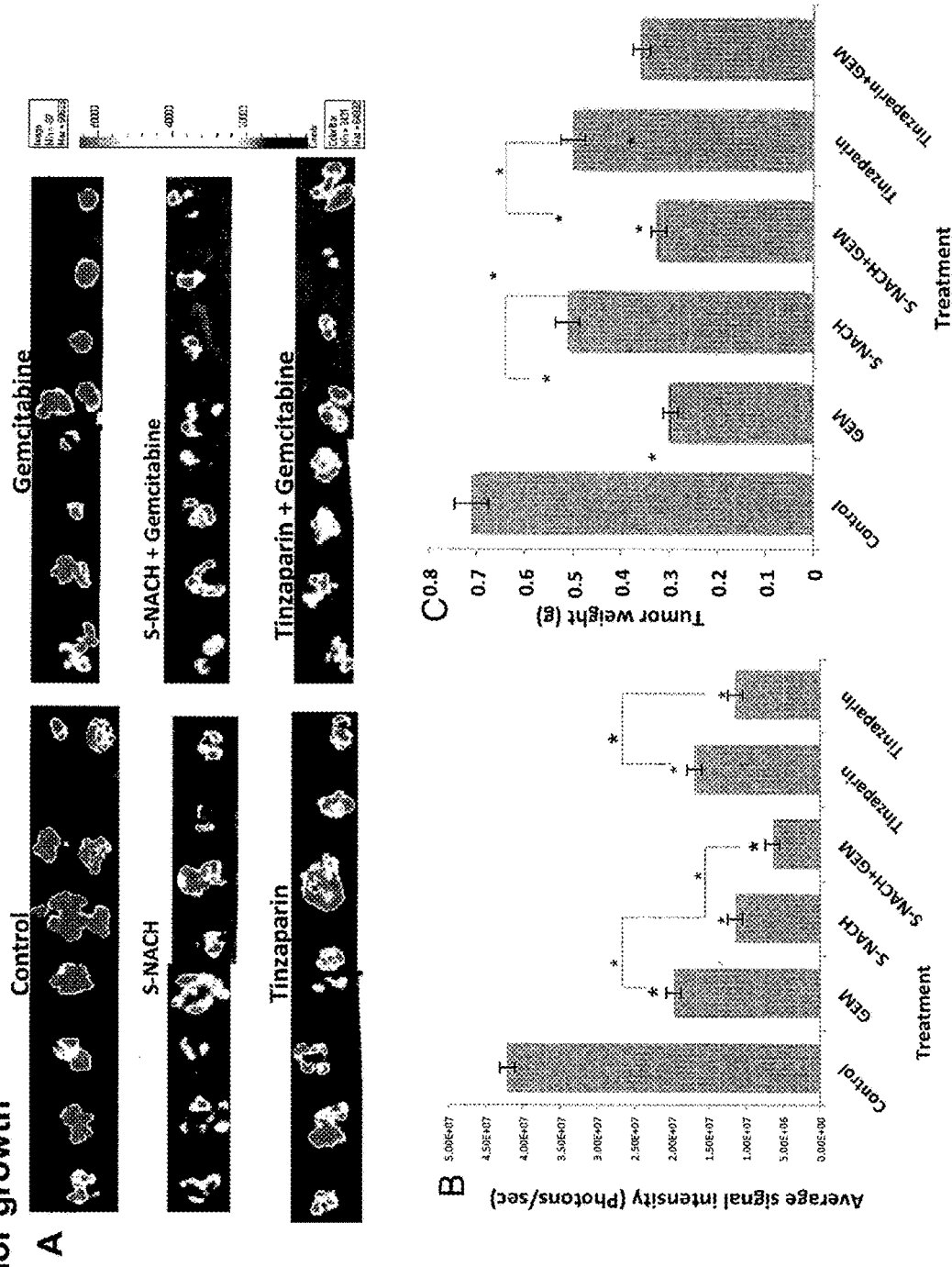
Figure 13: Effect of S-NACH versus Tinzaparin with or without on pancreatic tumor growth

Figure 14: Effect of S-NACH versus tinzaparin on pancreatic tumor necrosis
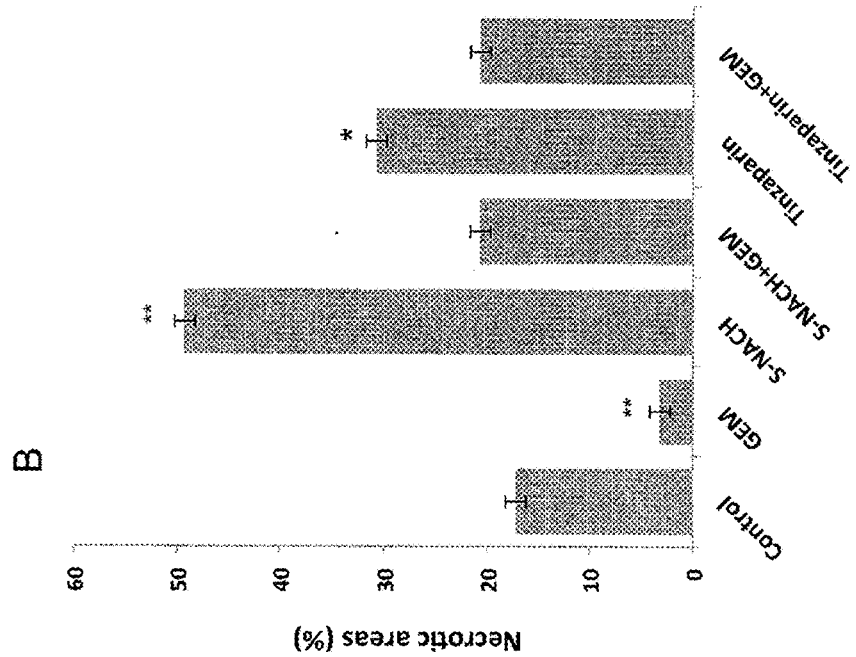
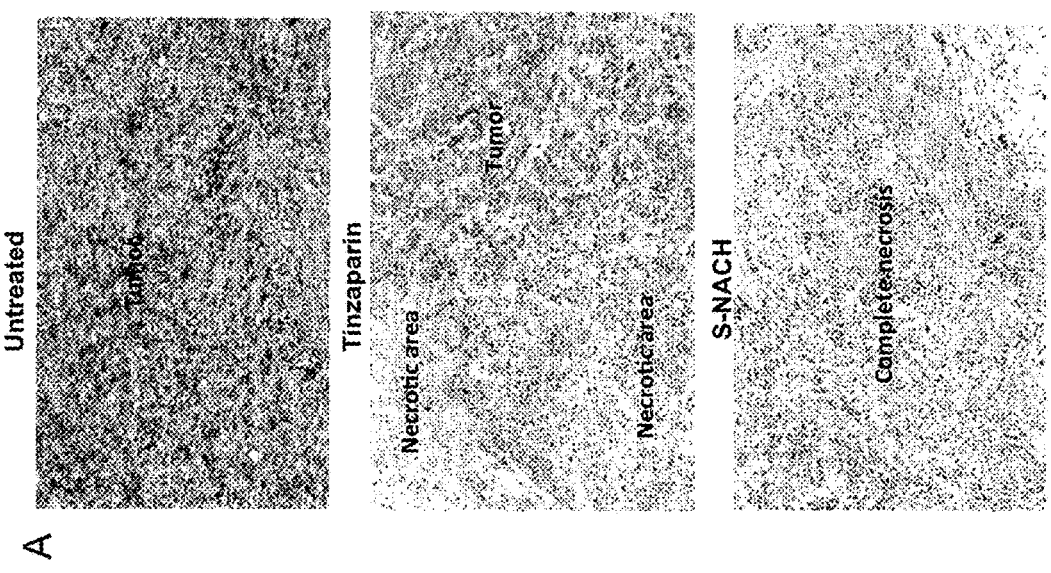

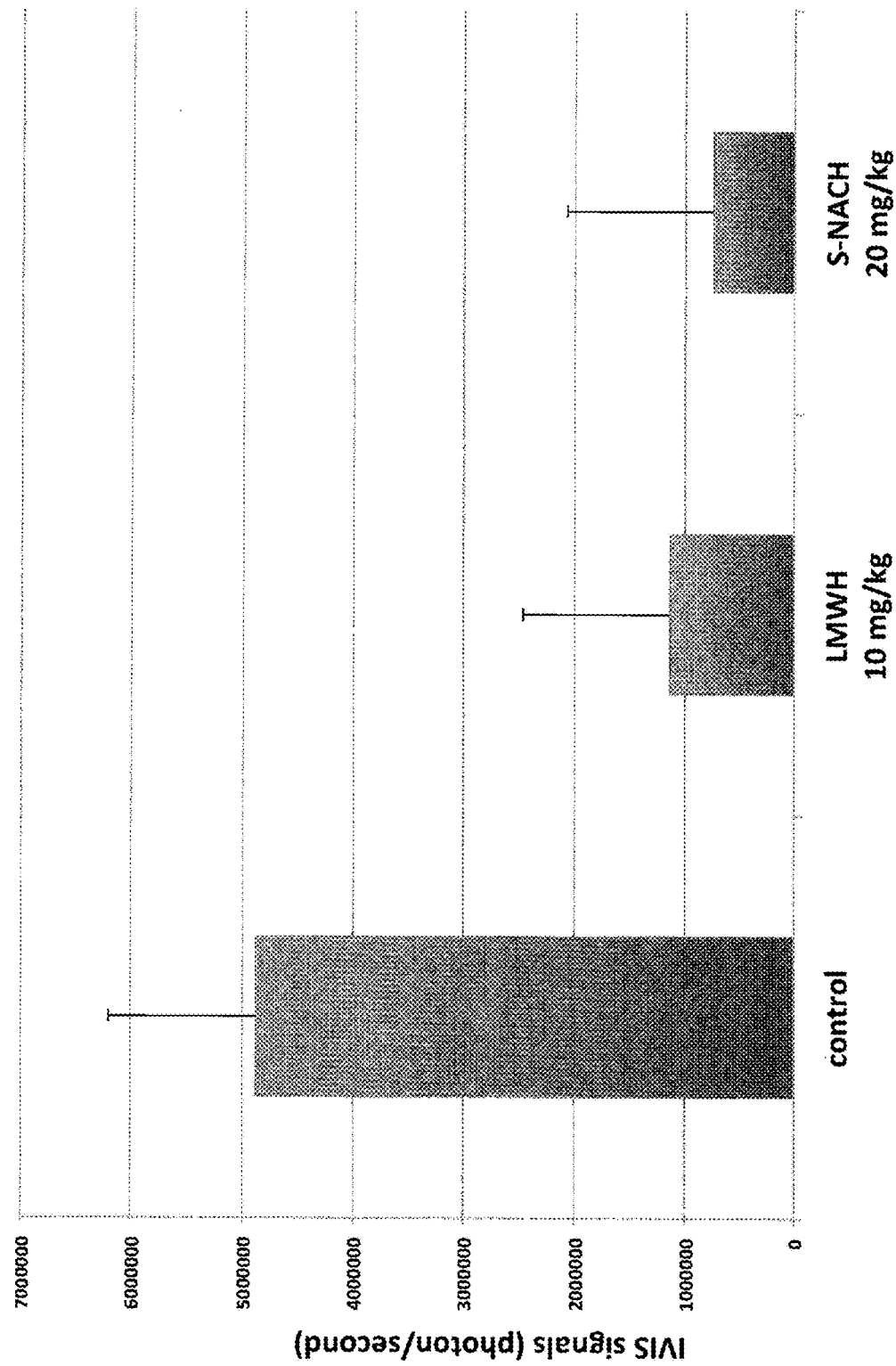

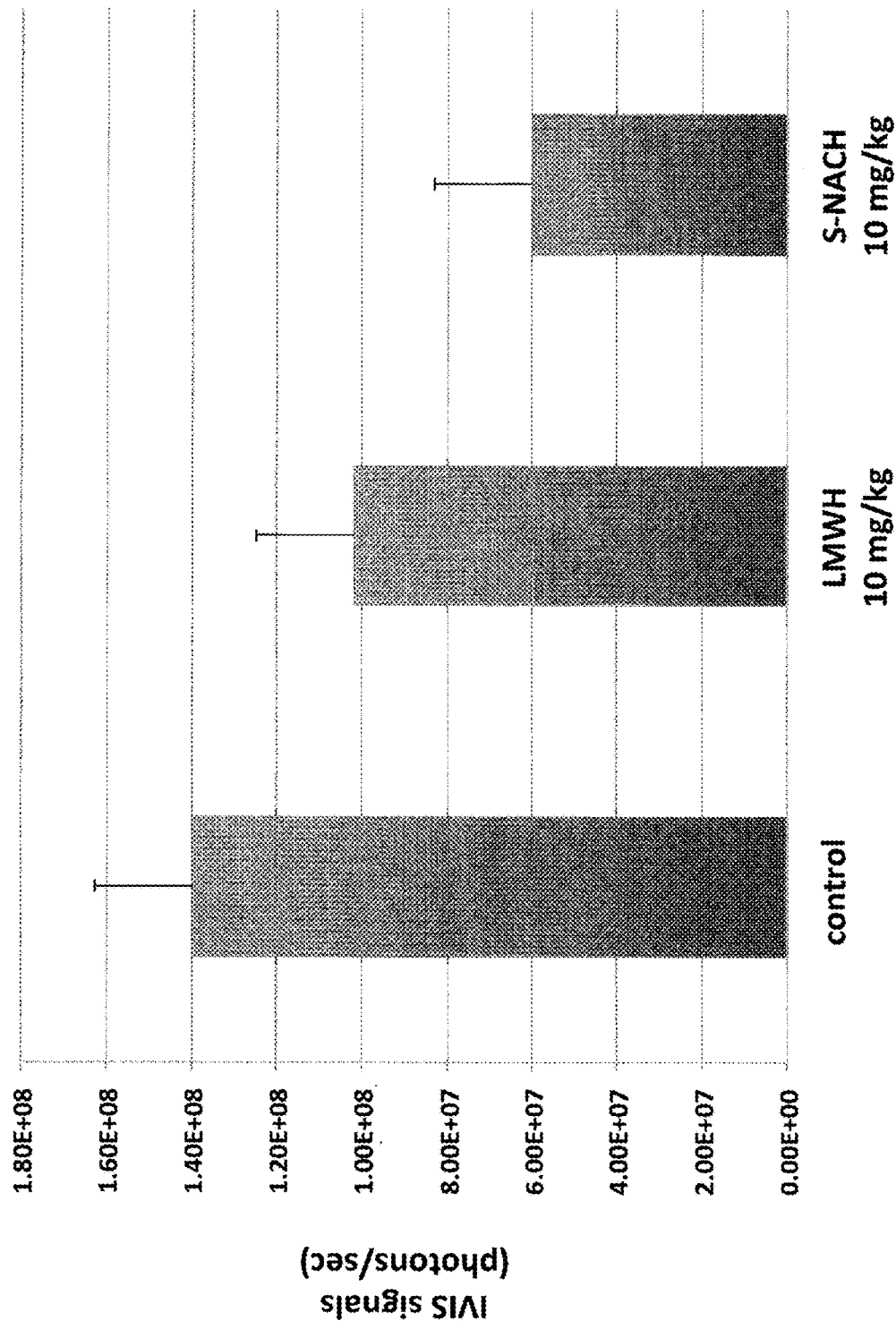
Figure 16: Comparing tumor relapse after surgical excision of pancreatic cancer

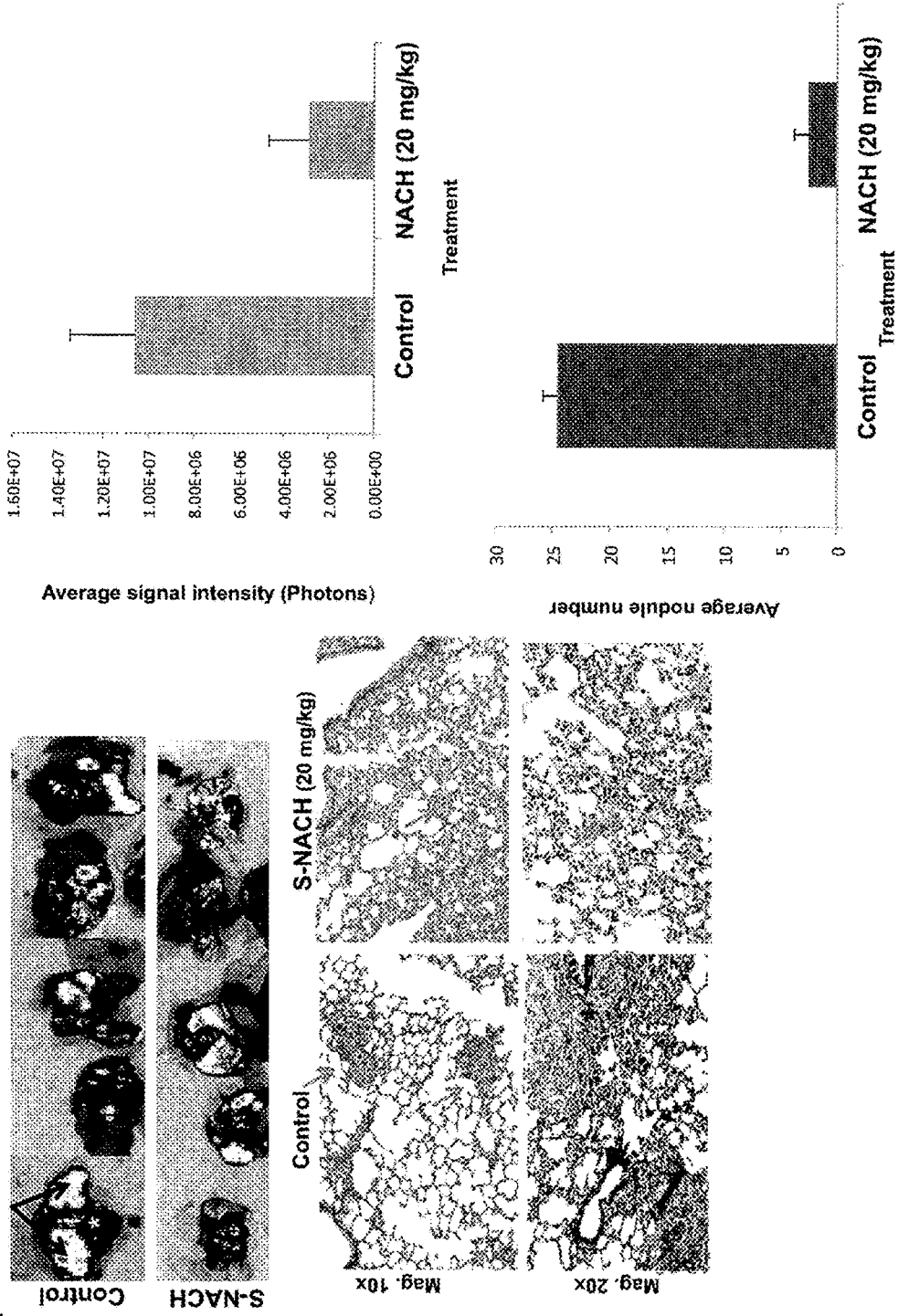
Figure 17: Anti-Metastatic Effect of S-NACH into the Lung of Nude Mice

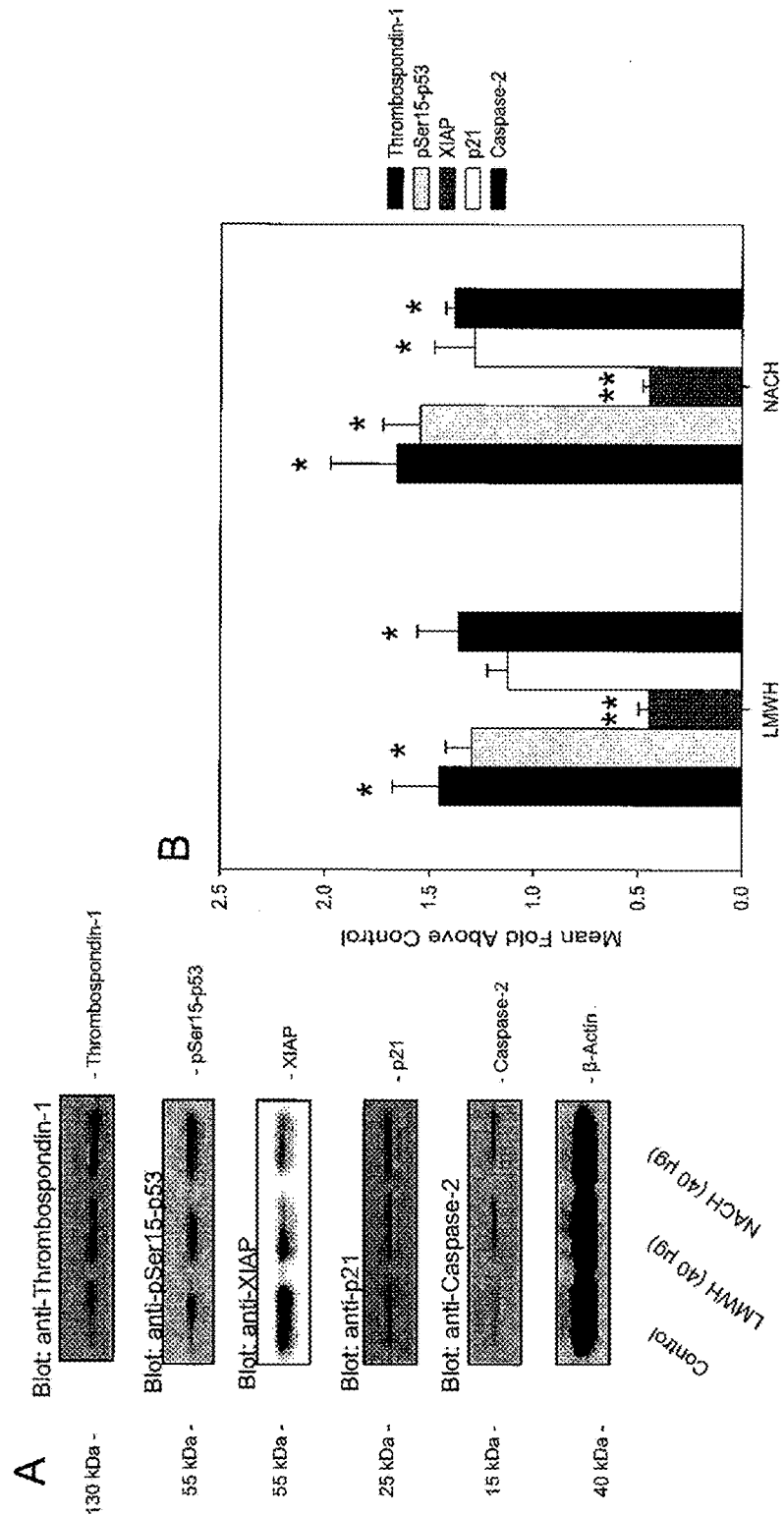
Figure 18: Molecular effects of NACH versus LMWH in human pancreatic cancer

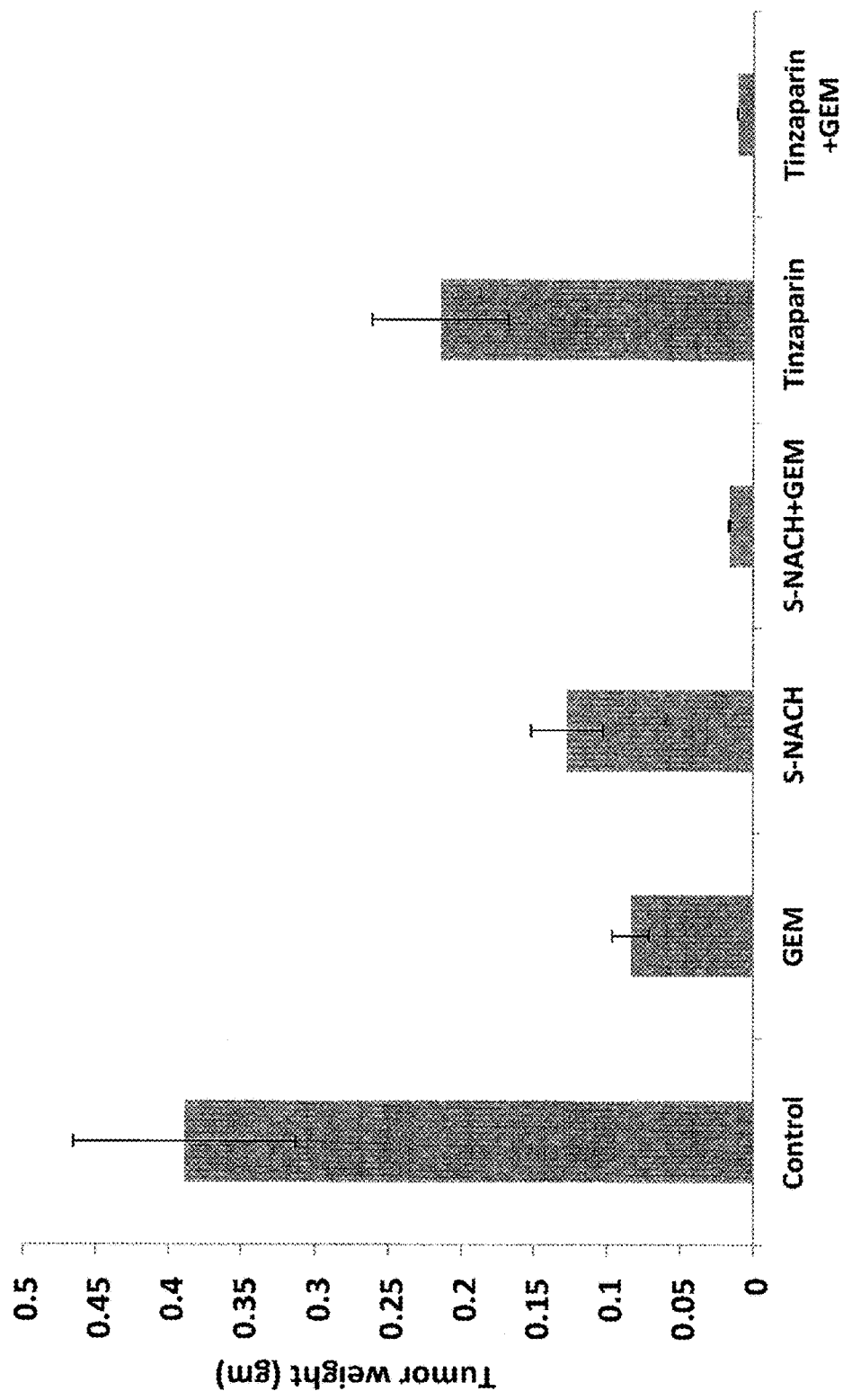
Figure 19: Effect of S-NACH and Tinzaparin reduced pancreatic (SUITE-2) tumor growth after 21 days of treatment Figure 21: Biodistribution of Doxorubicin in tumor versus different organs in NACH versus LMWH tinzaparin treated groups Figure 22: Effect of S-NACH versus the LMWH tinzaparin on bladder cancer growth in nude mice

* $P < 0.05$

Figure 24: S-NACH, Cisplatin and LMWH increased E-cadherin protein expression of bladder cancer cells (253JBV)

Figure 25: S-NACH, Cisplatin and LMWH reduced MMP-2 protein expression of bladder cancer cells (253JBV)

Figure 26: Effect of S-NACH versus Tinzaparin on P-Selectin expression

Figure 27: MicroRNA analysis of Mir21 (oncogene) and Mir15A (pro-apoptotic) in MDA-MB-231 cells: Effect of S-NACH (40 µg/ml)

SULFATED NON-ANTI-COAGULANT LMWH(NACH)

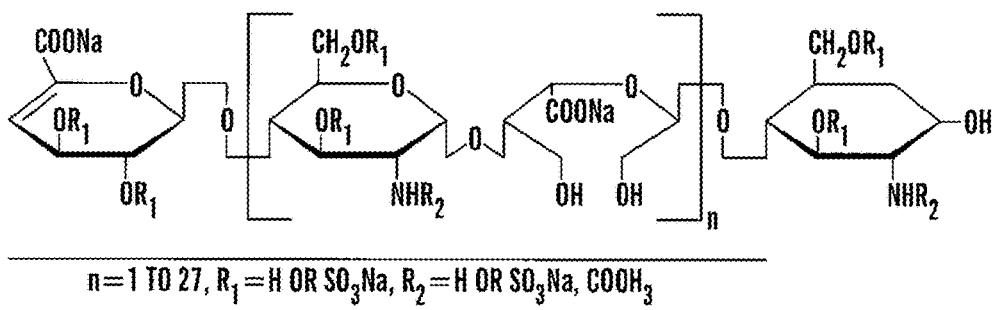

n=1 TO 27, $R_1$=H OR $SO_3Na$, $R_2$=H OR $SO_3Na$, $COOH_3$

STRUCTURAL CHARACTERISTICS;
  - CHEMICAL MODIFICATION OF THE DI-HYDROXYL GROUPS IN THE
    PENTASACCHARIDE REGION OF HEPARIN — REST OF MOLECULE INTACT
• SULPHATE/CARBOXYLATE RATIO: 1.5-2.4/1 (NACH); > 2.4-3.5/1 (SNACH); AND > 3.5-5/1 (S-SNACH)
• CONTENT OF SULPHUR: ≥ 8.5% (w/w)
• INCREASED SULPHATION BY CHROMATOGRAPHY SEPARATION, CHEMICAL OR ENZYMATIC METHODS
• ANTI-COAGULANT ACTIVITY;
  - DEVOID OF AT-III AND LIMITED HC-II BINDING -

*FIG. 29*

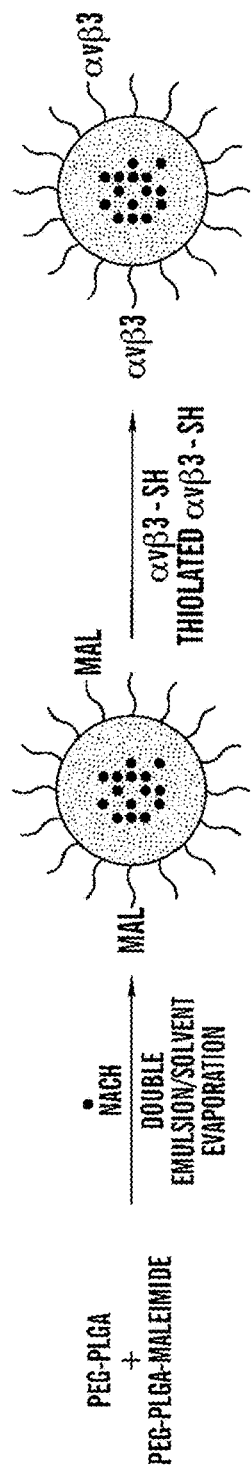
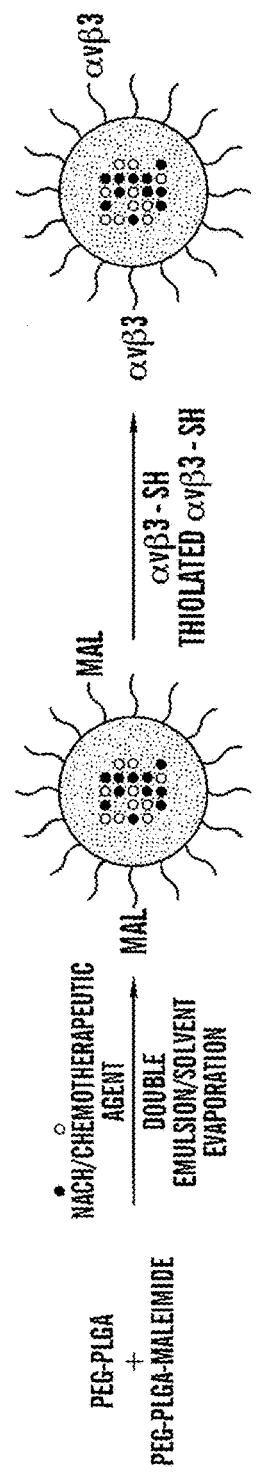
FIG. 30
FIG. 31

A. ZETA POTENTIAL OF TRAZAPARIN
|  |  | MEAN (mV) | AREA (%) | WIDTH (mV) |
|---|---|---|---|---|
| ZETA POTENTIAL (mV): -32.5 | PEAK 1: | -32.5 | 100.0 | 12.1 |
| ZETA DEVIATION (mV): 12.1 | PEAK 2: | 0.00 | 0.0 | 0.00 |
| CONDUCTIVITY (M9/cm): 10.1 | PEAK 3: | 0.00 | 0.0 | 0.00 |
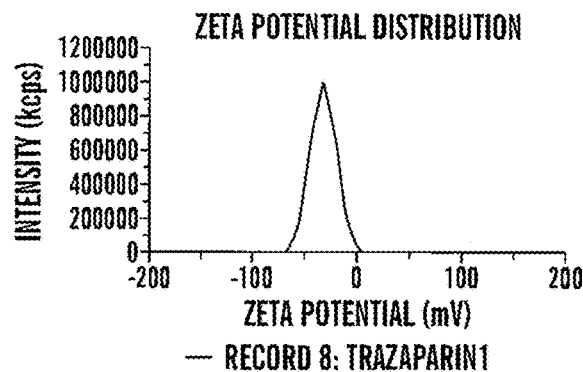
— RECORD 8: TRAZAPARIN1
B. ZETA POTENTIAL OF TRAZAPARIN ENCAPSULATED CHITOSAN NANOPARTICLES
|  |  | MEAN (mV) | AREA (%) | WIDTH (mV) |
|---|---|---|---|---|
| ZETA POTENTIAL (mV): -20.5 | PEAK 1: | -20.5 | 100.0 | 19.3 |
| ZETA DEVIATION (mV): 19.3 | PEAK 2: | 0.00 | 0.0 | 0.00 |
| CONDUCTIVITY (M9/cm): 6.52 | PEAK 3: | 0.00 | 0.0 | 0.00 |
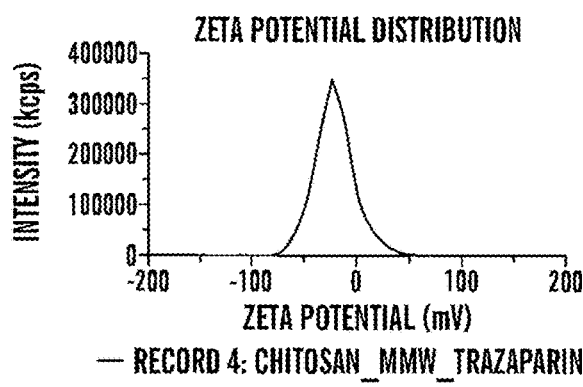
— RECORD 4: CHITOSAN_MMW_TRAZAPARIN
*FIG. 35*

C. ZETA POTENTIAL OF TRAZAPARIN ENCAPSULATED CHITOSAN-PLGA NANOPARTICLES

— RECORD 10: CHITOSAN_MMW_PLGA_TRAZAPARIN

FIGURE: DSL SPECTRA SHOWING SIZE DISTRIBUTION OF TANZAPARIN ENCAPSULATED CHITOSAN_PLGA NANOPARTICLES

A. ZETA POTENTIAL OF TRAZAPARIN
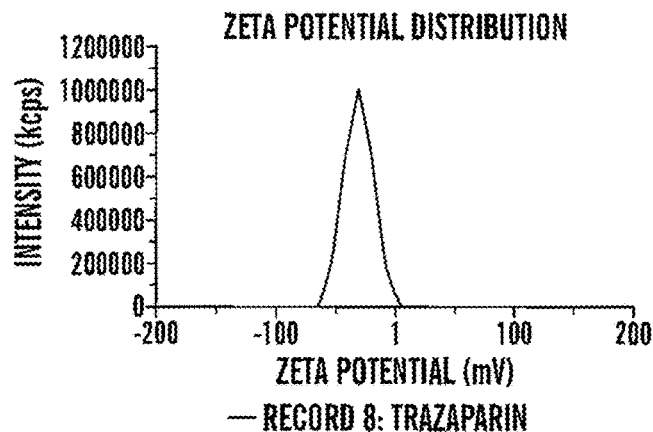
B. ZETA POTENTIAL OF TRAZAPARIN ENCAPSULATED CHITOSAN - PLGA NANOPARTICLES
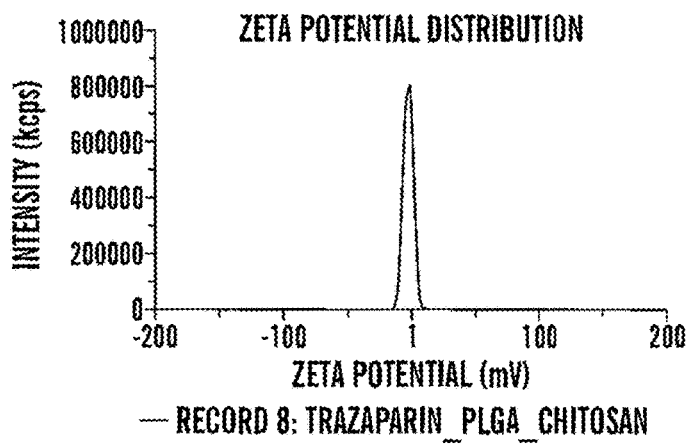
*FIG. 37*

C. ZETA POTENTIAL OF HEPARIN(13) ENCAPSULATED CHITOSAN - PLGA NANOPARTICLES

|  |  | MEAN (mV) | AREA (%) | WIDTH (mV) |
|---|---|---|---|---|
| ZETA POTENTIAL (mV): -3.49 | PEAK 1: | -3.49 | 100.0 | 3.42 |
| ZETA DEVIATION (mV): 3.42 | PEAK 2: | 0.00 | 0.0 | 0.00 |
| CONDUCTIVITY (M9/cm): 0.178 | PEAK 3: | 0.00 | 0.0 | 0.00 |

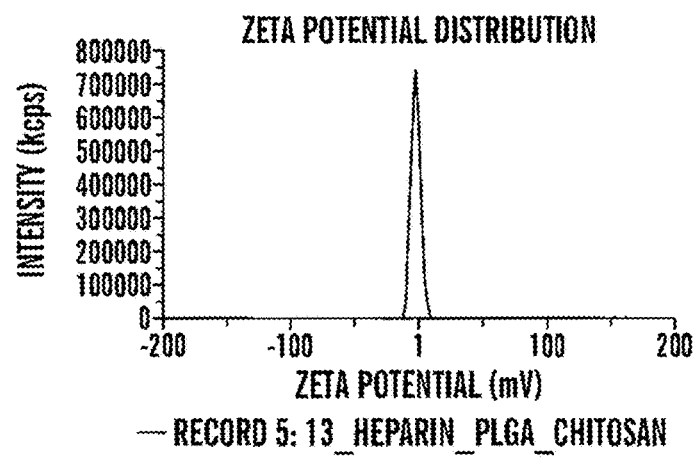

— RECORD 5: 13_HEPARIN_PLGA_CHITOSAN

D. ZETA POTENTIAL OF HEPARIN(8) ENCAPSULATED CHITOSAN - PLGA NANOPARTICLES

|  |  | MEAN (mV) | AREA (%) | WIDTH (mV) |
|---|---|---|---|---|
| ZETA POTENTIAL (mV): 15.2 | PEAK 1: | 15.2 | 100.0 | 4.93 |
| ZETA DEVIATION (mV): 4.93 | PEAK 2: | 0.00 | 0.0 | 0.00 |
| CONDUCTIVITY (M9/cm): 0.129 | PEAK 3: | 0.00 | 0.0 | 0.00 |

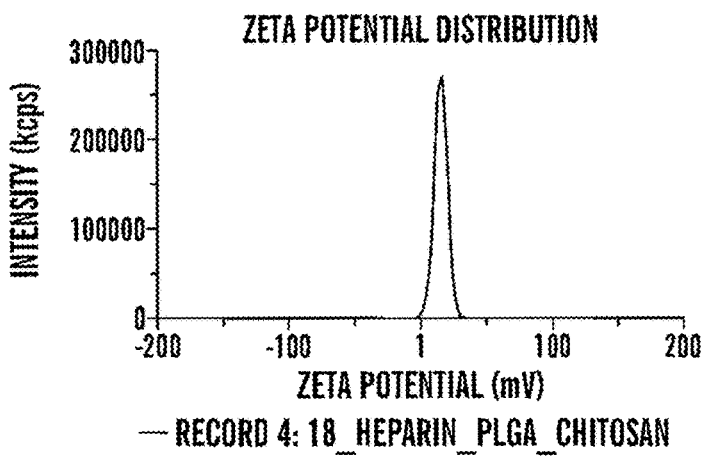

— RECORD 4: 18_HEPARIN_PLGA_CHITOSAN

*FIG. 37 (cont.)*

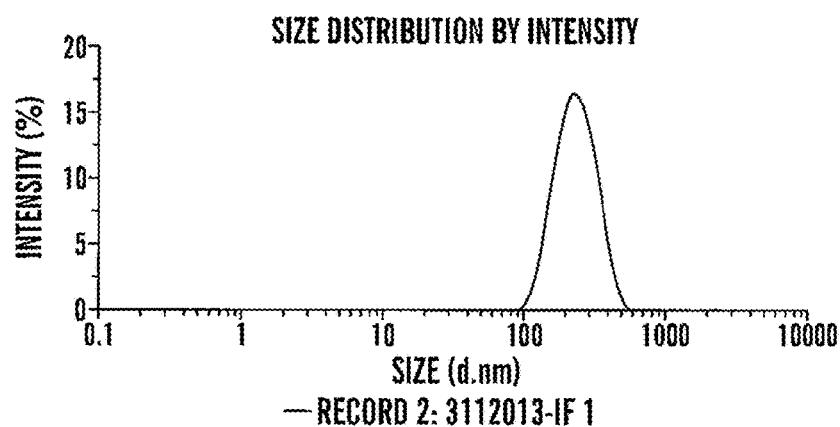
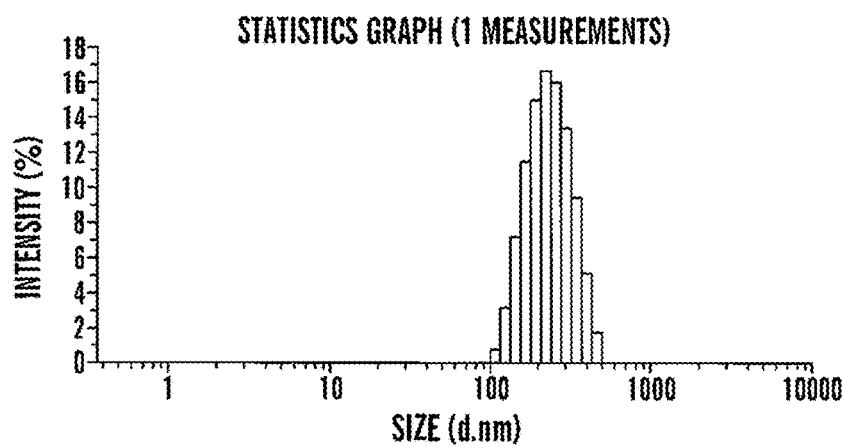
FIG. 41

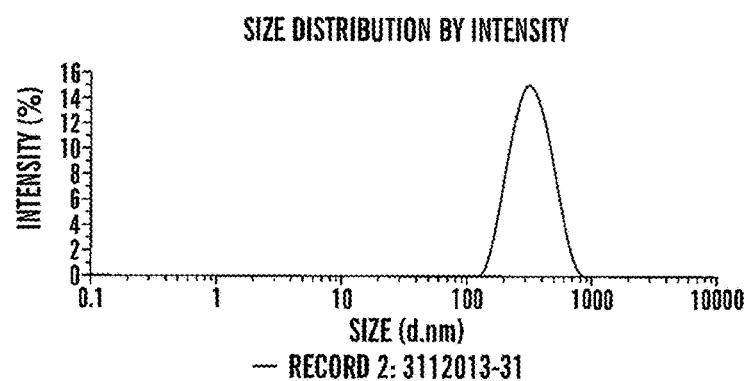
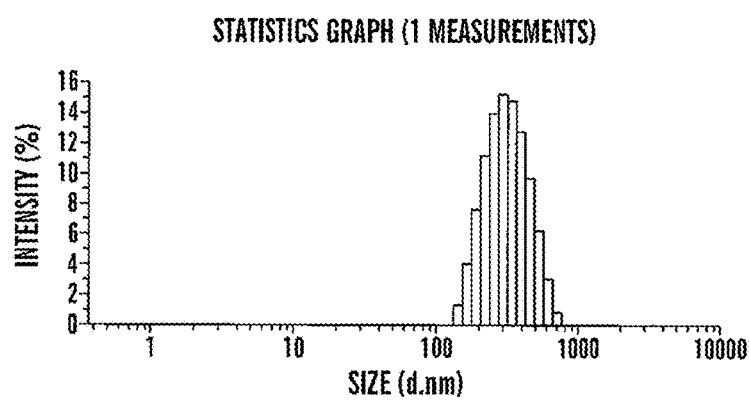
FIG. 43

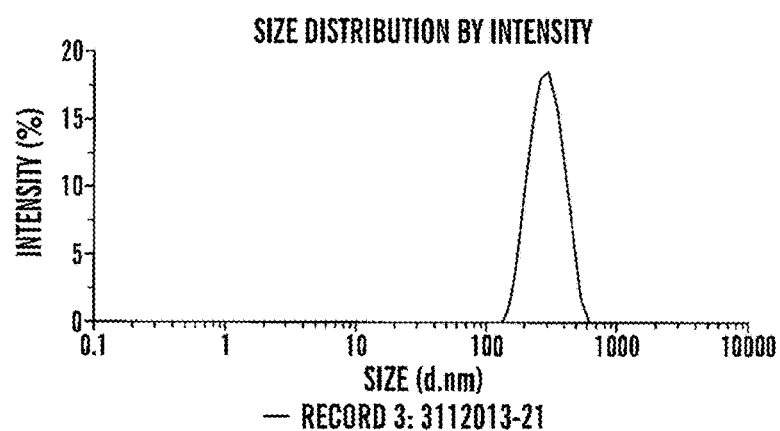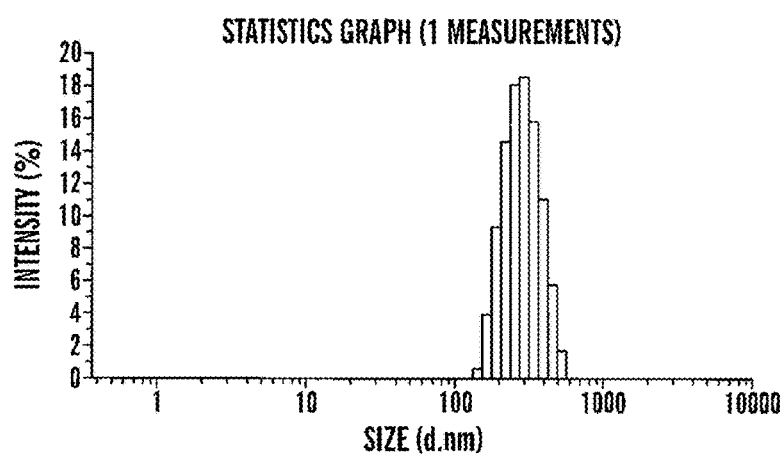
FIG. 44

COMPOSITION AND METHOD FOR SULFATED NON-ANTICOAGULANT LOW MOLECULAR WEIGHT HEPARINS IN CANCER AND TUMOR METASTASIS

RELATED APPLICATIONS

The present invention claims: priority to U.S. Provisional No. 61/896,738, filed on Oct. 29, 2013, which is incorporated herein by reference in its entirety: and priority to U.S. Provisional No. 61/896,770, filed on Oct. 29, 2013, which is incorporated herein by reference in its entirety.

TECHNICAL FIELD

The present invention relates to compositions and associated methods for suppression of primary tumor growth and metastasis by use of sulfated, super-sulfated non-anticoagulant low and ultra-low molecular weight heparins, and their nanoformulations.

BACKGROUND

The Glycosaminoglycans (GAG's) are copolymers of uronic acid and amino hexose with a sequence that has unique biological activity. When prepared from natural sources, this family of heterogeneous macromolecules has sequences that bind specific proteins providing them with various biological activities. Some of the interactions that are of therapeutic utility are between the serine proteases generally and in particular the blood protein anti-thrombin III. This interaction is dependent on special structural sequences that are present in the depolymerized natural product.

The multiplicities of commercially available preparations of heparins are manufactured by diverse processes with variable starting materials yielding products with unique structural components and different biological activities. The commercial products called heparins are thus generally undefined tissue derived panoply of long chain polysaccharides. The structural variability may be a result of the extraction process, the source and condition of the starting materials as well as the collection methods. The resulting biological activities of the product are influenced by these variables.

Heparins are common GAG's made up mainly of D-glucosamine and L-iduronic or D-glucuronic acid sulfated at different sites, having a wide range of molecular weights, and are generally used as anticoagulants and antithrombotic compositions. Low-molecular weight heparins are heterogeneous depolymerized products having a lesser degree of polymerization. The resulting biological properties are a function of polymer chain length and molecular weight distribution. Additionally, the method of preparation of mucosal GAG's yield products with different end groups. One such end group is 2-5 anhydro-D-mannoses, a result of enzymatic depolymerization.

The importance of this class of compounds in clinical medicine is based on its profound action on the coagulation system. Systemic coagulation is an integral part of many diseases and appears as a defense mechanism in trauma. Activation by the coagulation mechanism is a necessary part of the host's immune system. The coagulation system is not only involved in preventing blood loss following trauma, but clotting pathways may be involved in the pathology of allergy and inflammation. Deposits of fibrin surrounding cancer cells may also aid in the progression of growth of malignant tumors. There are multiple other properties of GAG's which are of potential interest as therapeutic agents.

The sequences in the linear GAG polymers that are responsive to the serine protease activity have been chemically synthesized. The natural glycosaminoglycans of interest as well as the synthetic analogs are made up of alternative units of L-iduronic and D-glucuronic acid: D-glucosamino units that are N-sulfated and N-acetylated. The 1-4 linked L-iduronic acids and the D-glucosamino acids have o-sulfate groups.

Although the therapeutic effects of these compounds are well documented, their use is limited because of their poor oral absorption and short half-life. Injectable forms of these compounds exist and efforts have been made to provide an orally absorbable formulation of these compounds. An object of this invention is to provide compositions which are orally absorbable, and thus make them available for a broad spectrum of clinical conditions including cancer.

It has been postulated that the primary cause of death in cancer patients is due to the consequences of metastasis. See Chambers, A. F., A. C. Groom, and I. C. MacDonald, *Dissemination and growth of cancer cells in metastatic sites.* Nat Rev Cancer, 2002, 2(8): p. 563-72.

Heparin is an efficient anti-metastatic agent; it inhibits metastasis by binding to P-selectin and blocking the adhesion between platelets and the disseminated tumor cells in the blood. The use of heparin as an anti-metastatic agent is limited due to the bleeding side effect.

Metastasis is a cascade of events that starts when some cells escape the primary tumor, survive in the circulatory system, and eventually seed in distal metastasis. Ample evidence supports the concept that blood-borne metastasis is significantly facilitated by interactions between disseminating tumor cells and blood platelets that results in the formation of micro-thrombi. See Nash, G. F., et al., *Platelets and cancer*. Lancet Oncol, 2002, 3(7): p. 425-30. See Ruiter, D. J., et al., *Tumour metastasis: is tissue an issue?*, Lancet Oncol, 2001, 2(2): p. 109-12. See Karpatkin, S. and E. Pearlstein, *Role of platelets in tumor cell metastases*, Ann Intern Med, 1981. 95(5): p. 636-41. See Gasic, G. J., *Role of plasma, platelets, and endothelial cells in tumor metastasis*, Cancer Metastasis Rev, 1984, 3(2): p. 99-114. See Honn, K. V., D. G. Tang, and Y. Q. Chen, *Platelets and cancer metastasis: more than an epiphenomenon*, Semin Thromb Hemost, 1992, 18(4): p. 392-415.

Selectins are a family of cell adhesion molecules, and are divided into three groups: E, L and P, which are found on the surface of endothelial cells, leukocytes, and platelets, respectively. Selectins have roles in hemostasis, inflammation, and the immune response. See McEver, R. P., *Selectin-carbohydrate interactions during inflammation and metastasis*, Glycoconj J, 1997. 14(5): p. 585-91. See Ley, K, *The role of selectins in inflammation and disease*, Trends Mol Med, 2003, 9(6): p. 263-8.

P-selectin was found to be most relevant in the process of tumor metastasis and has been studied extensively. The adhesions that form between tumor cells and platelets via P-selectin are required to create the metastatic microthrombi. See Borsig, L., et al., *Heparin and cancer revisited: mechanistic connections involving platelets, P-selectin, carcinoma mucins, and tumor metastasis*, Proc Natl Acad Sci USA, 2001, 98(6): p. 3352-7.

The activation of endothelial P-selectin also plays a role in the arrest of circulating tumor cells, and their eventual extravasation from the blood vessel into the distal organs. See Ludwig, R. J., et al., *Endothelial P-selectin as a target* of heparin action in experimental melanoma lung metastasis, Cancer Res, 2004, 64(8): p. 2743-50.

Sialylated fucosylated glycans are the ligands for P-selectin, and tumors with high expression of these ligands typically have poor prognosis due to high rates of metastasis. See Stone, J. P. and D. D. Wagner, *P-selectin mediates adhesion of platelets to neuroblastoma and small cell lung cancer*, J Clin Invest, 1993, 92(2): p. 804-13. See Mannori, G., et al., *Differential colon cancer cell adhesion to E-, P-, and L-selectin: role of mucin-type glycoproteins*, Cancer Res, 1995, 55(19): p. 4425-31.

Heparin was found to be an efficient ligand for P-selectin and blocks the binding of P-selectin with tumor cells, and therefore attenuates tumor metastasis in animal models. See Nelson, R. M., et al., *Heparin oligosaccharides bind L- and P-selectin and inhibit acute inflammation*, Blood, 1993, 82(11): p. 3253-8. See Koenig, A., et al., *Differential interactions of heparin and heparan sulfate glycosaminoglycans with the selectins. Implications for the use of unfractionated and low molecular weight heparins as therapeutic agents*, J Clin Invest, 1998, 101(4): p. 877-89.

By depriving the circulating tumor cells their platelet shield, they become more fragile in the harsh environment of the circulatory system and are more readily cleared by the immune system.

Heparin is best known for its anticoagulant properties, because it binds to anti-thrombin III. See Rosenberg, R. D. and P. S. Damus, *The purification and mechanism of action of human antithrombin-heparin cofactor*, J Biol Chem, 1973, 248(18): p. 6490-505.

Heparin's anti-metastatic properties are a result of one or more of the following: the inhibition of heparenase, the blocking of P- and L-selectins (see Zacharski, L. R. and J. T. Loynes, *The heparins and cancer*, Curr Opin Pulm Med, 2002, 8(5): p. 379-82)); inhibition of tissue factor (see Kasthuri, R. S., M. B. Taubman, and N. Mackman, *Role of tissue factor in cancer*, J Clin Oncol, 2009, 27(29): p. 4834-8); and the inhibition of angiogenesis (see Capila, I. and R. J. Linhardt, *Heparin-protein interactions*, Angew Chem Int Ed Engl, 2002, 41(3): p. 391-412).

Low molecular weight heparin (LMWH) has been shown to decrease tumor metastasis in animal experiments and clinical trials, but the use of heparin and its derivatives as anti-metastatic agents is limited because of its risk in inducing adverse bleeding complications. A meta-analysis performed in 2007 showed an increase in bleeding in patients treated with LMWH as an anti-metastatic medication. See Kuderer, N. M., et al., *A meta-analysis and systematic review of the efficacy and safety of anticoagulants as cancer treatment: impact on survival and bleeding complications*, Cancer, 2007, 110(5): p. 1149-61.

Tumor excision of a primary cancer with no metastasis has been the cornerstone treatment for most cancers, but scientific evidence has revealed that cancer excisional surgery itself can increase the risk of metastasis. See van der Bij, G. J., et al., *The perioperative period is an underutilized window of therapeutic opportunity in patients with colorectal cancer*, Ann Surg, 2009, 249(5): p. 727-34.

BRIEF SUMMARY

The present invention provides a nanoformulation that includes nanoparticles. Each nanoparticle includes a shell within which a glycosaminoglycan (GAG) is encapsulated. The GAG is ionically or covalently bonded to the shell. The GAG is selected from the group consisting of sulfated non-anticoagulant heparin (SNACH), super-sulfated non-anticoagulant heparin (S-SNACH), and a combination thereof. The shell includes Poly (lactic-co-glycolic acid) (PLGA), Polyethylene Glycol (PEG)-PLGA, maleimide-PEG-PLGA, chitosan, chitosan-PLGA, methoxy-polyethyleneglycol-poly (lactide-co-glycolide) (MPEG-PLGA)-(maleimide-PEG-PLGA), PLGA-Polycaprolate, or calcium alginate. A method of using the nanoformulation to treat a cancer in a subject includes administering to the patient a therapeutically effective amount of the nanoformulation for treating the cancer.

BRIEF DESCRIPTION OF THE DRAWINGS

FIG. 5 illustrates the comparative anti-IIa activity for the LMWH tinzaparin and enoxaparin versus NACH as compared to control, in accordance with embodiments of the present invention.

FIG. 6 shows a lack of effect for NACH as compared to the LMWH enoxaparin on clotting time or time to clot initiation after intravenous administration in mice at 10 mg/kg, each, in accordance with embodiments of the present invention.

FIG. 7 compares test compounds (tinzaparin and SNACH) for bleeding time in mice, in accordance with embodiments of the present invention.

FIG. 8 depicts NACH or LMWH inhibition of pancreatic tumor growth and angiogenesis in the Chick Chorioallantoic membrane (CAM)-tumor implant model, in accordance with embodiments of the present invention.

FIG. 9 depicts an effect of S-NACH, tinzaparin, and gemcitabine (GEM) on human pancreatic carcinoma, in accordance with embodiments of the present invention.

FIG. 10 shows immediate response within the first day of treatment in halting tumor growth for either S-NACH or tinzaparin, in accordance with embodiments of the present invention.

FIG. 11 depicts an effect of S-NACH on pancreatic cancer growth 24 hours after orthotopic implant in nude mice, in accordance with embodiments of the present inv.

FIG. 12 depicts an effect of S-NACH versus the LMWH tinzaparin on the IVIS signal intensity of pancreatic tumor growth in nude mice, in accordance with embodiments of the present invention.

FIG. 13 depicts an effect of S-NACH versus Tinzaparin with or without on pancreatic tumor growth mice, in accordance with embodiments of the present invention.

FIG. 14 depicts an effect of S-NACH versus tinzaparin on pancreatic tumor necrosis, in accordance with embodiments of the present invention.

FIG. 15 compares tumor metastasis to the liver after injecting cancer cells into the spleen, in accordance with embodiments of the present invention.

FIG. 16 compares tumor relapse after surgical excision of pancreatic cancer liver metastasis after excision of pancreatic cancer, in accordance with embodiments of the present invention.

FIG. 17 depicts an anti-metastatic effect of S-NACH into the lung of nude mice, in accordance with embodiments of the present invention.

FIG. 18 depicts molecular effects of NACH versus LMWH in human pancreatic cancer, in accordance with embodiments of the present invention.

FIG. 19 depicts an effect of S-NACH versus LMWH Tinzaparin on orthotopically implanted pancreatic tumor (SUITE2) in nude mice after 21 days of treatment, in accordance with embodiments of the present invention.

FIG. 29 provides a characterization of SNACH, in accordance with embodiments of the present invention.

FIG. 30 is a schematic diagram for preparation of αvβ3 conjugated NACH doped PEG-PLGA nanoparticles, in accordance with embodiments of the present invention.

FIG. 31 is a schematic diagram for preparation of αvβ3 conjugated S-NACH and chemotherapeutic agent doped PEG-PLGA nanoparticles, in accordance with embodiments of the present invention.

FIG. 37 depicts zeta potential of tinzaparin, zeta potential of tinzaparin encapsulated chitosan-PLGA nanoparticles, zeta potential of heparin (13) encapsulated chitosan-PLGA nanoparticles, and zeta potential of heparin (8) encapsulated chitosan-PLGA nanoparticles, in accordance with embodiments of the present invention.

FIG. 41 depicts, for Chitosan-SNACH-NPs (Zav=200 nm), a size distribution by intensity and a size in nanometers, in accordance with embodiments of the present invention.

FIG. 43 depicts, for Chitosan-DHA/SNACH-NPs (Zav=248 nm), a size distribution by intensity and a size in nanometers, in accordance with embodiments of the present invention.

FIG. 44 depicts, for Chitosan-ACA-DHA/SNACH-NPs (Zav=252 nm), a size distribution by intensity and a size in nanometers, in accordance with embodiments of the present invention.

DETAILED DESCRIPTION

Figure 1:
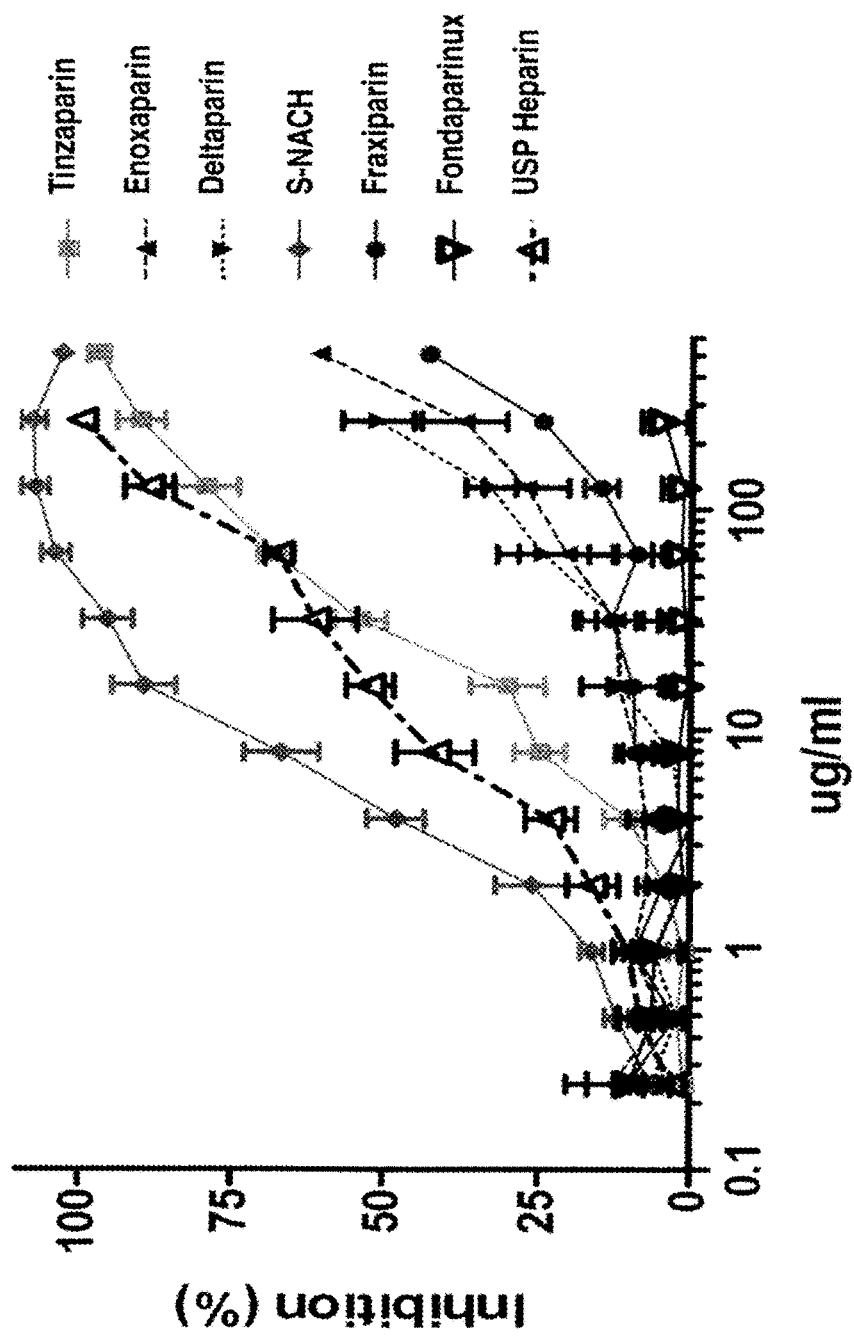
FIG. 1 depicts comparative efficacy of S-NACH versus heparin and Low or ultra-Low Molecular Weight Heparins, in accordance with embodiments of the present invention.

Experiments conducted with respect to the present invention have tested and developed the inhibitory effect of heparin derivatives on blood-borne metastasis and on surgically induced metastasis. In order to develop effective therapeutic formulations for treating cancer and metastasis, these tests have explored the interrelationships among metastasis, selectin, and heparin derivatives. As a result, the present invention has developed non-anticoagulant heparin derivatives (NACH) including sulfated non-anticoagulant heparin (SNACH) and super-sulfated non-anticoagulant heparin (S-SNACH) for overcoming the complication of adverse bleeding that accompanies the use of heparin or Low Molecular Weight Heparins (LMWH) for blocking the binding of P-selectin with tumor cells.

The present invention suppresses primary tumor growth and metastasis by sulfated and super-sulfated low and ultra-low molecular weight non-anticoagulant heparins (SNACH and S-SNACH, respectively) without adverse bleeding as compared to Low Molecular Weight Heparins (LMWH). Additionally, SNACH or S-SNACH enhances chemotherapy responsiveness in chemo-resistant tumors.

SNACH is also called S-NACH. SNACH and S-SNACH are Sulfated and Super-Sulfated Non-anticoagulant GAG derivatives, respectively. GAGs denote modified glycosaminoglycans.

Definitions: low sulfated Non-anticoagulant Low Molecular Weight Heparin (NACH) has a sulfate/carboxylate ratio in a range of 1.5 to 2.4/1, SNACH has a sulfate/carboxylate ratio in a range of greater than 2.4 to 3.5/1, and S-SNACH has a sulfate/carboxylate ratio in a range of greater than 3.5 to 5.0/1. The preceding sulfate/carboxylate ratio is a ratio of the number of sulfate groups to the number of carboxylate groups.

Heparin and its derivatives are known to attenuate cancer metastasis, but have not been used clinically due to adverse bleeding effects at relatively low doses. Studies associated with the present invention examined the ability of a low molecular weight heparin (LMWH), a sulfated non-anticoagulant Low and Ultra-Low Molecular Weight heparins (SNACH) and super-sulfated (S-SNACH) to inhibit metastasis of a growing primary mass and metastasis following surgical excision of primary tumor in a pancreatic cancer mouse models. First, the effectiveness of the test compounds was examined by using a platelet-cancer cell adhesion assay. The adherent pancreatic Mpanc96 cells (Lucefrin transfected) were grown in cultural plate. Test compounds were added at different concentrations to fluorescence labeled platelets prior to adding the test compounds to the cancer cells. After 45 minutes of incubation, unbound platelets were washed with buffer and the bound platelets were quantified using fluorescence plate reader. Animal experiments were also conducted using athymic female mice to examine the efficacy and safety of SNACH and S-SNACH versus the LMWH tinzaparin on experimental metastasis, surgical, and spontaneous metastasis.

Different groups of mice received either saline (control), LMWH, SNACH or S-SNACH, followed by injection of luciferase transfected pancreatic cancer cells into the mouse spleen. The treatment continued daily for two weeks. IVIS imaging was done once a week to measure the metastatic load to various organs. The tumor burden measurements were based on the bioluminescence signal intensity of the pancreatic cancer cells. The second experiment was intended to study the effect of the compounds (LMWH, SNACH, and S-SNACH) on metastasis after tumor excision surgery. Pancreatic Mpanc96 cells were injected into the tail of the pancreas and one week later animals were randomized into different groups. One group received saline and another group received LMWH, SNACH, and S-SNACH at 30 minutes before resection of the pancreatic tumor, followed by daily treatment for 3 weeks. Tumor metastasis was evaluated by IVIS imagining. A bleeding time experiment was done to evaluate the relative effect on bleeding time. SNACH significantly decreased the level of metastasis ($P<0.05$), and S-SNACH diminished the level of metastasis versus control and LMWH. SNACH was also able to reduce surgically induced metastasis ($P=0.017$). Neither SNACH nor S-SNACH affected bleeding time as compared to control or LMWH, while LMWH significantly ($P<0.0001$) prolonged bleeding as compared to control or S-NACH groups. These data suggest that SNACH are effective and safe anti-metastatic agents and warrant further clinical evaluation. Additionally, investigations in conjunction with the present invention investigated anti-tumor, anti-angiogenesis, and anti-metastatic effects of S-NACH in a metastatic mouse model of pancreatic cancer as compared to LMWH. S-NACH or the LMWH tinzaparin with or without administration of Gemcitabine. Tumor luminescent signal intensity, weight, and histopathology were assessed at the termination of the study. S-NACH and LMWH efficiently inhibited tumor growth and metastasis, without any bleeding side effects observed with S-NACH as compared to tinzaparin.

Investigations in conjunction with the present invention examined the inhibitory effect of SNACH and S-SNACH on post-surgical metastasis using orthotopically implanted cancer in a mouse model. In the present investigations, the anti-cancer efficacy of S-NACH versus LMWH in suppressing tumor growth and tumor angiogenesis for various cancer cell types was determined. Additionally, the effect of LMWH, SNACH or S-NACH with regard to anti-metastasis efficacy and safety (hemostasis) in experimental metastasis model and after primary tumor surgical incision were determined.

In one embodiment, a nanoparticle of the present invention comprises a positively charged shell and negatively charged Glycosaminoglycans (S-NACH and/or LMWH) encapsulated within the shell and ionically bonded to the positively charged shell. The shell may comprise PLGA-PEG.

EXAMPLE 1

Preparation of Sulfated Non-Anticoagulant Heparin (S-NACH)

Unfractionated porcine Heparin or bioengineered heparin was fragmented by periodate oxidation based on a procedure from Islam et al. See Islam T, Butler M, Sikkander S A, Toida T, Linhardt R J, *Further evidence that periodate cleavage of heparin occurs primarily through the antithrombin binding site*, Carbohydr Res. 2002, 337(21-23): 2239-43.

Heparin, sodium salt (20 g, 1.43 mmol) was dissolved in 175 mL of distilled water. The pH was adjusted to 5.0 using 1 N HCl, NaIO4 (15 g, 0.07 mol), dissolved in 500 mL water, which was added in a single portion with stirring. The pH was readjusted to 5.0 using 1 N HCl and left for 24 hours at 4° C. in the dark. The solution was dialyzed against 4 volumes of water (with one change of water) for 15 hours at 4° C. To the approximately 1.5 L of solution obtained after dialysis, 32 mL of 10 N NaOH was added. The solution was stirred at room temperature for 3 hours. To prevent the development of colored products, this step was done in the dark. NaBH$_4$ (1 g, 0.026 mol) was added in one portion, and the approximately 1.5 L of solution was stirred for 4 hours. The pH was then adjusted to 4.0 using 37% HCl, and the solution was stirred for an additional 15 minutes. The solution was neutralized to pH 7.0 using 1 N NaOH and NaCl (32.8 g, 0.56 mol) followed by the addition of 2.54 L ethanol. The solution was left for 3 hours without stirring, and the precipitate was recovered by centrifugation (22,000×g) for 20 minutes. The precipitate, recovered by decantation, was suspended in 400 mL absolute ethanol. The solution was filtered using a Buchner funnel, and the recovered solids were left to dry for 5 hours under vacuum affording 14.2 g of product. The product was dissolved in 190 mL of water. NaCl (2.8 g, 0.05 mol) was added, and the pH was adjusted to 3.5 using 1 N HCl. The volume was adjusted to 280 mL using water. Absolute ethanol (240 mL) was added with stirring. The solution was stirred 15 minutes and then left without stirring for 10 hours at room temperature. After decanting, the precipitate was recovered and dissolved in water. The ethanol was removed by rotary evaporation under reduced pressure, and the residue was freeze dried affording 10 g of Low Molecular Weight NACH. Low to ultra-Low Molecular Weight NACH was prepared by controlled depolymerization and concurrent chemical or enzymatic sulfation of heparin with a mixture of sulfuric and chlorosulfonic acid or enzymatic sulfation.

EXAMPLE 2

Cancer Cells

Pancreatic cancer cell line MPanc96 and its luciferase transfected Mpanc96-luc cells were grown in DMEM supplemented with 5% fetal bovine serum, 1% penicillin, and 1% streptomycin. Cells were cultured at 37° C. to sub-confluence and treated with 0.25% (w/v) trypsin/EDTA to affect cell release from culture flask. After washing cells with culture medium, cells were suspended in DMEM (free of phenol red and fetal bovine serum) and counted. These cells were also genetically modified to contain luciferase, which emits signals that can be detected by in vivo imaging system (IVIS).

Other human pancreatic cancer cell lines MIA-PaCa-2 and BxPC-3 were obtained from the American Type Culture Collection (Rockville, Md.). Two different pancreatic cancer cell lines were chosen for study because each cell line exhibits different characteristics in vivo with respect to rate of growth and metastasis, with the former showing more rapid and extensive dissemination. Cells were maintained in Dulbecco's Minimal Essential Media supplemented with 10% fetal calf serum, 2 mM glutamine, 100 U/ml penicillin, 100 μg/ml streptomycin, and 0.25 μg/ml Amphotericin B. Luciferase transfected cancer cells were used to examine their adhesion to P-selectin, endothelial cells, and human vessel segments.

EXAMPLE 3

Platelet-Cancer Cell Adhesion Assay

A cancer cells-platelets adhesion assay was used to test the efficacy of the test compounds in inhibiting the adhesion between P-selectin and tumor cells. This was done by growing the Mpanc96 cancer cells in 96-well plate to 100% confluence. Ten ml of human blood was drawn by vacutainer tube containing citrate acid and dextrose and stored at 4° C. overnight. After 24 hours, the supernatant of the blood was collected (platelet-rich plasma). The platelet rich plasma was centrifuged for 10 minutes at 1000×g and resuspended in 10 ml PBS. The platelets were labeled with Calcien AM fluorescence dye and incubated for 30 minutes at 37° C. The platelets were then washed five times with PBS by centrifuging at 2,000×g for 10 minutes. The test compounds were mixed with the platelets 30 minutes prior to adding them to the cancer cells to allow the compounds to bind to the P-selectin of the platelets. The concentrations ranged from 5 ug/ml to 20 ug/ml for LMWH and S-SNACH. After 45 minutes the unbound platelets were washed with PBS and the fluorescence plate reader was used to measure the amount of adherent platelets.

FIG. 1 depicts comparative efficacy of S-NACH versus heparin and Low or ultra-Low Molecular Weight Heparins, in accordance with embodiments of the present invention. FIG. 1 depicts an effect of SNACH versus different heparin derivatives on colon cancer adhesion to P-selectin. FIG. 1 depicts a comparative inhibitory efficacy of colon cancer to P-selectin adhesion for SNACH versus heparin, LMWHs or fondaparinux

EXAMPLE 4

In Vitro Human Vessel Perfusion Model

Based on published data obtained on the tumor/vessel adherence characteristics in this model [Mousa S A., *Comparative pharmacodynamic assessment of the antiangiogenesis activity of heparin and low-molecular-weight heparin fractions: structure function relationship*, Clin Appl Thromb Hemost, 2013, 19(1):48-54], umbilical vein was utilized for all studies. Following informed consent, fresh umbilical cord was obtained, using a sterile technique, from the placenta following normal delivery via cesarean section from patients at local hospitals. Approximately 20 cm of the cord is excised, rinsed and wiped free of blood using cold 0.9% saline and sterile gauze. Then cold saline was used to flush the vein clean of blood. Two sections of umbilical cord (approximately 3 cm each) are cut longitudinally to expose the vein surface and are pinned to the silastic base of the chamber using 27 G×1 inch needles. The vein surface was optionally denuded with 3-4 gentle strokes of a cotton swab, depending on the different conditions to be tested. Any leftover vein was cut longitudinally and immediately fixed with neutral buffered formalin (NBF) as a control tissue.

The vein segments were perfused for 24 hours with cancer cells in platelet-rich plasma (PRP) under venous flow conditions (70 ml/min). The perfusate was gently bubbled with 95% $O_2$ and 5% $CO_2$ to maintain physiological conditions. The concentration of cancer cells added to the perfusate mixture was $2.0 \times 10^5$ cells/ml. Blood gases of the perfusate were measured 15 minutes after the start and just prior to the end of the perfusion period to confirm that physiological conditions were maintained. Perfusate samples were also collected just prior and after the perfusion period and stored at −20° C. Each vein segment was then fixed with NBF solution for an additional 24 hours. Sections of the vein obtained from each end of the segment, as well as the middle, are separated via slicing. The sections were processed within 48 hours, paraffin-embedded, and cut into three 4-μm-thick sections per slide. Immunohistochemical staining with hematoxylin/eosin as well as pan-cytokeratin was used to assess the integrity of the tissue to label the cancer cells. Afterwards, morphometric analysis is performed. All perfusion experiments were performed five times. Statistical significance was determined by using a paired t-test.

Normal autologous human cord blood obtained before harvesting of each umbilical cord was used for preparation of PRP. Perfusate was prepared from fresh whole blood collected in 3.2% citrate tube.

In an in vitro perfusion model, the custom-designed perfusion chamber, made of Plexiglas, was 12 cm long and 4.5 cm wide with a 1-cm-thick silastic base. The chamber has outlets on each end that can be connected via rubber tubing to a 250 ml flask containing the perfusate. The perfusion chamber was placed in a glove box to provide a sterile environment during perfusion. The perfusion chamber, all surgical tools, glassware, and pump tubing (food-grade Norprene) are autoclaved prior to use. Matched parallel experiments were run utilizing two chambers in which vein segments are from the same donor and platelet-rich plasma (PRP) perfusate was from a single donor. Two chambers, with umbilical cord vein segments pinned to the silastic base, were inside the sterile glove box. Perfusate is being pumped into the chambers from two individual flasks. The model maintains human physiologic pH, pCO2, and pO2 levels throughout the 24-hr perfusion period. Physiologic measurements were taken 15 minutes after the commencement and at the end of the perfusion period.

EXAMPLE 5

Morphometric Analysis

The initial attachment of a cancer cell, in which a cell was bound to the vessel wall by a small amount of membrane and maintains its original shape, is termed a contact cancer cell. The latter stage in which a cancer cell was more intimately bound to the sub-endothelium before penetrating was termed cell adhesion. The final stage in which a cancer cell has fully or partially infiltrated the sub-endothelial surface was termed cell penetration. Clusters of two or more cells were quantified as clusters and noted for the number of cells per cluster. By quantifying the percentages of cells in the contact, adhesion, and penetration stages, cancer cell attachment to the sub-endothelium was determined, which is the first step in metastasis. The vein surface length was measured to calculate the number of cancer cells attached per unit length. Metastatic potential is characterized by calculating the number of cells attached per unit length and then normalizing for cancer cell concentration in the perfusate.

With respect to morphologic characteristics of tumor cell adhesion and invasion in the vessel segment perfusion system, two breast cancer cell lines have been perfused over either umbilical cord or adult saphenous veins segments.

Figure 2:
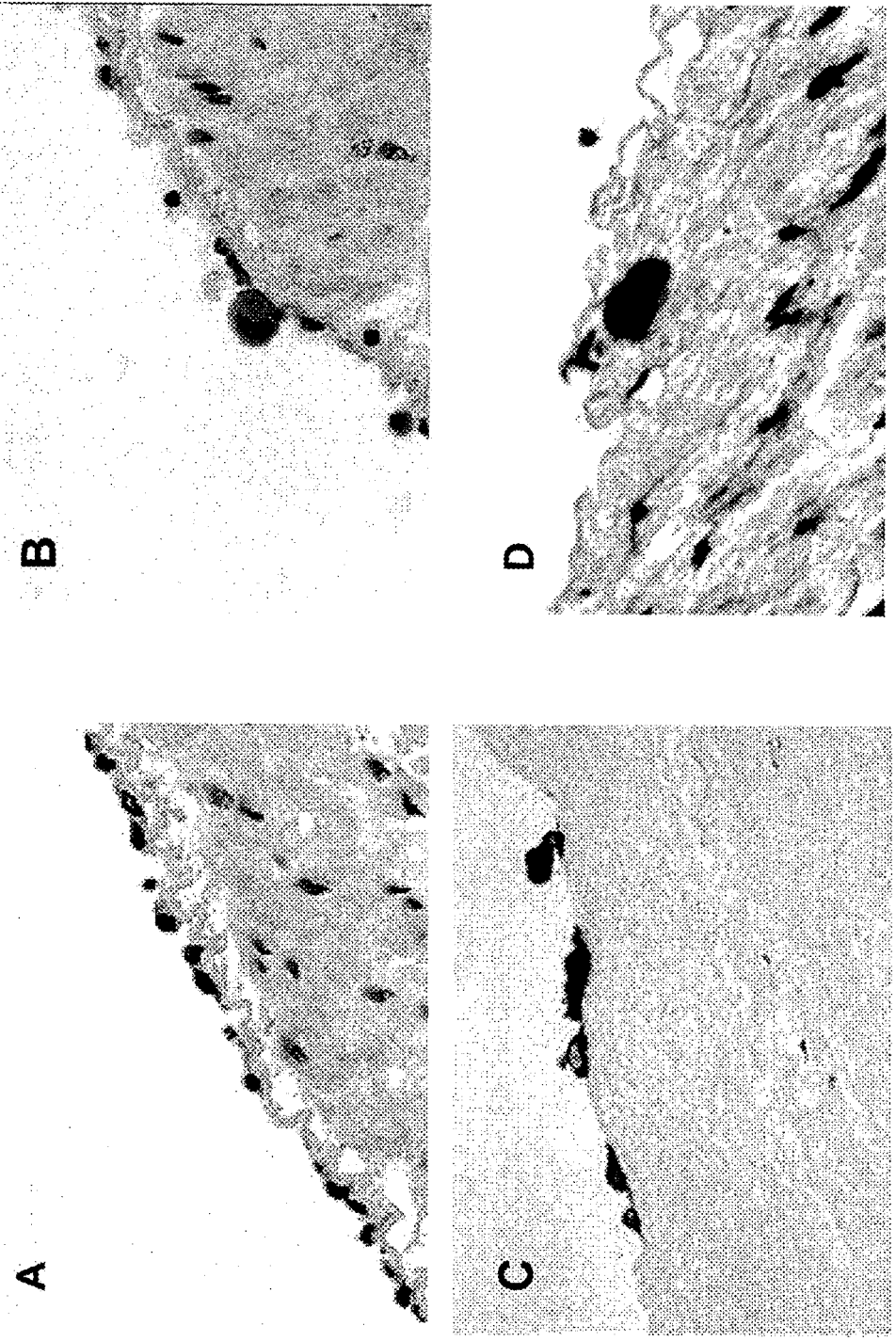
FIGS. 2A, 2B, 2C and 2D depict morphologic characteristics of tumor cell adhesion and invasion in the vessel segment perfusion system, in accordance with embodiments of the present invention.

FIGS. 2A, 2B, 2C and 2D depict morphologic characteristics of tumor cell adhesion and invasion in the vessel segment perfusion system, in accordance with embodiments of the present invention. With both cell lines, MCF-7 and MDA-MB-231, adhesion of the cancer cells occurs only with the sub-endothelium and not with the endothelial cells (FIG. 2A). Different stages of interaction were observed as demonstrated in FIG. 2B, adhesion in FIG. 2C, and penetration in FIG. 2D, legends below. The stages of interaction can be seen with both individual and clustered cells.

Figure 3:
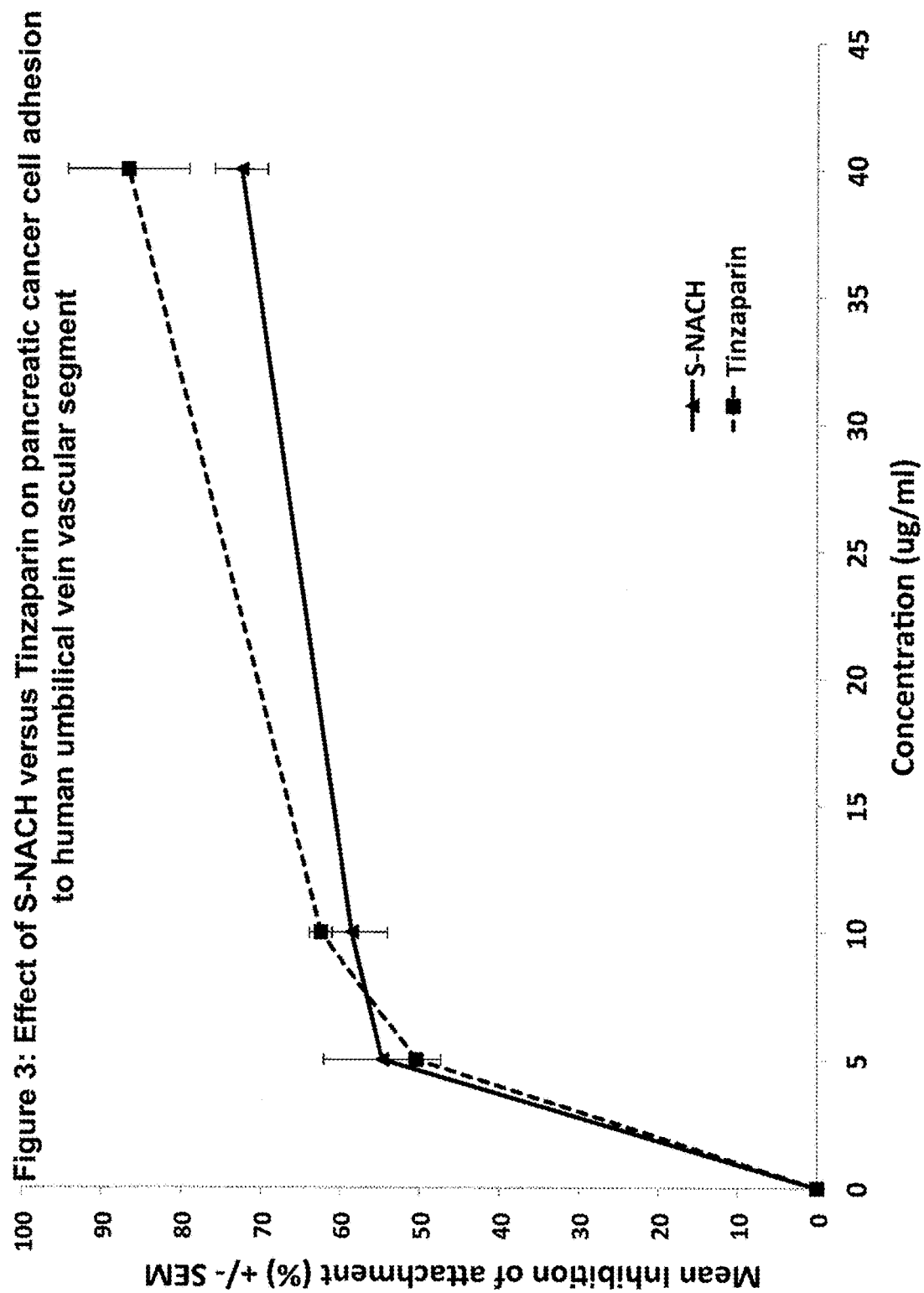
FIG. 3 shows the comparable anti-adhesive potency of S-NACH and the LMWH tinzaparin in suppressing pancreatic cancer cell adhesion, in accordance with embodiments of the present invention.

FIG. 3 shows the comparable anti-adhesive potency of S-NACH and the LMWH tinzaparin in suppressing pancreatic cancer cell adhesion, in accordance with embodiments of the present invention. FIG. 3 depicts an effect of SNACH versus Tinzaparin on pancreatic cancer cell adhesion to human umbilical vein vascular, in accordance with embodiment of the present invention.

EXAMPLE 6

Anti-Factor Xa Assay

The Anti-factor Xa assay is a kit (Instrumentation Laboratory Bedford, Mass.) based on a synthetic chromogenic substrate and Factor Xa activation. The kit provides the chromogenic substrate needed and Factor Xa reagent, human anti-thrombin, and buffer. Heparin is analyzed as a complex with anti-thrombin. Purified human anti-thrombin is added to the test plasma and Factor Xa is added in excess, which is neutralized by the heparin-anti-thrombin complex. Residual Factor Xa is quantified with the synthetic chromogenic substrate. Para-nitroaniline is released and monitored kinetically by the automated coagulation analyzer at 405 nm and is inversely proportional to the heparin level in the sample. The assay is run on a fully automated coagulation analyzer, ACL 8000, manufactured by Beckman Coulter. The absorbance result is then converted to activity (U/mL) via a calibration curve. The chromogenic substrate, Factor Xa reagent, and human anti-thrombin are all dissolved with distilled $H_2O$ ($dH_2O$) to the appropriate volume and then kept at room temperature for 30 minutes before use. The buffer comes in a concentrated form and must be diluted 1:10 with $dH_2O$ and finally made into a working buffer solution by adding 24 mL of diluted buffer to 1 mL of reconstituted anti-thrombin reagent. Samples for the anti-factor Xa assay are run with a concentration of 20% plasma. Blank, pooled rabbit plasma is used to fulfill this requirement when diluting samples with PBS. The samples are diluted appropriately to yield absorbance values within the linear range of activity units based on the calibration curve.

The calibration curve is made using the USP Reference Standard Heparin. The reference standard stock is 1000 U/mL when reconstituted with $dH_2O$. This stock solution of heparin was diluted to various concentrations ranging from 0.001 to 10 U/mL for use as points on the calibration curve. Using the calibration curve, absorbance values for each sample were converted to U/mL, and thereby standardized and graphed to show a profile.

Figure 4:
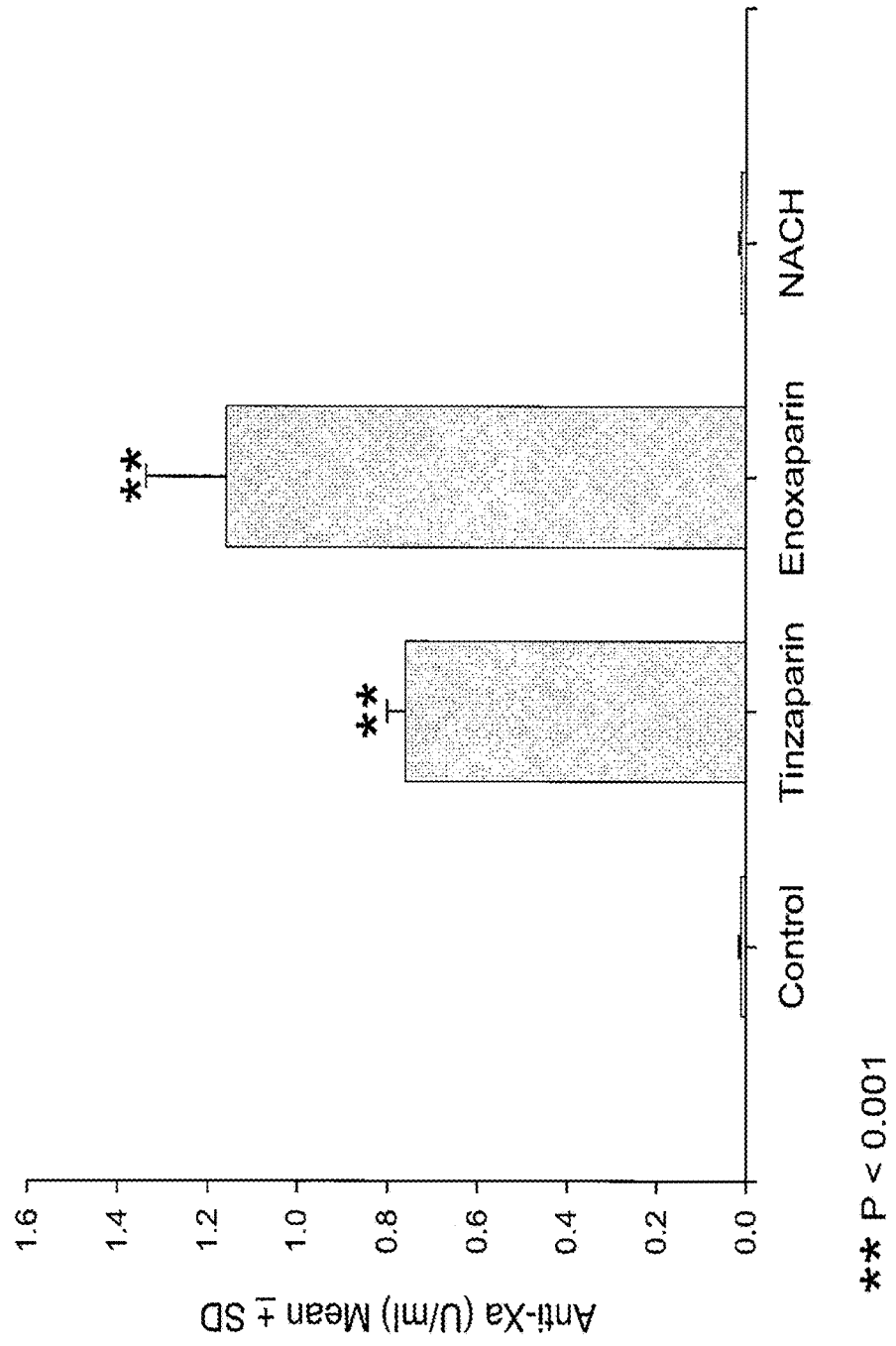
FIG. 4 illustrates the comparative anti-Xa activity for the LMWH tinzaparin and enoxaparin versus NACH as compared to control, in accordance with embodiments of the present invention.

FIG. 4 illustrates the comparative anti-Xa activity for the LMWH tinzaparin and enoxaparin versus NACH including S-NACH or S-SNACH as compared to control, in accordance with embodiments of the present invention. NACH showed no significant effect of factor Xa activity.

EXAMPLE 7

Anti-Factor IIa Assay

The Actichrome Heparin anti-F IIa kit (American Diagnostics Inc., Stamford, Conn.) was run on the same Beckman Coulter ACL8000 coagulation analyzer to analyze the samples. The Actichrome Heparin kit contains Bovine Thrombin Reagent, Human Anti-thrombin III Reagent, and Spectrozyme TH. Each reagent was diluted using $dH_2O$. Heparin binds to anti-thrombin III, which inhibits factor IIa (thrombin), thereby inhibiting the hydrolysis of Spectrozyme TH that would otherwise generate the chromophore. Samples were diluted appropriately to fall within the linear ranges determined by a standard curve, with PBS (pH 7.4) and blank, pooled rabbit plasma. All prepared samples contained 10% plasma. The curve was created based upon the same criteria as the samples (PBS and 10% plasma) using a USP reference standard pharmaceutical grade heparin at concentrations ranging from 0.01-0.80 U/mL.

FIG. 5 illustrates the comparative anti-IIa activity for the LMWH tinzaparin and enoxaparin versus NACH including S-NACH or S-SNACH as compared to control, in accordance with embodiments of the present invention. NACH showed no significant effect of factor IIa activity.

EXAMPLE 8

APTT Assay

Activated Partial Thromboplastin Time (aPTT) is sensitive to all factors in the intrinsic pathway of the coagulation cascade and the presence of heparin. The aPTT was measured for each of the 8 USP heparins, using the ACL 8000 Beckman Coulter coagulation analyzer and the Trinity Biotech Trini CLOT Automated aPTT assay kit (Berkeley Heights, N.J.). Additionally, aPTT was measured for heparin, LMWH, and S-NACH.

Heparin or LMWH increased aPTT in a dose-dependent manner while S-NACH did not show any effect on aPTT.

EXAMPLE 9

Thrombelastography

Thrombelastography (TEG) monitoring of patient hemostasis is based on two facts: the end result of the hemostasis process is a single product that is the clot, and the clot's physical properties (rate, strength, and stability) will determine whether the patient will have normal hemostasis, will hemorrhage, or will develop thrombosis. See Kuderer, N. M., et al., *A meta-analysis and systematic review of the efficacy and safety of anticoagulants as cancer treatment: impact on survival and bleeding complications*, Cancer, 2007, 110(5): p. 1149-61. See van der Bij, G. J., et al., *The perioperative period is an underutilized window of therapeutic opportunity in patients with colorectal cancer*, Ann Surg, 2009, 249(5): p. 727-34. See Islam T, Butler M, Sikkander S A, Toida T, Linhardt R J., *Further evidence that periodate cleavage of heparin occurs primarily through the anti-thrombin binding site*, Carbohydr Res. 2002, 337(21-23):2239-43.

The TEG analyzer (Haemonetics, Braintree, Mass.) measures the clot's physical properties and gives a haemostatic profile that includes the time for the clot to form, the kinetics of the formation, and strength and dissolution data.

Blood was collected from the donor on the day of analysis and analyzed within 4 hours of collection. An IRB-approved method of collection was used. Venous blood was collected in 2.7 mL sodium citrate vacutainer tubes. Typically blood was collected from each donor into three to four sodium citrate tubes either by straight needle or butterfly method, observing good laboratory techniques. The blood samples were kept at room temperature until analyzed. Then, 340 µL of citrated whole blood was added to 20 µL of $CaCl_2$ just prior to analysis on the TEG analyzer. The effect of heparin, LMWH versus S-NACH on platelet/fibrin clot kinetics was compared.

A lack of effect for S-NACH versus the LMWH tinzaparin or enoxaparin on platelet/fibrin clot kinetics (clot strength, time to clot initiation or rate of clot formation) was demonstrated in human blood.

EXAMPLE 10

Coagulation Analysis of Heparins: Enoxaparin (LMWH) vs. NACH

Two heparins, commercial formulation Enoxaparin and non-anticoagulant heparin (NACH) including S-NACH or S-SNACH were evaluated for their effects on coagulation. Whole blood clotting times were measured by the Sonoclot Analyzer (left panel) and by TEG (right panel); n=5. While Enoxaparin significantly prolonged the clot times, NACH effects were not different from control as shown in FIG. 6.

FIG. 6 showed a lack of effect for NACH including S-NACH or S-SNACH as compared to the LMWH enoxaparin on clotting time or time to clot initiation after intravenous administration in mice at 10 mg/kg, each, in accordance with embodiments of the present invention.

EXAMPLE 11

Bleeding Time

Bleeding time in mice was tested during the period of receiving test compounds. Mice were anesthetized with isoflurane inhalation. By using a scalpel, 0.5 cm of the distal end of the tail was transected, and the remaining length of tail was immersed immediately into a 37° C. solution of saline. Bleeding time was measured from the time of tail transection until visible bleeding could no longer be detected. The experiment was repeated 3 times with different groups and concentrations. Mice groups used in the experiment are shown in Table 1.

TABLE 1

Mice groups used in the experiment "Bleeding time" and the doses of test compounds

|  | EXP. 1 | EXP. 2 | EXP. 3 |
|---|---|---|---|
| Groups | 3<br>Control (PBS)<br>LMWH<br>S-SNACH | 3<br>Control (PBS)<br>S-SNACH | 4<br>Control (PBS)<br>LMWH<br>S-SNACH |
| Test compound dose (mg/kg, S.C.) | LMWH (10)<br>S-SNACH (10) | S-SNACH (20) | LMWH (10)<br>S-SNACH (20) |

LMWH (10 mg/kg) doubled the bleeding time (p=0.02) compared to the control group, and S-SNACH (10 mg/kg) had no effect on bleeding time. When the concentration of S-SNACH was increased to 20 mg/kg, there was still no statistically significant increase in bleeding time.

FIG. 7 compares the 3 test compounds (control, LMWH, S-SNACH) for bleeding time in mice, in accordance with embodiments of the present invention. ANOVA analysis showed a difference of 0.002. LMWH doubled the bleeding time (p=0.0001) and S-SNACH had no effect on bleeding time compared to control. Thus, FIG. 7 shows lack of effect for S-SNACH on bleeding time as compared to control, while the LMWH tinzaparin extended the bleeding significantly.

EXAMPLE 12

Chick Chorioallantoic Membrane (CAM) Model

CAM models were used to measure possible effects of angiogenesis and anti-cancer effects. Angiogenesis was measured by counting the number of branch points in blood vessels. PBS was used as a negative control to represent normal growth over time. Growth factor such as b-FGF, VEGF, and other growth factors were used a positive control. Fertilized chicken eggs were incubated at 37° C. with 55% relative humidity for 10 days. In the dark, with the help of a candling lamp and using a hypodermic needle, a small hole was punctured in the shell covering the air sac. A second hole was punctured on the wider side of the egg above an avascular area of the embryonic membrane. An artificial air sac was then created below the second hole by applying gentle vacuum to the first hole using a small rubber squeeze bulb. The vacuum causes the separation of the CAM from the shell. A window of ~1.0 $cm^2$ was cut in the shell over the dropped CAM using a mini-drill, and the underlying CAM was accessed through this window. For the cover slip CAM model, USP heparin, LMWH and S-NACH were evaluated for modulation of angiogenesis. Approximately 8-10 eggs per group were used. On day 11 the cover slips were made up, using b-FGF as a growth factor in addition to the heparin itself. Cover slips were placed and CAMs were incubated for an additional 3 days. On day 14 the cover slips and tissue directly beneath each cover slip were cut from the membrane and washed with PBS. The cover slip and tissue were then placed into a 35 mm petri dish and examined under an SV6 stereomicroscope (Zeiss) at ×50 magnification. Digital images were taken and photographed using Image-Pro Plus software (Media Cybernetics). The number of branch points in the blood vessels within the region of the cover slip was counted, one image for each CAM preparation to analyze each for angiogenesis.

The data showed comparable anti-angiogenesis efficacy for S-NACH as compared to the LMWH tinzaparin regardless of the pro-angiogenesis growth factor used.

EXAMPLE 13

Tumor Growth in the CAM Cancer Implant Model

The CAM cancer implant model has been described previously. See Lim, E., et al., *In vivo bioluminescent imaging of mammary tumors using IVIS spectrum*, J Vis Exp, 2009(26).

The CAM cancer implant model was used in conjunction with the present invention to study the effect of heparin derivatives (S-NACH versus tinzaparin) along with gemcitabine at 1.0 μg/CAM on tumor angiogenesis and tumor growth. MPanc96-luc cells in exponential growth phase were harvested as described above. One$\times 10^6$ cells in 30 μl of medium were mixed with an equal volume of Matrigel and implanted in the chick Chorioallantoic membrane (CAM) model of 7-day old chick eggs. The effect of these treatments was determined after 8 days of implantation. Results are presented as a mean tumor weight (g) per treatment group and tumor hemoglobin (mg/dl)±SEM, n=10 per group. For the Matrigel portions of the models, tumor angiogenesis is evaluated with tumor weight analysis and Drabkin's Assay for hemoglobin concentration (angiogenesis index). PBS was used as a negative control while breast cancer cells were used as a positive control and to initiate tumorigenesis. The tumor cells were MCF-7/DXR (human breast adenocarcinoma), and 1-2 million cells per CAM were used. Matrigel, cells, and heparin solution were placed on the CAM on day 11, however, the CAMs were re-incubated and the tumors were allowed to grow until day 17. On day 17 the tumors were cut from the membrane and placed in pre-weighed sterile microfuge tubes. By re-weighing the tubes with the tumor inside, the weight of the tumor itself could be recorded. After weighing the tubes for tumor weights, the tumors were homogenized in 250-500 μL of dH$_2$O. Specimens were centrifuged, and the hemoglobin content was measured using Drabkin's reagent (Sigma, St Louis, Mo.), run in duplicate using the supernatant.

FIG. 8 depicts NACH including S-NACH or S-SNACH or LMWH inhibition of pancreatic tumor growth and angiogenesis in the Chick Chorioallantoic membrane (CAM)-tumor implant model, in accordance with embodiments of the present invention. Either NACH or the LMWH tinzaparin at 10 ug/CAM inhibited pancreatic (Panc-1) tumor growth or tumor angiogenesis in the CAM model of tumor implant.

FIG. 9 depicts an effect of S-NACH, tinzaparin, and gemcitabine (GEM) on human pancreatic carcinoma, in accordance with embodiments of the present invention. In FIG. 9, Section (A) shows tumor growth and Section (B) shows tumor angiogenesis in the chick CAM cancer cell implant model. S-NACH, tinzaparin, and gemcitabine were added at 1 μg/CAM. Matrigel is a negative control, and all other groups have MPanc96 cancer cells at 1×10$^6$ cells/CAM with or without the test compounds. Data represents mean±SEM, n=10 per group. Significant reductions in tumor size with all agents are evident, *P<0.01.

Either S-NACH or the LMWH tinzaparin at 1.0 ug/CAM maximally inhibited pancreatic (MPanc96) tumor growth or tumor angiogenesis in the CAM model of tumor implant. The anti-cancer efficacy was comparable to Gemcitabine.

Either S-NACH or tinzaparin at 1 μg/CAM significantly (*P<0.01) inhibited pancreatic cancer cell (MPanc96-luc) tumor growth and angiogenesis in the CAM model. Similar to gemcitabine, treatment with either S-NACH or tinzaparin resulted in 60-80% inhibition of tumor growth and tumor angiogenesis, without any significant further increase when combined with gemcitabine.

EXAMPLE 14

Animal Studies

Immune-deficient female NCr nude homozygous mice aged 5-6 weeks weighing 18-20 g were purchased from Harlan Laboratories (Indianapolis, Ind.). All animal studies were conducted in accordance with the institutional guidelines for humane animal treatment. Mice were maintained under specific pathogen-free conditions and housed under controlled conditions of temperature (20-24° C.), humidity (60-70%), and 12 h light/dark cycle with ad libitum access to water and food. Mice were allowed to acclimatize for 5 days prior to the start of study.

EXAMPLE 15

Orthotopic Implant of Breast Cancer Chemo-Resistant Cells (MCF7 DOX Resistant) in Nude Mice Orthotopic implant of 0.5 million of MCF7 DOX resistant cancer cells in nude mice result in progressive rapid tumor growth approaching 150 mm3 after 5 days of implant. Initiation of treatment with S-NACH or the LMWH tinzaparin at 10 mg/Kg, SC daily for 15 days resulted in halting tumor growth progression as compared to control animals (FIG. 10).

FIG. 10 shows immediate response within the first day of treatment in halting tumor growth for either NACH or tinzaparin, in accordance with embodiments of the present invention. Data represent mean tumor volume±SD, n=6 per group.

EXAMPLE 16

Pancreatic Tumor Orthotopic Implant and Treatments

MPanc96-luc cells were harvested as described above and were orthotopically implanted (2×10$^5$ cells in 50 μl PBS per mouse) in the pancreas of anesthetized athymic nude mice. Just before treatment initiation, animals (n=10 per group) were randomized by tumor mass detected by an in vivo imaging system (IVIS, described below). Heparin derivatives S-NACH at 20 mg/kg and tinzaparin at 5 mg/kg were administered subcutaneously daily. Gemcitabine at 100 mg/kg was injected intraperitoneally twice a week alone or in combination with either S-NACH or tinzaparin. All mice used for treatment response evaluations were euthanized after 28 days. See Table 2 for the protocol of the study.

TABLE 2

Treatment schedule of the immune-deficient, female NCr nude mice

| Treatment group | Dosage in mg/kg (administration) | Frequency |
| --- | --- | --- |
| Control | saline (s.c.) | daily |
| S-NACH | 20 (s.c.) | daily |
| tinzaparin | 5 (s.c.) | daily |
| gemcitabine | 100 (i.p.) | twice a week |
| S-NACH + gemcitabine | 20 (s.c.) (S-NACH) | daily |
| | 100 (i.p.) (gemcitabine) | twice a week |
| tinzaparin + gemcitabine | 5 (s.c.) (tinzaparin) | daily |
| | 100 (i.p.) (gemcitabine) | twice a week | s.c. = subcutaneously;
i.p. = intraperitoneally

FIG. 11 depicts an Effect of S-NACH on pancreatic cancer growth 24 hours after orthotopic implant in nude mice, in accordance with embodiments of the present invention. FIG. 11 depicts representative IVIS images of viable cancer cells in the control group and 24 hours after treatment with S-NACH at 20 mg/Kg in pancreatic orthotopic model.

EXAMPLE 17

In Vivo Imaging System (IVIS)

Imaging was performed once per week to monitor tumor growth. Mice bearing MPanc96-luc tumors were anaesthetized using isoflurane, injected subcutaneously with 50 µl D-luciferin (30 mg/ml), then imaged. Photographic and luminescence images were taken at constant exposure time. Xenogen IVIS® Living Image software version 3.2 was used to quantify non-saturated bioluminescence in regions of interest. Light emission between $5.5 \times 10^6$-$7.0 \times 10^{10}$ photons was assumed to be indicative of viable luciferase-labeled tumor cells while emissions below this range were considered as background. Bioluminescence was quantified as photons/second for each region of interest. In vivo tumor kinetic growth and metastasis were monitored by signal intensity. Ex vivo imaging was performed to confirm the signal intensity in the tumors after the termination.

FIG. 12 depicts an effect of S-NACH versus the LMWH tinzaparin on the IVIS signal intensity of pancreatic tumor growth in nude mice, in accordance with embodiments of the present invention. FIG. 12 shows IVIS signal intensity in control, S-NACH, and LMWH tinzaparin treated groups (A) when S-NACH or LMWH were dosed at 10 mg/kg, SC daily, and (B) when S-NACH or LMWH were dosed at 10 and 20 mg/kg, SC daily, respectively. The data shows significant suppression of viable cancer cells by either S-NACH or LMWH.

FIG. 13 depicts an effect of S-NACH versus Tinzaparin with or without on pancreatic tumor growth mice, in accordance with embodiments of the present invention. FIG. 13 shows an effect of S-NACH or tinzaparin and gemcitabine on tumor growth and tumor bioluminescence intensity. Section (A) of FIG. 13 shows bioluminescence images of the excised orthotopic pancreatic tumors of MPanc96 cells bearing luciferase gene after 4 weeks of treatment with S-NACH, tinzaparin, gemcitabine, and combinations. Section (B) of FIG. 13 shows average signal intensity for each treatment showing reduction compared to control. Section (C) of FIG. 13 shows tumor weight at the termination of study. Data represent mean tumor weight (g)±SEM, n=8 per group (A), signal intensity (photons/sec)±SEM. GEM=gemcitabine.

FIG. 13 shows an effect of SNACH versus tinzaparin with or without Gemcitabine on IVIS tumor imaging (A), signal intensity at the end of the study (B), and tumor weight (C).

EXAMPLE 18

Histopathology

All specimens were analyzed by histology for routine analysis. Specimens were fixed in 10% buffered formalin, processed routinely, and embedded in paraffin. Then, after fixation, the specimens were transferred into the embedding chambers to hold the specimens in position until the paraffin became solid to prevent further rotation. Four µm serial sections were cut, and then stained using haematoxylin and eosin. Sections were evaluated for various pathologic parameters using a light microscope (Leica, Buffalo Grove, Ill.).

FIG. 14 depicts an effect of S-NACH versus tinzaparin on pancreatic tumor necrosis, in accordance with embodiments of the present invention. FIG. 14 shows an effect of S-NACH or tinzaparin and gemcitabine on tumor necrosis. Section (A) of FIG. 14 shows representative micrographs of H and E stained histological sections of orthotopic pancreatic tumors showing increased necrotic areas after treatment with S-NACH and tinzaparin compared to untreated tumor with viable cells and large nuclei. Section (B) of FIG. 14 shows histopathological analysis of the orthotopic pancreatic tumors of MPanc96 cells treated with S-NACH showed significant increase in necrotic areas compared to untreated tumors (*$P<0.05$, **$P<0.01$). GEM=gemcitabine.

Tumors showed strong bioluminescent signal intensities with increasing size over time. Treatment with S-NACH (20 mg/kg body weight) and tinzaparin (5 mg/kg body weight) was started 2 days after MPanc96-luc cell implantation in the pancreas. In in a preliminary study, use of a higher concentration of tinzaparin (10 mg/kg) caused severe bleeding at the site of the injection, and hence, in the current study, the tinzaparin dose was adjusted to 5 mg/kg. Daily treatment of orthotopic pancreatic tumors resulted in suppression of tumor signal intensity as determined by IVIS. Repeated administration resulted in sustained inhibition of luciferin signal strength. However, in the control group, tumor luminescence increased and expanded an indication of metastasis, shown in open-cavity imaging of representative mice or ex vivo imaging of excised tumors from mice. Common sites of distant metastasis in the control group were the liver, peritoneum, abdominal lymph nodes, bones, kidneys, and the small and large intestine.

Gemcitabine, alone or in combination with heparin derivatives, reduced luciferin signal intensity and tumor weights, shown at 28 days following initiation of MPanc96-luc cell pancreatic tumors. However, divergent patterns emerged with respect to tumor signal intensity and tumor weights in certain treatment groups. Of particular interest was that tumor luciferin intensity was significantly decreased in S-NACH and S-NACH+ gemcitabine groups, while tumor weights were only moderately decreased in comparison to gemcitabine alone at the end of the study. In comparison to the untreated controls, S-NACH and tinzaparin treatments resulted in only 25-30% inhibition of tumor mass. However, signal intensity of tumors showed a highly significant decrease in the S-NACH treated groups when compared to other treatments and controls. Gemcitabine-treated animals developed smaller tumors (tumor weights), but the tumor signal intensity was significantly higher than that in S-NACH (+/− gemcitabine) groups. These treatments caused no decreases in animal body weights (data not shown), which is an index of the lack of toxicity of compounds.

To address the discrepancies between tumor bioluminescence indices and tumor weights and to investigate possible mechanisms involved in the divergent patterns, histological analyses of tumors were performed from all treatment groups (FIG. 14, section A). Histology showed that untreated animals have high-grade (anaplastic) features as common to advanced stage pancreatic cancer. S-NACH treated tumors showed large regions of necrosis (P<0.01) when compared to other treated groups (FIG. 14, section B). In contrast, tinzaparin treatment resulted in modest increase in necrotic area as compared to S-NACH (FIG. 14, section B). Necrotic areas included both early stage (fragmented and small nucleus) and late stage (ghost cells without nucleus) areas indicating that S-NACH had effects on early and later aspects of cell death. Tumor necrosis induced by S-NACH was inversely proportional to the bioluminescent signal in the tumor, since only live cells show bioluminescent signal. Even at low concentration (5 mg/kg body weight), tinzaparin-treated animals showed a high percentage of hemorrhage and bleeding in the tumor and lymph nodes.

EXAMPLE 19

Liver Metastasis after Splenic Injection of Tumor Cells

Mice were randomly distributed into control and treatment groups (average 9 mice per group). The mice were anesthetized with isoflurane by inhalation and received S.C. injection of the test compounds according to the group (LMWH, SNACH or PBS). Thirty minutes later a left lateral abdominal incision was made to expose the spleen. One million Mpanc96-luc cells (suspended in 30 ul media) were slowly injected into the spleen. The animals received daily subcutaneous (S.C.) injections of the test compounds and were euthanized after 2 or 4 weeks; two trials of this experiment were done (Table 3). IVIS images were taken once per week and the images of the last day of the experiment were used to evaluate the extent of metastasis.

TABLE 3

Mice groups used in the experiment "splenic injection of tumor cells" and the doses of the test compounds.

|  | EXP. 1 | EXP. 2 |
|---|---|---|
| Groups | Control (PBS) LMWH S-SNACH | Control (PBS) LMWH S-SNACH |
| Test compound doses (mg/kg, S.C.) | LMWH (10) S-SNACH (10) | LMWH (10) S-SNACH (20) |
| Treatment duration (weeks) | 4 | 2 |

FIG. 15 compares tumor metastasis to the liver after injecting cancer cells into the spleen (LMWH vs. S-NACH), in accordance with embodiments of the present invention. FIG. 15: shows an effect of S-NACH versus the LMWH tinzaparin on pancreatic cancer (MPanc96) metastasis into the liver after its injection in the spleen. He data shows significant inhibition of liver metastasis by S-NACH.

For liver metastasis after splenic injection of tumor cells, in the first trial of the experiment, the control, LMWH, and SNACH were compared, with the tumor metastasis of cancer cells from spleen to liver significantly inhibited; results are shown (p=0.03). It shows that both groups of LMWH and S-SNACH had less light intensity of metastasized cancer cells compared to control group. In the second trial of the experiment the control, LMWH, and S-SNACH were compared. A statistically significant inhibition to the liver compared to control (ANOVA analysis p=0.01) was shown. There was no statistically significant difference in effectiveness among the test compounds compared to each other. There were 0 animal deaths in the SNACH group but 4 deaths (44%) in the LMWH group, most probably because of internal bleeding after the surgery. This showed that SNACH is safer as compared to LMWH.

EXAMPLE 20

Liver Metastasis after Excision of Pancreatic Cancer

Mice were randomly distributed into control and treatment groups, averaging 10 mice in each group. Mice were anesthetized and a small left abdominal incision was made. A half million Mpanc96-luc cancer cells (suspended in 30 ul of media) were injected sub-capsularly into the pancreatic tail, and the abdomen was closed by surgical clips. One week later, the mice underwent another laparotomy to excise the pancreatic cancer. The mice received the test compounds (LMWH, SNACH or PBS) 30 minutes before the second surgery and daily after that for 3 weeks (Table 4). The spread of cancer cells was monitored using IVIS imaging once per week, and at the end of the 3 week treatment period the mice were euthanized.

TABLE 4

Mice groups used in the experiment "pancreatic cancer excision" and the doses of the test compounds.

|  | EXP. 1 | EXP. 2 |
|---|---|---|
| Groups | Control (PBS) LMWH S-SNACH | Control (PBS) LMWH S-SNACH |
| Test compound dose (mg/kg, S.C.) | LMWH (10) S-SNACH (10) | LMWH (10) S-SNACH (20) |
| Treatment duration (weeks) | 3 | 3 |

FIG. 16 compares tumor relapse after surgical excision of pancreatic cancer liver metastasis after excision of pancreatic cancer, in accordance with embodiments of the present invention. In FIG. 16, S-NACH but not tinzaparin resulted in significant suppression of tumor recurrence after surgical excision of pancreatic tumor.

In this experiment, LMWH was compared to S-SNACH in their efficacy in inhibiting surgically induced metastasis. The test compounds showed decreased metastasis to liver after pancreatic cancer excision, but it was not statistically significant (p=0.2047). However the test compounds were able to decrease the recurrence of local tumor after surgery (p=0.0307).

In the second experiment, a higher concentration of S-SNACH (20 mg/kg) was used. Although the results were not statistically significant (p=0.08), it showed a proportional decrease in tumor recurrence and metastasis. The percentile death of mice was high in the LMWH group and reached 6 animals (50%) at the end of the experiment due to internal bleeding after two invasive surgeries. At the end of all experiments, the percentile death among all groups was calculated and compared.

EXAMPLE 21

Quantitation of Metastasis into the Lung Using IVIS Imaging

Tumor metastasis into the lung is a common finding when the cancer cell spread into the blood stream, which can be measured using microscopic examination or in vivo imaging system (IVIS). See Amirkhosravi, A., et al., *Assessment of anti-metastatic effects of anticoagulant and antiplatelet agents using animal models of experimental lung metastasis*, Methods Mol Biol, 2010, 663: p. 241-59. See Lim, E., et al., *In vivo bioluminescent imaging of mammary tumors using IVIS spectrum*, J Vis Exp, 2009 (26).

In vivo tumor kinetic growth and metastasis were monitored by signal intensity. Ex vivo imaging was performed to confirm the signal intensity in the tumors after the termination of the study. Mice were anesthetized and received luciferin injections subcutaneously. Photographic and luminescence images were taken at constant exposure time. Xenogen IVIS living image software (version 3.2) was used to quantify non-saturated bioluminescence in regions of interest (ROI). Light emission between $5.5 \times 10^6$ and $7.0 \times 10^{10}$ was assumed to be indicative of viable luciferase-labeled tumor cells while emission below this range was considered as background. Bioluminescence was quantified as photons/second for each ROI.

FIG. 17 depicts an anti-metastatic effect of S-NACH into the lung of nude mice, in accordance with embodiments of the present invention. FIG. 17 shows an anti-metastatic effect of S-NACH on pancreatic cancer lung metastasis as assessed by IVIS imaging for signal intensity and microscopic and histological examination.

EXAMPLE 22

Molecular Studies of Cultured Pancreatic Cell Growth In Vitro

Cells were cultured using 10% fetal bovine serum throughout the course of each study. Media were replenished daily, including the addition of the LMWH tinzaparin or S-NACH at 40 µg. For immunoblotting, extracts of cytosolic proteins were obtained from control and treated cells, after which the total protein content was quantitated and proteins resolved on discontinuous PAGE. Proteins were then electro-blotted to nitrocellulose membranes (Millipore, Bedford, Mass.) as previously described. The membranes were treated with 5% milk in tris-buffered saline containing 0.1% Tween™ and incubated overnight with one of the following: monoclonal anti-pSer15-p53, anti-XIAP, anti-THBS1, anti-P21, or anti-Caspase-2. Primary antibody incubation was followed by treatment with the secondary rabbit anti-mouse IgG antibody. Immunoblots of β-actin were also prepared to control for equalization of proteins. Results are presented in FIG. 18.

FIG. 18 depicts molecular effects of NACH versus LMWH in human pancreatic cancer, in accordance with embodiments of the present invention. FIG. 18 shows effects of LMWH and NACH on abundance of apoptosis and angiogenesis-related proteins in MPanc96 cells in vitro. Cells were cultured for 72 h in the presence of vehicle (PBS), LMWH, or NACH (40 µg). Immunoblots of total proteins harvested from the samples were prepared. Increased accumulation of thrombospondin-1 protein was obtained with NACH or LMWH (*P<0.05). Either NACH or LMWH increased expression of p53 mRNAs (*P<0.05). P21 protein levels were significantly (*P<0.05) increased by NACH but not by LMWH. Either NACH or LMWH significantly decreased accumulation of XIAP (P<0.01). β-actin was used as an internal control. Data represent mean±SEM, n=3 (*P<0.05 and **P<0.01).

The effects of LMWH and NACH on the abundance of proteins relevant to angiogenesis and apoptosis were examined in MPanc96 pancreatic cancer cells treated with either LMWH or NACH at 40 µg. Thrombospondin-1 (THBS1) is an endogenous anti-angiogenesis protein, which shows reduced gene expression in cancer cells. The abundance of THBS1 protein was increased 1.5-2 fold by NACH (P<0.05), with a similar trend for tinzaparin. Data also showed that cellular abundance of p53, p21, and Caspase-2 increased above control levels, with statistical significance (P<0.05) in p53 with the NACH and LMWH treatment groups. A significant increase in P21 protein above control was observed with NACH (P<0.05) but not with LMWH (FIG. 5). Both NACH and LMWH significantly increased Caspase-2 (P<0.05). In further support for the promotion of apoptosis by NACH and LMWH, X-linked inhibitor of apoptosis protein (XIAP) was significantly suppressed by either LMWH or NACH (P<0.01).

Data demonstrated for the first time that S-NACH has a direct effect on the survival of pancreatic cancer tumor cells in vivo. S-NACH treatments resulted in effective inhibition of pancreatic tumor growth and angiogenesis in the CAM model, consistent with its effects on other tumors. The in vivo data showed that S-NACH inhibits metastasis of pancreatic cancer as demonstrated by the complete absence of bioluminescent signals when internal organs were exposed after the termination of study. In contrast, the untreated control group showed extensive metastasis into multiple organs. The absence of bioluminescence associated with live cells in the S-NACH treatment groups was confirmed by data showing the corresponding increase (~50%) of necrosis in histological studies. The anti-angiogenesis and anti-metastatic activity of S-NACH may be due, at least in part, to the tissue factor pathway inhibitor protein release from endothelial cells, similar to effects demonstrated for LMWH Enoxaparin. Our data clearly demonstrate that S-NACH, without any systemic anticoagulant effects, possesses equivalent or better anti-cancer efficacy in comparison to tinzaparin. S-NACH at a high dose (20 mg/kg body weight) had no systemic anti-coagulation effects in mice; however, tinzaparin (5 mg/kg body weight) increased bleeding, evident in the histological sections of tumor and lymph.

Experiments using either S-NACH or tinzaparin+gemcitabine in animal models indicate significantly enhanced chemotherapeutic response of the pancreatic tumors as shown by reduced luminescent signal intensity with increased necrotic areas when compared to gemcitabine treatment alone. In that study S-NACH significantly increased the uptake of chemotherapeutic agents in addition to suppressing tumor growth and significantly prolonged survival. S-NACH has been shown to inhibit platelet-associated P-selectin dependent processes in a manner similar to other glycosaminoglycans. The results herein indicate that S-NACH can be utilized in chemotherapy combinations to improve chemo responsiveness. Thus, the increased uptake of gemcitabine, if comparable to what was seen with Paclitaxel and Doxorubicin, may allow for reduction of gemcitabine dose, with a decrease in concomitant toxicities. In addition, heparin compounds might impact on P-glycoprotein and associated pump activity, one of the main drug resistant mechanisms, suggesting that S-NACH may also potentially overcome gemcitabine chemo-resistance.

Data also shows direct effect of NACH and LMWH on the induction of anti-angiogenesis protein THBS1 and pro-apoptosis proteins P53, P21, and Caspase-2, while suppressing the anti-apoptosis protein XIAP in MPanc96 cells. These data suggest direct effects of heparin on cancer cells that are independent of its anticoagulant activity.

S-NACH, the non-anticoagulant heparin, is preferable for potential clinical use because of the possibility that it could be administered at high doses, thereby fully exploiting the anti-cancer and anti-metastatic components of heparin. S-NACH could have a broader application because it could be utilized, either alone or in combination with chemotherapeutic agents, to treat pancreatic cancer or other cancers that are associated with their own bleeding complications.

EXAMPLE 23

Effect of S-NACH Versus LMWH Tinzaparin on Pancreatic Tumor (SUITE2)

Cell line: SUITE2-Luc-RFP
Animals: Female nude mice
Site of injection: Orthotopic, pancreases
Treatment for 21 days
Treatment groups: Control; GEM (100 mg/kg) twice a week; S-NACH (20 mg/kg); Tinzaparin (5 mg/kg); S-NACH+GEM; Tinzaparin+GEM FIG. 19 depicts an effect of S-NACH versus LMWH Tinzaparin on orthotopically implanted pancreatic tumor (SUITE2) in nude mice after 21 days of treatment, in accordance with embodiments of the present invention.

EXAMPLE 24

Anti-Tumor Efficacy of Nanoparticle Formulations Encapsulating Doxorubicin (Dox) with and without LMWHs Vs. Un-Encapsulated Dox in Mice with MCF7-WT Tumors Mice were inoculated with $1.4 \times 10^7$ MCF7-WT cells. Treatments were begun 10 days after tumor cell inoculation as shown in legend. Tumor volume measurements were obtained over time course shown. Values are mean tumor volume in mm³±SEM, n=8 mice/group. In Control (untreated) group and in animals treated with void nanoparticles, tumors continued to increase in volume. As expected, un-encapsulated Dox effectively inhibited this Dox-sensitive tumor. However, Nano-Dox or $\alpha v\beta 3$-targeted Nano-Dox treatments show similar patterns of inhibition and appeared to be more effective in inhibiting tumor growth than un-encapsulated Dox (p<0.05) over the tumor growth period encompassing 5-15 days. Targeted Nano-Dox particles containing either LMWH or NACH showed similar levels and patterns of inhibition to that of Nano-Dox treatments. With respect to hemostasis, nanoparticles that contained LMWH Enoxaparin, but not NACH, caused bruising at the site of injection.

Encapsulation of Dox, whether in targeted or non-targeted nanoparticles improved anti-tumor efficacy in comparison to un-encapsulated Dox. In this initial experiment, all nano-formulations showed similar patterns of inhibition with no significant statistical differences from each other in the nanoformulations treatment groups. Future studies will investigate long-term effects of these treatments on survival and tumor growth and will evaluate whether there are differences in the efficacies of LMWH- or NACH-containing nanoparticles.

Figure 20:
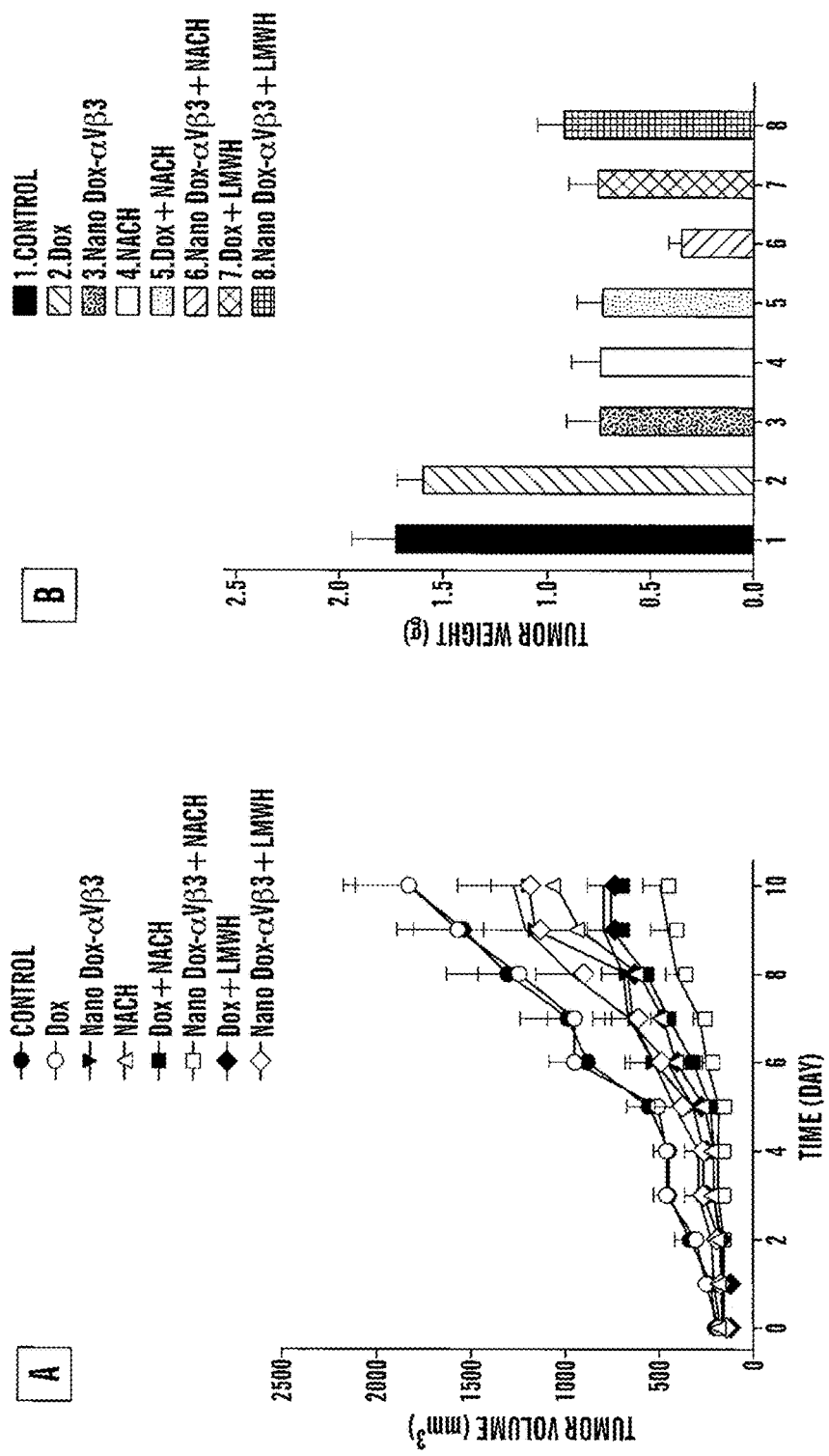
FIG. 20 depicts anti-tumor efficacy of nanoparticle formulations encapsulating Doxorubicin with and without LMWHs vs. un-encapsulated Doxorubicin in mice with MCF7-R Tumors, in accordance with embodiments of the present invention.

FIG. 20 depicts anti-tumor efficacy of nanoparticle formulations encapsulating Doxorubicin with and without LMWHs vs. un-encapsulated Doxorubicin in mice with MCF7-R Tumors, in accordance with embodiments of the present invention. FIG. 20 shows anti-tumor efficacy of nanoparticle formulations encapsulating Dox with and without LMWHs vs. un-encapsulated Dox in mice with MCF7-R Tumors: Mice (8/group) were inoculated with $3 \times 10^6$ MCF7-R cells. Treatments, as shown in legend, were begun after tumors had reached a size of 50-100 mm³. Tumor volumes were measured daily. Animals were euthanized when Controls reached a size of 2000 mm³ (as per IACUC approval).

In FIG. 20, Panel A illustrates the effects of treatments on tumor volume over time. Dox-treated animals showed the same pattern of tumor growth as untreated controls, as expected with this Dox-resistant tumor. Encapsulation of Dox in a $\alpha v\beta 3$-targeted nanoparticle (closed triangle) significantly improved the anti-tumor efficacy of Dox in these Dox-resistant tumors. Further, substantial inhibition was observed with NACH (open triangles), Dox+NACH (closed squares), and Dox+LMWH (closed diamonds) groups, even without encapsulation in nanoparticles, suggesting that LMWH or NACH can improve the anti-tumor activity of Dox, even in a drug-resistant tumor. One possible mechanism that could be involved in this effect is discussed below in studies of LMWH and chemotherapeutic uptake (FIG. 10). The most effective anti-tumor agent was $\alpha v\beta 3$-targeted Dox+NACH nanoparticle treatment that was responsible for slowing tumor growth rate and limiting tumor size.

In FIG. 20, Panel B illustrates tumor weights measured after animals were euthanized. All treatment groups were superior to Dox treatment alone (p<0.001), and the pattern of inhibition paralleled that observed with the tumor growth curves in Panel A. Treatment group 6, $v\beta 3$-targeted Dox+NACH showed inhibition that was significantly different from all treatment groups, p value vs. other groups was at least <0.02.

These studies demonstrate that encapsulating Dox in $\alpha v\beta 3$-targeted nanoparticles or administering it with NACH represent potent strategies for overcoming Dox-resistance in animals bearing aggressive chem0-resistant human breast tumor. In future studies, these studies will be expanded and repeated to optimize dosing regimens and drug concentrations.

PLGA-PEG nanoparticles co-encapsulating NACH and doxorubicin were synthesized by double emulsion solvent evaporation method. The in vitro efficacy of these nanoparticles was examined in MCF-7 doxorubicin resistant (MCF-7R) cells by cell viability (MTT) assay. Confocal microscopy was used to examine the uptake of alpha$_v$beta$_3$ antibody conjugated nanoparticles in human dermal microvascular endothelial cells (HDMEC), which are known to over express alpha$_v$beta$_3$ integrin.

Size measurement by DLS revealed these nanoparticles co-encapsulating doxorubicin and heparins to be >300 nm. Data from the MTT assays in MCF-7R cells are shown Table 4. In vivo data using in mice xenograft (MCF-7R) are shown in Table 5 (amounts of doxorubicin and NACH injected in all cases were 0.625 mg/kg and 2.5 mg/kg body weight).

TABLE 5

Effect Integrin Targeted Nanoformulation on Tumor Growth of MCF7 Doxorubicin Resistant

| Formulation | Tumor Mass (g) | ±SEM |
| --- | --- | --- |
| Control | 1.5 | 0.4 |
| Void Nanoparticles | 1.9 | 0.5 |
| Doxorubicin | 1.3 | 0.2 |
| NANO-(Doxorubicin) | 1.2 | 0.1 |
| Nano-(Doxorubicin)-$\alpha_v\beta_3$ | 0.8 | 0.1* |
| Nano-(NACH + Doxorubicin)-$\alpha_v\beta_3$ | 0.5 | 0.2* |

NACH includes S-NACH or S-SNACH,
*P < 0.01

PLGA-PEG nanoformulations co-encapsulating NACH including S-NACH or S-SNACH and doxorubicin exhibit superior in vitro efficacy compared to non-encapsulated drugs in the MCF-7R cell line. Confocal imaging in HDMEC cells indicates that these nanoparticles have the potential to be used for site specific delivery to the tumor neovascularization; these findings were later supported by in vivo data. Significant decrease in tumor weight was observed in the mice (MCF-7R), when treated with $\alpha v\beta 3$ conjugated nanoparticles co-encapsulating doxorubicin and NACH compared to its non-encapsulated counterpart.

EXAMPLE 25

HPLC Determination of Doxorubicin in Tissue and Tumors of Mice Bearing MCF7-R Xenograft Treated with LMWH or NACH To determine whether LMWH compounds increase the uptake of chemotherapeutic agents into tumors, mice were pre-treated with 10 mg/kg of LMWH or NACH including S-NACH or S-SNACH for 5 days followed by DOX (2.5 mg/kg). Three or 24 hours later, animals were euthanized and tissues obtained for HPLC determination of DOX. Calibration curves were generated from DOX spiked into blank tumor tissue and extracted with solvent (Methanol: Chloroform, 1:4). Both LMWH and NACH significantly increased the uptake of chemotherapeutic agent DOX in MCF7 Doxorubicin-resistant tumors by 1.5-2 fold but not in heart or lung tissues (*p<0.01). These findings confirm data previously obtained by us with another chemotherapeutic agent [124-I]-Paclitaxel in an aggressive human lung tumor LCC6. In that study there was a constant positive enhancement effect between controls and heparin groups, with at least a two-fold (100%) increase in tumor to muscle ratio. This is a highly significant result in the light of the fact that the FDA criterion for a clinically meaningful effect is a 15% increase in uptake.

Figure 21:
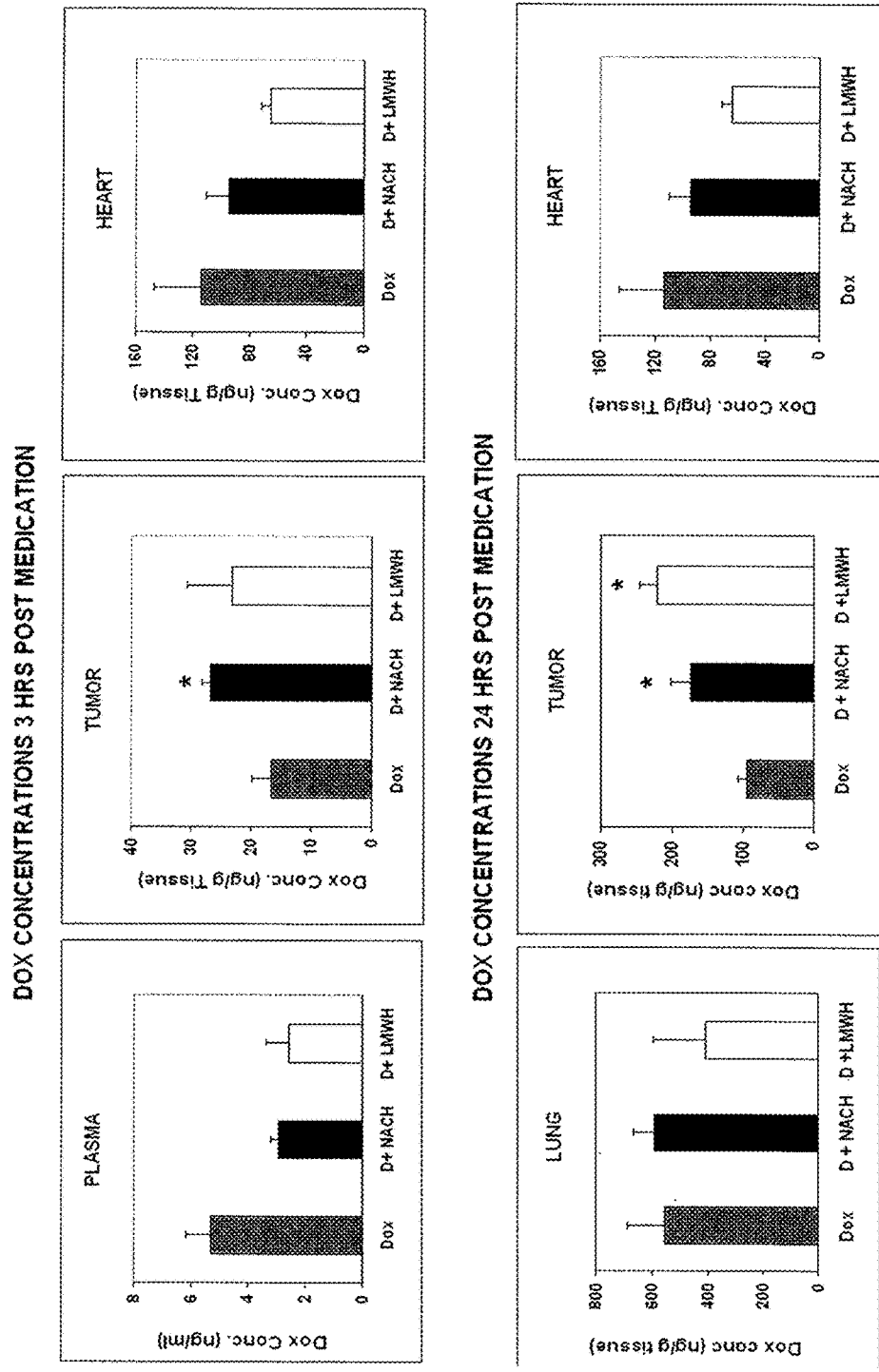
FIG. 21 depicts HPLC determination of Doxorubicin in tissue and tumors of mice bearing MCF7-R Xenograft and treated with LMWH or NACH, in accordance with embodiments of the present invention.

FIG. 21 depicts HPLC determination of Doxorubicin in tissue and tumors of mice bearing MCF7-R Xenograft and treated with LMWH or NACH, in accordance with embodiments of the present invention.

EXAMPLE 26

Effect of S-NACH Versus LMWH on Bladder Cancer Cells: Four Bladder Cancer Cell Lines 253JB-V Bladder cancer 253JB-V cells were orthotopically implanted into athymic male mice.

Figure 22:
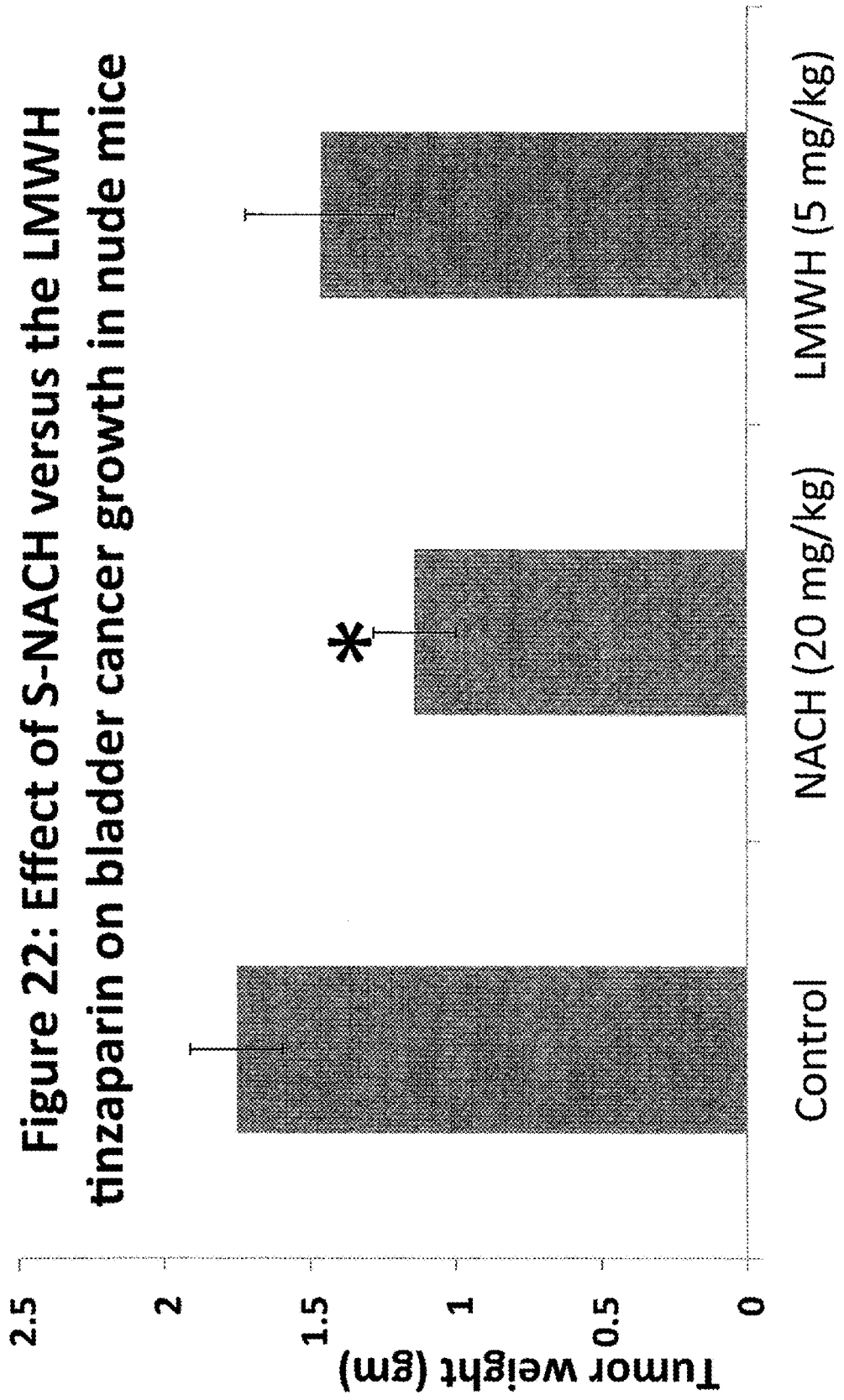
FIG. 22 shows an effect of SNACH versus the LMWH tinzaparin on bladder cancer growth in nude mice, in accordance with embodiments of the present invention.

FIG. 22 shows an effect of S-NACH versus the LMWH tinzaparin on bladder cancer growth in nude mice, in accordance with embodiments of the present invention.

EXAMPLE 27

Figure 23:
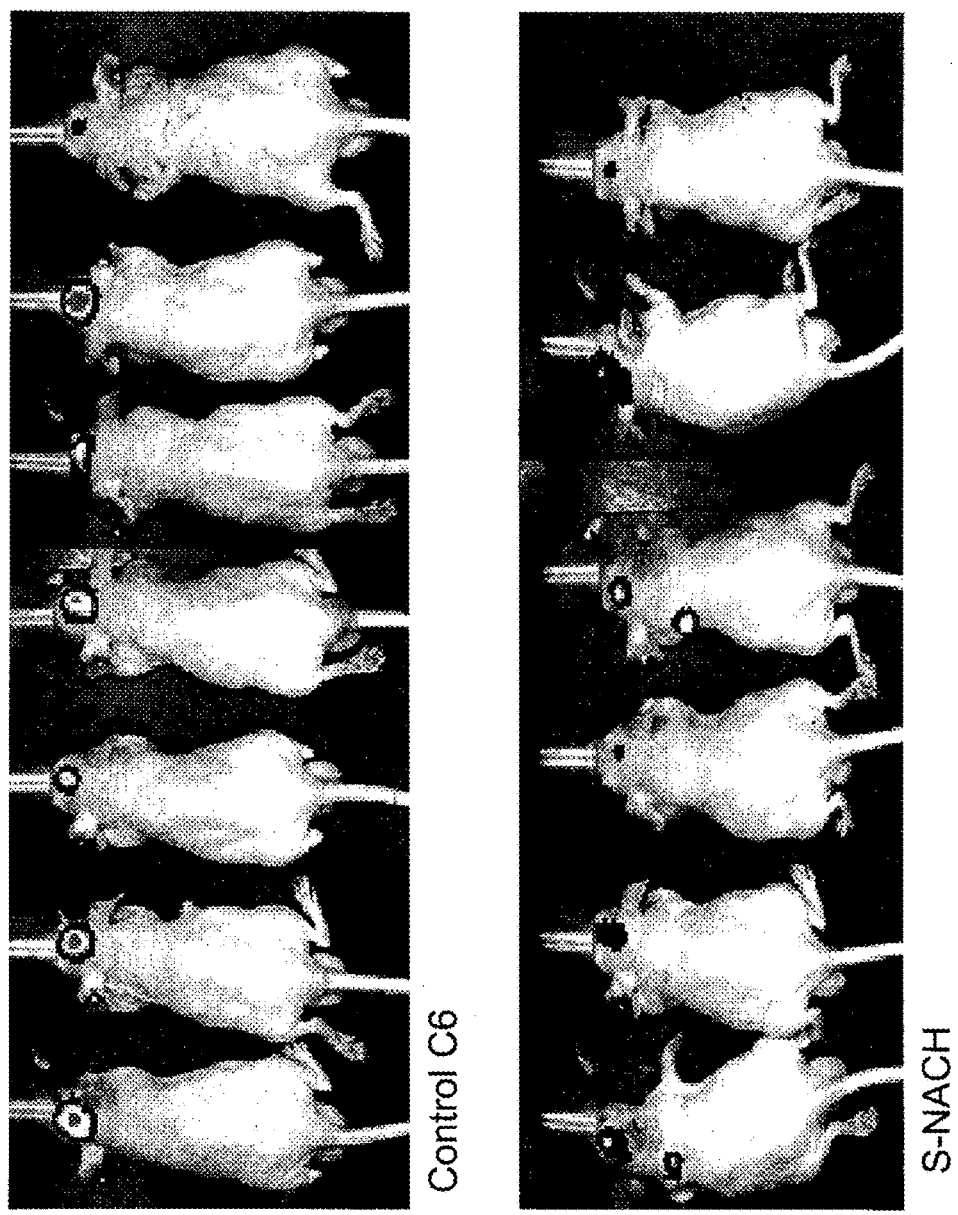
FIG. 23 depicts an effect of NACH on glioma tumor growth in nude mice using IVIS imaging, in accordance with embodiments of the present invention.

Effect of S-NACH on Glioma Cancer Cells C6: C6 Cells were Orthotopically Implanted into Athymic Male Mice FIG. 23 depicts an effect of NACH on glioma tumor growth in nude mice using IVIS imaging, in accordance with embodiments of the present invention.

EXAMPLE 28

Effect of Cisplatin, s-NACH and LMWH on the Expression of E-Cadherin, Activated p38 & Matrix Metalloproteinase (MMP-2) Proteins of Bladder Cancer Cells 253JBV bladder cells were cultured and treated [Control (PBS), Cisplatin (10 ug/ml), S-NACH (20 ug/ml), LMWH (20 ug/ml)] for 48 hour. Total proteins were collected to quantitate expression of the proteins using western blots.

Figure 24:
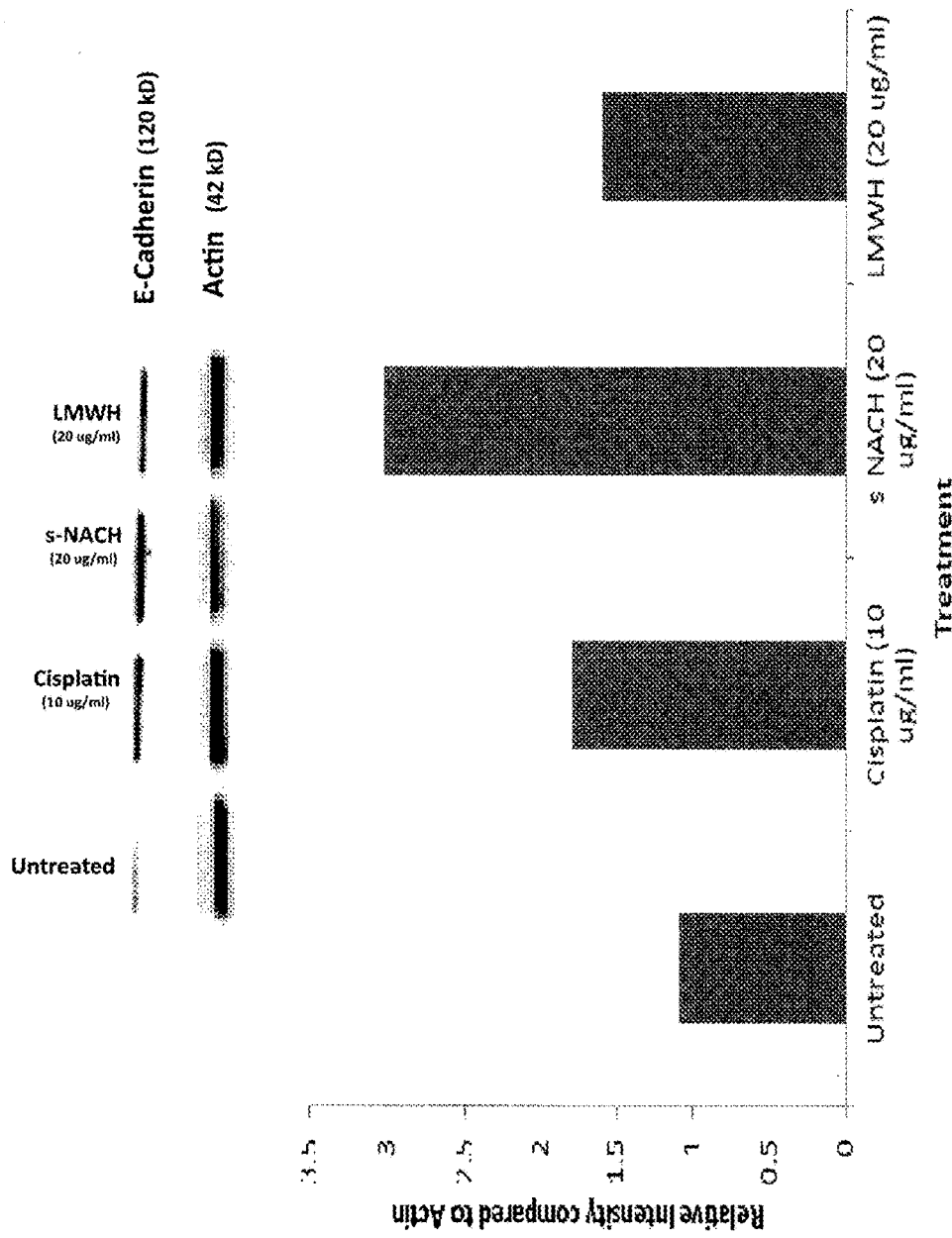
FIG. 24 shows S-NACH, Cisplatin and LMWH increased E-cadherin protein expression of bladder cancer cells (253JBV), in accordance with embodiments of the present invention.

FIG. 24 shows S-NACH, Cisplatin and LMWH increased E-cadherin protein expression of bladder cancer cells (253JBV), in accordance with embodiments of the present invention.

Figure 25:
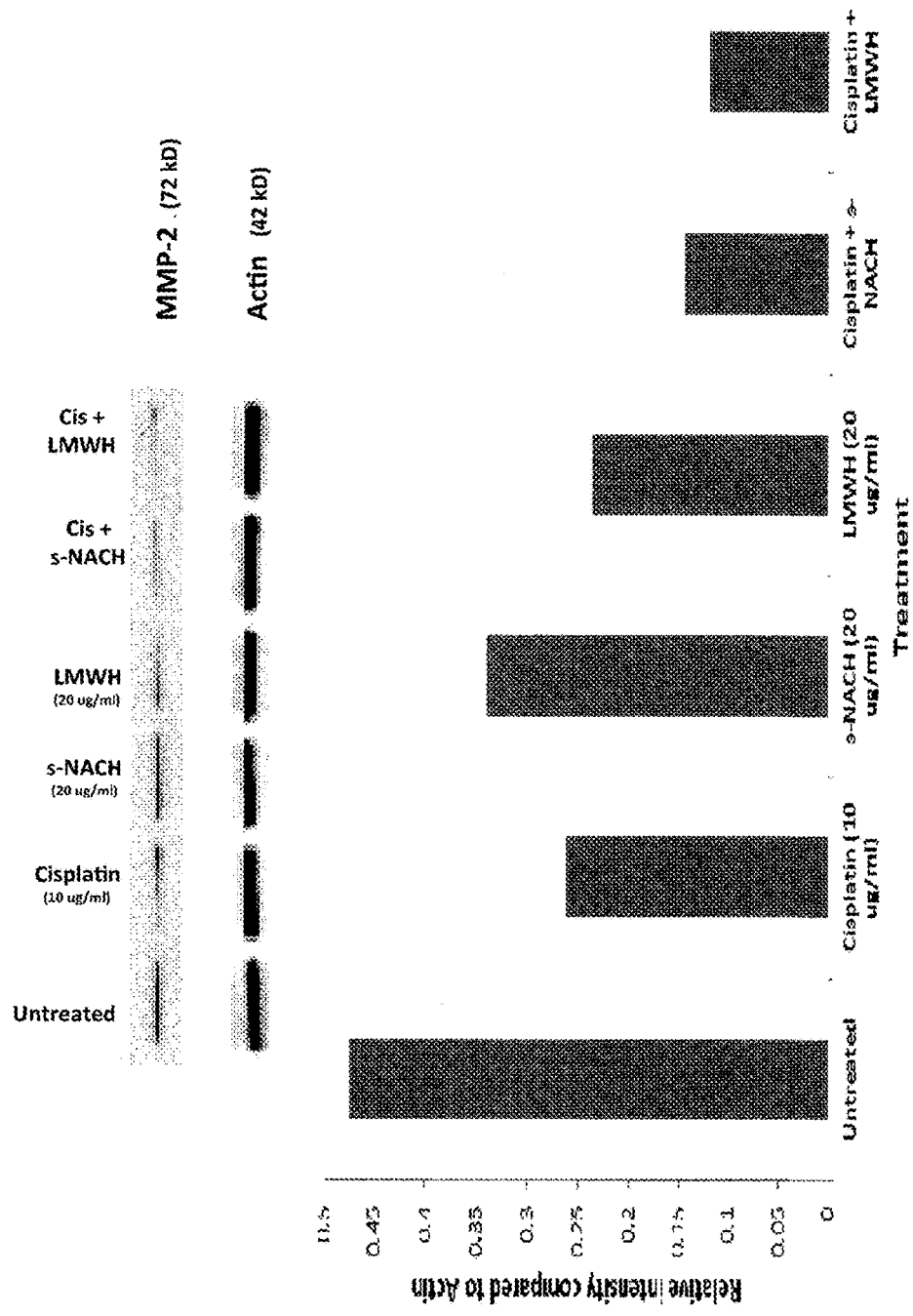
FIG. 25 shows S-NACH, Cisplatin and LMWH reduced MMP-2 protein expression of bladder cancer cells (253JBV) 5: MMP-2, in accordance with embodiments of the present invention.

FIG. 25 shows S-NACH, Cisplatin and LMWH reduced MMP-2 protein expression of bladder cancer cells (253JBV) 5: MMP-2, in accordance with embodiments of the present invention.

EXAMPLE 29

Effect of S-NACH Versus Tinzaparin on P-Selectin Expression

Figure 26:
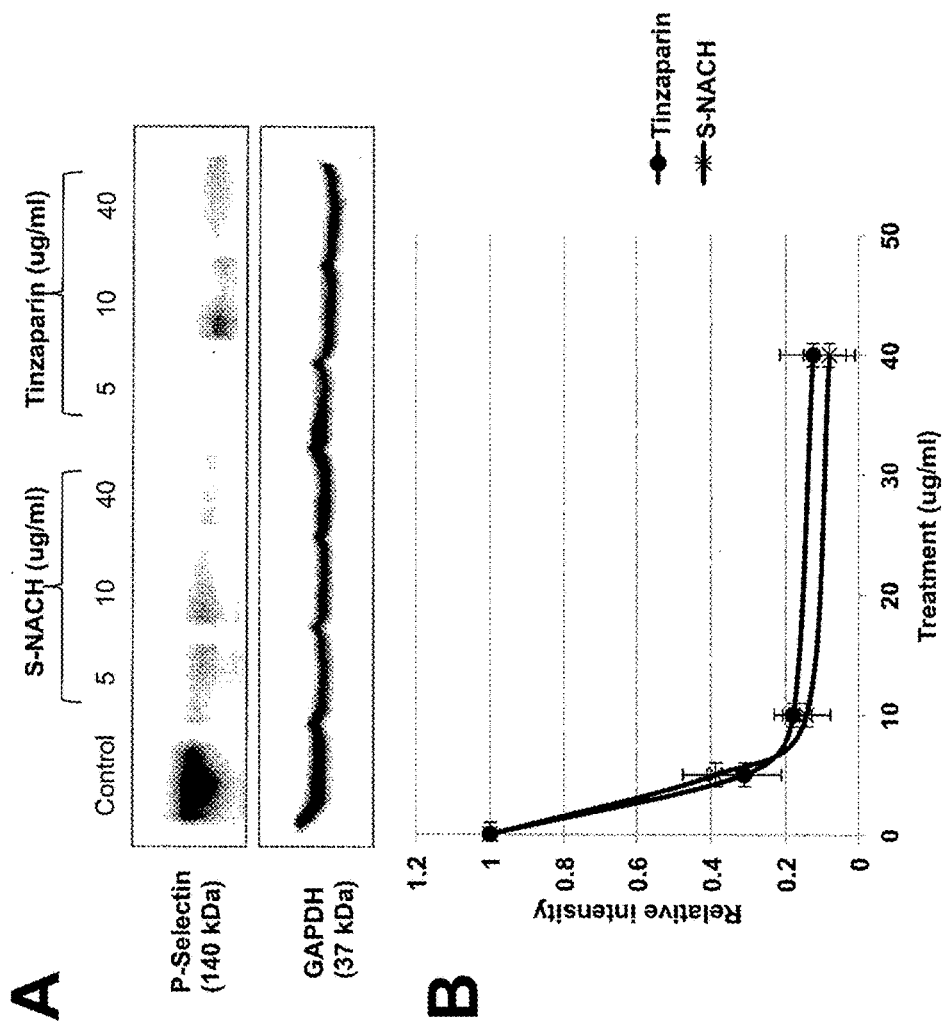
FIG. 26 depicts an effect of S-NACH versus Tinzaparin on P-Selectin expression), in accordance with embodiments of the present invention.

FIG. 26 depicts an effect of S-NACH versus Tinzaparin on P-Selectin expression, in accordance with embodiments of the present invention.

EXAMPLE 30 qPRC Studies of microRNA of MDA-MB-231 Cells

Cells are incubated in serum free medium before treatment with (a) Vehicle PBS or (b) S-NACH (40 ug/ml). MicroRNA was isolated and qPCR study carried out using MiR-21 and MiR-15A primers (Qiagen). S-NACH effect: Micro RNA 21 is over expressed in MDAMB-231 and Micro RNA 15A is down regulated.

Figure 27:
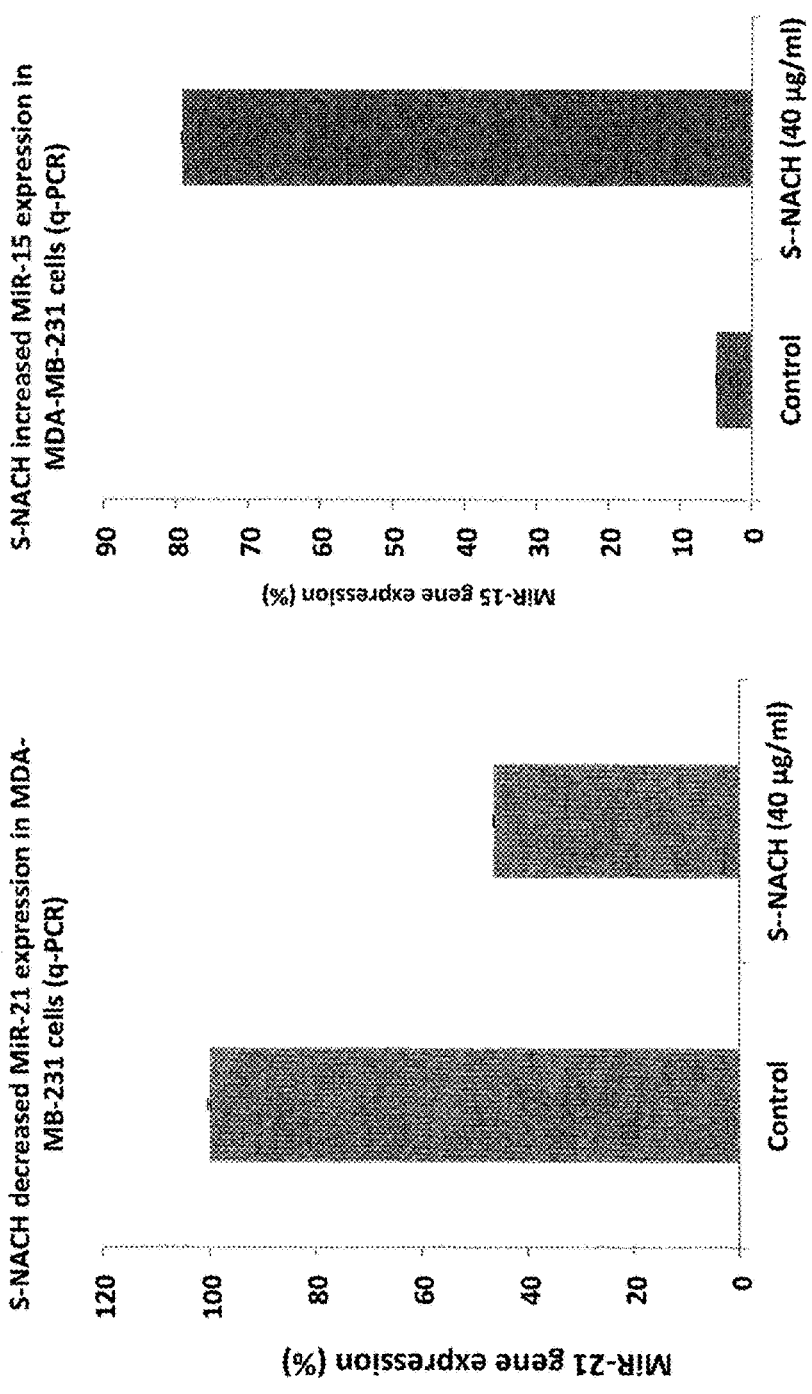
FIG. 27 provides a characterization of SNACH, in accordance with embodiments of the present invention.

FIG. 27 shows an effect of S-NACH on Micro RNA, in accordance with embodiments of the present invention where S-NACH upregulated tumor suppressor mRNA15A and downregulated tumor promoter mRNA 21.

EXAMPLE 31

Nanoformulation of S-NACH Co-Encapsulated with Chemotherapy

Untargeted nanoparticles (NPs) will have encapsulated S-NACH±Gemcitabine (Gem). The synthesis a nanoparticulate system made up of a blend of MPEG-PLGA (methoxypolyethylene glycol-poly (lactide-co-glycolide) and maleimide-PEG-PLGA. These NPs are prepared by double emulsion/solvent evaporation methods. PEG-PLGA, maleimide-PEG-PLGA NPs are capable of encapsulation of S-NACH or other LMWH, various chemotherapeutic agents or co-encapsulation of both agents. For the preparation of void PEG-PLGA nanoparticles, 100 ul of water will be emulsified by continuous sonication of 1 ml dichloromethane solution of MPEG-PLGA and maleimide-MPEG-PLGA in a ratio of 9:1. This primary emulsion will be emulsified by sonication in 2 ml of 1% PVA poly (vinyl alcohol) solution. This water-in-oil-in-water emulsion will be diluted in to 40 ml of 0.5% PVA solution and stirred under magnetic stirring. Dichloromethane will be evaporated at 400 C under reduced pressure using a rotary evaporator and a heating bath. NPs will be separated by centrifugation at 20,000×g for 15 minutes and will be ready for further use.

EXAMPLE 32

Statistical Analysis

Statistical analysis was performed using one-way ANOVA and comparing the mean±SD from each experimental group with its respective control group. Statistical differences approaching $p<0.05$ were considered statistically significant differences. Tukey confidence intervals were used for pairwise comparisons. Groups were also compared using Kruskal-Wallis, a non-parametric ANOVA procedure.

In summary, data indicated that the beneficial use of LMWH is not due to its anticoagulant activity. In contrast, the anticoagulant property is a drawback in using heparin, and as shown in the animal model herein, heparin caused higher mortality in mice due to internal bleeding compared to other groups.

The development of SNACH helped in using heparin without its bleeding side effect. Different types of SNACH have been prepared and tested; they vary in their efficacy. In the investigation herein with respect to the present invention, S-SNACH demonstrated potent inhibition of pancreatic cancer adhesion, invasion, and metastasis (experimental metastasis) in addition to its inhibitory effects on tumor growth and tumor angiogenesis. The experiments were able to prove again the efficacy of S-SNACH in inhibiting experimental metastasis; it reached 72-82% decrease in liver metastasis compared to control group. S-SNACH was also safe and did not increase the rate of death among the mice even after increasing the dose of the compound.

Pancreatic cancer is the fourth-leading cause of cancer-related deaths in both males and females in the United States. The overall 5-year survival rate was 23.4% for patients who had surgical treatment due to metastasis or cancer resurgence. See Lim, E., et al., *In vivo bioluminescent imaging of mammary tumors using IVIS spectrum*. J Vis Exp, 2009 (26).

In working with a pancreatic cell cancer line due to its aggressive nature and, by trying to inhibit the surgically induced metastasis in an animal model, the present invention aims to increase the rate of survival in human patients after surgical treatment.

In 1995 a study was done to evaluate the use of heparin to reduce surgically induced venous thromboembolism. Re-analysis of the patients showed that the three years' mortality from disseminated malignancy was halved (9.2% vs. 21.4%), comparing patients who received heparin against those who did not [26]. It was demonstrated that tumor cells could be shed during surgical manipulation of the primary tumor. See Kakkar, A., et al., *Perioperative heparin-therapy inhibits late death from metastatic cancer*, Int J Oncol, 1995, 6(4): p. 885-8.

Giving S-SNACH before performing the surgery on the mice allowed the test compounds time to bind to the platelets' P-selectin and inhibit the platelets from binding to the disseminated cancer cells. The results obtained from using S-SNACH showed a decrease in cancer recurrence at the site of surgical removal compared to control ($p<0.05$), and it showed a decrease in liver metastasis.

The average dose of LMWH for enoxaparin in humans is 1.0-1.5 mg/kg and relatively higher in mice. In the experiment performed in the present invention, 5-10 mg/kg was used for LMWH (tinzaparin) and as high as 20-100 mg/kg was used for SNACH. SNACH was safely administered and did not increase the bleeding time compared to control group. The number of mouse deaths in all experiments was calculated at the end of the project and a high percentage of mice dying among the LMWH group due to internal bleeding was noticed, whereas the SNACH percentage of death in the SNACH group was statistically similar to the control.

It was observed that human P-selectin sensitivity to heparin inhibition is higher than mouse P-selection. See Borsig, L., et al., *Heparin and cancer revisited: mechanistic connections involving platelets, P-selectin, carcinoma mucins, and tumor metastasis*, Proc Natl Acad Sci USA, 2001, 98(6): p. 3352-7.

These findings suggest even better responses are to be expected in humans. These data suggest that SNACH is an effective and safe SNACH agents and warrant further clinical evaluation.

EXAMPLE 33

Preparation of Non-Anticoagulant LMW Heparin (NACH)

Heparin was fragmented by periodate oxidation based on a procedure from Islam et al., (*Carbohydrate Research* 337 (2002) 2239-2243). Heparin, sodium salt (20 g, 1.43 mmol) was dissolved in 175 mL of distilled water. The pH was adjusted to 5.0 using 1 M HCl, NaIO4 (15 g, 0.07 mol), dissolved in 500 mL water, was added in a single portion with stirring. The pH was readjusted to 5.0 using 1 M HCl and left for 24 h at 4° C. in the dark. The solution was dialyzed against 4 volumes of water (with one change of water) for 15 h at 4° C. To the approximately 1.5 L of solution obtained after dialysis, 32 mL of 10 M NaOH was added. The solution was stirred at room temperature for 3 h. To prevent the development of colored products, this step was done in the dark. $NaBH_4$ (1 g, 0.026 mol) was added in one portion, and the approximately 1.5 L of solution was stirred for 4 h. The pH was then adjusted to 4.0 using 37% HCl, and the solution was stirred for an additional 15 min. The solution was neutralized to pH 7.0 using 1 M NaOH and NaCl (32.8 g, 0.56 mol) followed by the addition of 2.54 L ethanol. The solution was left for 3 h without stirring, and the precipitate was recovered by centrifugation (22,000×g) for 20 min. The precipitate, recovered by decantation, was suspended in 400 mL absolute ethanol. The solution was filtered using a Buchner funnel, and the recovered solids were left to dry for 5 h under vacuum affording 14.2 g of product. The product was dissolved in 190 mL of water. NaCl (2.8 g, 0.05 mol) was added, and the pH was adjusted to 3.5 using 1 M HCl. The volume was adjusted to 280 mL using water. Absolute ethanol (240 mL) was added with stirring. The solution was stirred 15 min and then left without stirring for 10 h at room temperature. After decanting, the precipitate was recovered and dissolved in water. The ethanol was removed by rotary evaporation under reduced pressure, and the residue was freeze dried affording 10 g of LMW NACH.

Figure 28:
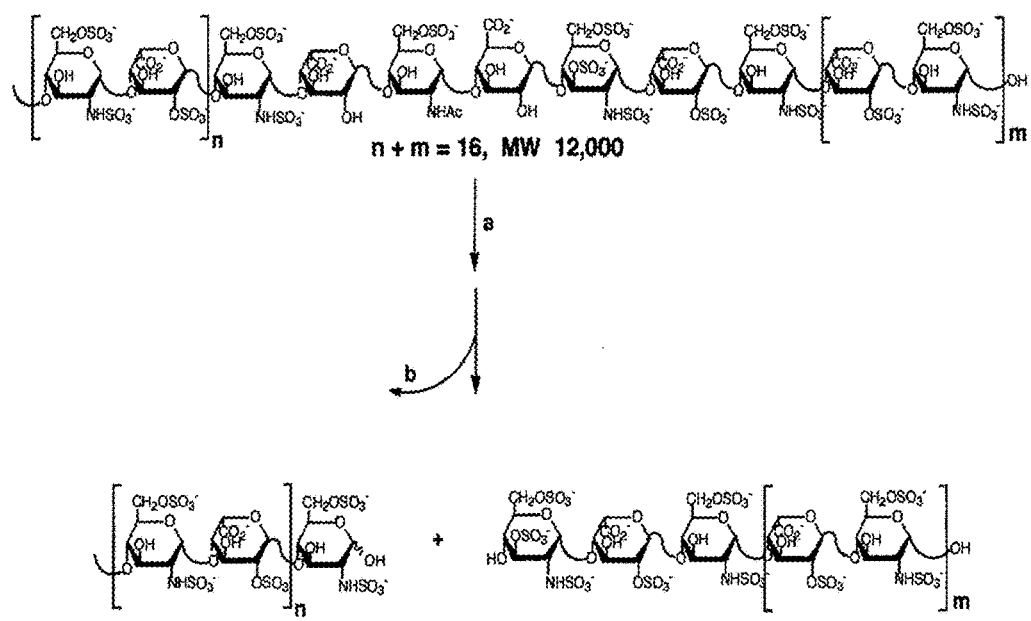
FIG. 28 depicts preparation of NACH, in accordance with embodiments of the present invention.

FIG. 28 depicts preparation of NACH, in accordance with embodiments of the present invention. In FIG. 28, "a" denotes periodate oxidation and fragmentation of heparin, and "b" denotes removal of the GlcpNAc-containing dialyzate.

EXAMPLE 34

Size Fractionation of Non-Anticoagulant LMW Heparin (NACH)

The parent porcine mucosal heparin has an average molecular weight ~12 000, while the resulting heparin fragments have an average degree of polymerization (dp) of 16, corresponding to a low molecular weight heparin of average molecular weight ~5000 (range from dp8 to dp24). To do the size fractionation in a 100 mg scale, the LMW NACH (200 mg/mL in 0.2 M sodium chloride, pH 7.0) is loaded onto a Bio-Gel P-6 column (i.d. 2.6/96 cm), eluted with 200 mM sodium chloride, and fractions (3 mL each) are collected at a flow rate of 16 mL/h. Fractions corresponding to each prominent peak with MW of 6000 Da and 4000 Da are pooled based on total carbohydrate analysis and PAGE analysis. The volume was reduced to about 10 mL using a rotary evaporator. The final products will be desalted with dialysis tube (MWCO 1000) and lyophilized.

This procedure can be scaled up to 500 g scale by increasing the size of P-6 chromatography column.

EXAMPLE 35

Preparation of LMW NACH with Different Sulfation Levels

Three sulfation levels (low, middle, and high) of LMW NACH are prepared with Vivapure Q Maxi H spin columns (Sartoriou Stedim Biotech, Bohemia, N.Y.). 20 mg of LMWH or LMW NACH is loaded onto a Vivapure Q Maxi H spin column and eluted step wisely with 10 mL of 200 mM, 800 mM and 2000 mM sodium chloride and fractions are collected separately. Fractions eluted from 200 mM, 800 mM and 2000 mM sodium chloride are corresponding to the three sulfation levels (low, middle, and high) of LMWH or LMW NACH. The final products are desalted with dialysis tube (MWCO 1000) and lyophilized.

The present invention includes methods and compositions for polyanionic glycosaminoglycan bound to polycatioinic nano carriers and/or encapsulated into nanoparticles.

The present invention includes methods of manufacturing and nanoformulation of Low Molecular Weight Heparins (LMWH) and sulfated Non-anticoagulant heparin from unfractionated heparin obtained from different sources including animal and bioengineered sources.

FIG. 29 provides a characterization of SNACH, in accordance with embodiments of the present invention. The ultra-Low Molecular Weight of non-anti-coagulant (NAC) heparin is 2,000-4,000 Daltons. The molecular weight of low molecular heparin is 4,000-6,000 Daltons and 6,000-8,000 Daltons. O-sulfation for SNACH is 25-65% of OH. O-sulfation for S-SNACH is 75-100% of OH.

Route of administration/formulation of the inventive nanoformulation include: (1) Formulated as an injectable for sustained release, Targeted delivery in combination with chemotherapy; (2) Oral nanoformulations' (3) Topical cream, patch; and (4) Eye drops or ointment.

Utilities of the present invention include: (1) Inhibition of metastasis in patients' pre- and post-tumor surgery and of spontaneous metastasis; (2) Cancer prevention; (3) Prevention of thrombotic events in cancer without risk of bleeding; and (4) Adjuvant to chemotherapy.

The present invention relates to oral and injectable nanoformulations of Sulfated to super-sulfated non-anticoagulant Low to ultra-Low Molecular Weight Heparins heparin (SNACH and S-SNACH), and corresponding methods of manufacture.

A drawback of LMWH is the short half-life as injectable, the lack of oral bioavailability, and bleeding adverse effects.

The present invention serves to provide a composition that exploits the advantageous properties of binding (ionic and/or covalent) the polyanionic GAGs to polycatioinic Nano carriers coated with permeation enhancers for improved gastrointestinal uptake and sustained release for longer half-life.

In one embodiment, a heparin tablet of the invention is coated with one or several layers of tablet coating excipients, such as to provide the tablet with an enteric coat and/or a coat physically stabilizing the tablet at a temperature at or above its melting point, and a corresponding coating process.

By way of examples it was surprisingly found that the solid heparin oral tablet composition of the invention increases the uptake of heparin in the gastrointestinal tract and/or prolongs its efficacy.

EXAMPLE 36

Animal Study

NZW rabbits were used in all experiments and tablets were administered orally. The animals were given four or six tablets followed by water until they had swallowed the tablets. The animals were deprived of food for about 18 hours before dosing. Blood samples were drawn from the ear veins in sodium citrate vials before dosing and ½, 1, 4, 6, and 8 hours after dosing for determination of APTT (Activated Partial Thromboplastin Time) on an IL Coagulation Systems ACL 2000 apparatus. The blood samples were centrifuged for 10 minutes at approximately 1000×g to obtain plasma for the analysis.

This invention provides a composition comprising a depolymerized glycosaminoglycan or derivative thereof covalently linked to chitosan conjugated to fatty acid such as eicosapentaenoic acid (EPA), docosahexaenoic acid (DHA), and/or Poly L-arginine.

EXAMPLE 37

Preparation of Modified Glycosaminoglycans (GAGs)

Commercially available crude product of digested porcine mucosa or fresh porcine mucosa may be used as starting materials. Porcine intestinal mucosa may be enzymatically digested and the solids removed by centrifugation. The solubilized glycosaminoglycans containing solution is passed through a Dowex ion exchanger in the acid form and is eluted from the column with sodium chloride to produce a broad range of molecular weight GAGs. The GAGs of interest are purified from the mixture with cetyl-pyridinium chloride followed by salt and alcohol to further separate the undesirable carbohydrates. The products of this preliminary separation are subjected to enzymatic depolymerization according to the method first described by Pajza, N and Korn G. D., Biochem. Acta, vol. 20, page 596 (1956) or by a free radical method described by Cifonelli, Methods in Carbohydrate Chemistry, vol. 7, pages 139-141 (1976), using nitrous acid. The fragments produced by either enzymatic or free radical depolymerization after fractionation by column methods or by fractional precipitation produce unique species of GAG's with an ability to inhibit the coagulation process as for example Factor Xa inhibitors.

EXAMPLE 38

Enzymatic Depolymerization

Using flavobacteria digestion, the lower molecular weight GAG's are prepared by inoculating 12 grams of mucosal crude GAG with 6 grams of crude flavobacteria extract in 500 ml of 0.02 N phosphate buffer at 25.degree. C. for 72 hours. The reaction is stopped by the addition of cold 20% trichloroacetic acid. The mixture is filtered and the filtrate is dialyzed for about 16 hours against three changes of distilled water in seamless cellulose dialyzer tubing with a 3500 D cutoff. The sodium salt of GAG is prepared by lyophilization of the mixture solution.

EXAMPLE 39

Free Radical Depolymerization

A relatively mild depolymerization method uses organic nitrite at low temperature which provides cleavage at specific linkages. This yields unaltered fragments which can be separated by a variety of methods including high pressure liquid chromatography, and alcohol-water precipitation. Free amino groups and other sulf-amino groups are reactive sites and ester sulfates and N-acetyl groups and otherwise easily hydrolysable linkages survive free radical depolymerization. A 0.1 M solution of nitrous acid reagent is prepared by mixing a 3.5% solution of sodium nitrate (10 ml) with 1,2 dimethoxyethane (20 ml) and 2M hydrochloric acid (5 ml) and cooled to −20 degrees C. The solution is used within a few hours of preparation. The free acid form of the glycosaminoglycan (250 mg) is used for the depolymerization. The reaction is maintained for 1 hour with mixing and the reaction is inhibited by adding 12% ammonium sulfamate (final concentration). The reaction mixture is eluted with 0.2 M sodium acetate in 10% ethanol following neutralization by gel filtration on SEPHADEX G-25. The first major fraction eluted has a molecular weight of 3000 Da and the second major fraction is a tetra saccharide.

The utilization of biodegradable/biocompatible polymeric materials can provide unprecedented opportunities for addressing many of the current lacunas in diagnosis and therapy of breast cancer. The nanoparticulate system has a tremendous potential due to its versatility for carrying therapeutic agent along with multiple imaging probes. Also, the ability to attach a targeting moiety by modifying surface functionality might improve its efficacy.

GAG Derivatives Nanoformulations (SNACH, S-SNACH or LMWH) include:
a) PLGA Nanoparticles prepared by double emulsion/solvent evaporation methods;
b) Chitosan Nanoparticles prepared by reverse micelle method;
c) Synthesis of omega-3-fatty acid such as DHA or EPA conjugated with chitosan or as such with GAG derivatives (SNACH, S-SNACH or LMWH) at Carboxyl Group of the fatty acids DHA or EPA;
d) Blend of Chitosan and PLGA at different ratios to obtain positive zeta potential (<20 my) prepared by double emulsion/solvent evaporation methods;
e) Blend of MPEG-PLGA (methoxy-polyethyleneglycol-poly (lactide-co-glycolide) and maleimide-PEG-PLGA prepared by double emulsion/solvent evaporation methods. The molecular weight of PEG in maleimide-PEG-PLGA chosen was higher than that in MPEG-PLGA, for carrier conjugation to maleimide functional groups;
f) Blend of PLGA-Polycaprolate prepared by double emulsion/solvent evaporation methods;
g) Calcium alginate Nanoparticles.

Heparin and derivatives including S-NACH or S-SNACH were labeled with FITC and the Nanoparticles labeled with different fluorescence tag were utilized for cell permeation studies in real time using confocal imaging and for in vivo imaging using IVIS imaging system.

EXAMPLE 40

Preparation of Void PEG-PLGA Nanoparticles 100 ul of water was emulsified by continuous sonication (30s) of 1 ml dichloromethane solution of MPEG-PLGA and maleimide-MPEG-PLGA in a ratio of 9:1. This primary emulsion was inter-massively emulsified by sonication (30s) in 2 ml of 1% PVA poly (vinyl alcohol) or 1-5% deoxycholate solution. This water-in-oil-in-water emulsion was diluted in to 40 ml of PVA or deoxycholate solution and stirred for few minutes under magnetic stirring. Immediately after, dichloromethane was evaporated at low pressure and at 400 C by using a rotatory evaporator and a heating bath. Nanoparticles were separated by centrifugation at high speed ultra-centrifugation for further use. In case of heparin derivatives doped 100 ul (100 mg/ml) of aqueous solution of heparin derivative was used instead of water.

The products of degradation of mucosal GAG by either enzymatic or free radical methods followed by fractionation will have N-sulfate groups that are the site of derivitization in the fatty acids. In the process of derivatization, the sulfate is removed to expose the reactive amino group. The sodium salt of the GAG is converted to the free acid and rapidly converted to the pyridium salt to protect the COOH group.

EXAMPLE 41

One half gram of pyridine-GAG derivative is dissolved in 23 ml of DMSO in 3 ml $H_2O$ and maintained at a pH of 4.75. Cholic acid (0.15 gm) is dissolved in 20 ml of DMSO in 3 ml of $H_2O$ to this added 0.5 gm of EDC (1 ethyl $C$-3-$C_3$-dimethylene propyl) carbodiamide and the mixture added to pyridine GAG with constant stirring, maintaining the pH at 4.8 at 25 degree centigrade for 2 hours. The reaction products are dialyzed against 2 liters of water with three changes using seamless tubing with a 3500 D cutoff. The precipitate that forms is removed by filtration. The filtrate is lyophilized and the white powder is dissolved in 10 ml of sodium acetate (6.8%) and the pH adjusted to 7.8. Three volumes of ethyl alcohol are added to the solution and the precipitate is recovered by centrifugation at 10,000×g for 30 minutes and washed with alcohol. The dried precipitate is then dissolved in water and lyophilized. The yield of final product is 70%.s then dissolved in water and lyophilized. The yield of final product is 70%.

EXAMPLE 42

One gram of pyridine-GAG derivative in 20 ml DMSO containing 3 ml $H_2O$ is maintained at pH 4.75. The DMSO soluble dehydrocholic acid (1 gm) was activated by one gram EDC in DMSO for 2 hours at room temperature. The pyridine GAG was added, the mixture maintained at a pH of 4.75 overnight, and then dialyzed, centrifuged and finally lyophilized. The product was dissolved in 10 ml of sodium acetate and the pH adjusted to 7.8 and then treated as in Example 41.

EXAMPLE 43

One gram of pyridine-GAG was dissolved 20 ml DMSO containing 3 ml $H_2O$ and the pH maintained at 4.8 and 0.25 gram of glycolic acid was activated in 20 ml DMSO containing 3 ml distilled water. By adding 0.5 gm EDC the mixture was added to pyridine GAG with constant stirring while maintaining pH at 4.8 at 25 degree C. for 2 hours.

EXAMPLE 44

Assay of GAG and GAG-Chitosan-Fatty Acid and/or L-Arginine Derivatives for Activity By anti-Xa Method: The Stago Statchron Kit #00906 using a Dade Behring BCS instrument calibrated with enoxaparin diluted in pooled plasma was used. In this assay para-nitroamide released is measured at 405 nm and is inversely proportional to the amount of GAG present in the plasma sample.

EXAMPLE 45

By aPTT Assay: Clotting Time is Measured with Fibro-Meter and Coagulation Analyzer A nanoparticulate system made up of a blend of MPEG-PLGA (methoxy-polyethyleneglycol-poly (lactide-co-glycolide) and maleimide-PEG-PLGA was synthesized. These nanoparticles were prepared by double emulsion/solvent evaporation methods (9). PEG-PLGA, maleimide-PEG-PLGA nanoparticles were capable of encapsulation of polyanionic sulfated non-anticoagulant heparin (S-NACH) and its analogs/different chemotherapeutic agents or co-encapsulation of both. The molecular weight of PEG in maleimide-PEG-PLGA chosen was higher than that in MPEG-PLGA, so that the maleimide function would be available for conjugating the thiolated antibody/thiolated $\alpha v\beta 3$ ligands. Thus, these nanoparticles will have the capacity for the targeted delivery to the specific site due to the conjugation of a targeting moiety into the surface by maleimide group.

For the preparation of void PEG-PLGA nanoparticles, 100 ul of water was emulsified by continuous sonication (30 seconds) of 1 ml dichloromethane solution of MPEG-PLGA and maleimide-MPEG-PLGA in a ratio of 9:1. The primary emulsion was inter-massively emulsified by sonication (30 seconds) in 2 ml of 1% PVA poly (vinyl alcohol) solution. This water-in-oil-in-water emulsion was diluted in to 40 ml of 0.5% PVA solution and stirred for few minutes under magnetic stirring. Immediately after, dichloromethane was evaporated at low pressure and at 400 C by using a rotatory evaporator and a heating bath. Nanoparticles were separated by centrifugation at high speed ultra-centrifugation for further use. In case of S-NACH doped or S-NACH/Chemotherapeutics agent doped nanoparticles 100 ul of aqueous solution of S-NACH/S-NACH+chemotherapeutic agent was used instead of water. Conjugation of antibody/$\alpha v\beta 3$ for targeted delivery of this S-NACH doped or S-NACH+ chemotherapeutic nanoparticles will be done by first etiolating the antibody or $\alpha v\beta 3$ by using Traut's reagent. These thiolated antibody or $\alpha v\beta 3$ will readily react with the maleimide group present in the surface of the nanoparticles.

FIG. 30 is a schematic diagram for preparation of $\alpha v\beta 3$ conjugated NACH doped PEG-PLGA nanoparticles, in accordance with embodiments of the present invention.

FIG. 31 is a schematic diagram for preparation of $\alpha v\beta 3$ conjugated S-NACH and chemotherapeutic agent doped PEG-PLGA nanoparticles, in accordance with embodiments of the present invention.

Figure 32:
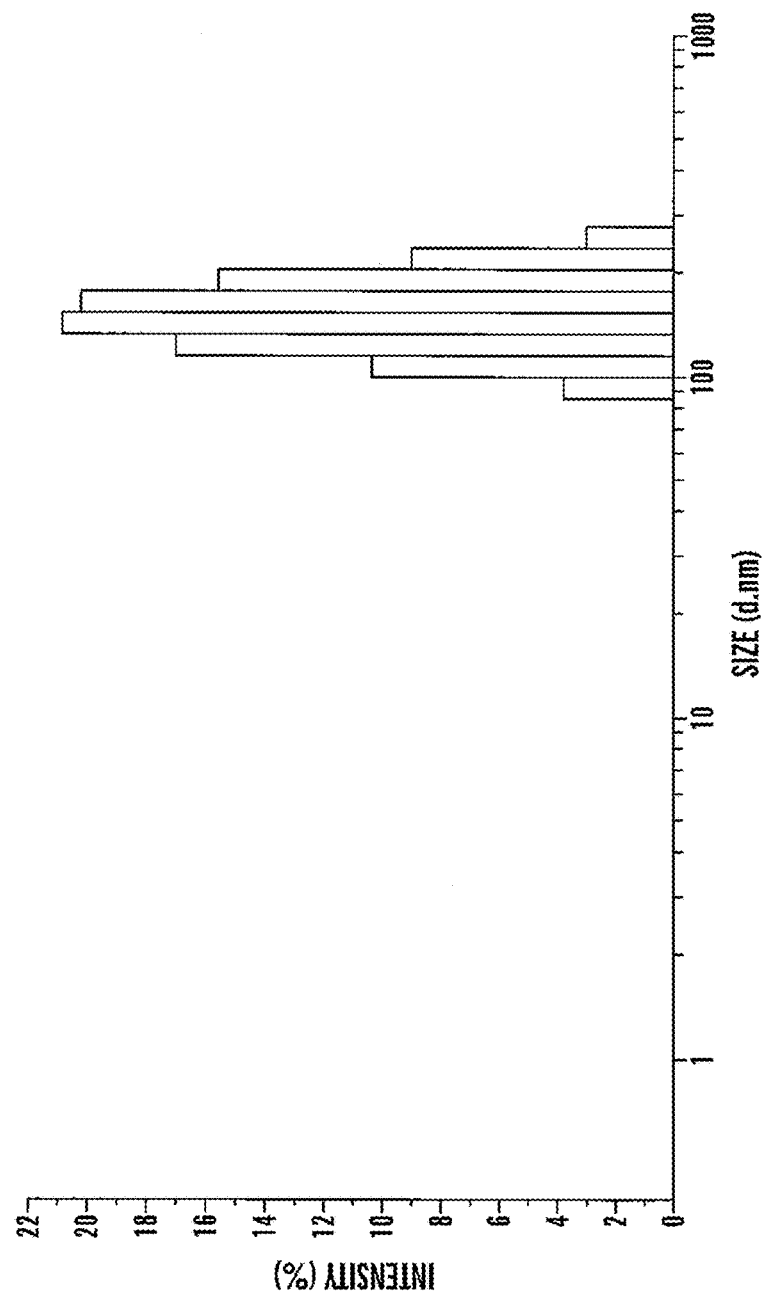
FIG. 32 depicts DLS data showing the size distribution of PLGA nanoparticles, in accordance with embodiments of the present invention.

FIG. 32 depicts DLS data showing the size distribution of PLGA nanoparticles, in accordance with embodiments of the present invention. The average size is about 150 nm. FIG. 32 shows non-anticoagulant oxidized low (n=5 to 10) and ultra-low (n=2 to 4)—molecular weight heparin derivatives, which were then subjected to chemical sulfation.

EXAMPLE 46

Delivery of Nano-Encapsulated LMWH, SNACH or S-SNACH

In comparison to low molecular weight heparin (LMWH), sulfated non-anticoagulant heparin (SNACH) or S-SNAH has minimal effects on hemostasis. Encapsulation of chemotherapeutic agents and SNACH in biodegradable nanoparticles has tremendous potential in improving survival among cancer patients. Furthermore, custom-made nanoparticles with a targeted moiety on the surface of the shell of the nanoparticle would enable us to increase the efficacy and decrease the adverse effects of chemotherapy such as doxorubicin.

EXAMPLE 47

PLGA-PEG nanoparticles co-encapsulating SNACH and doxorubicin were synthesized by double emulsion solvent evaporation method. The in vitro efficacy of these nanoparticles was examined in MCF-7 doxorubicin resistant (MCF-7R) cells using MTT cell viability assay. Confocal microscopy was used to examine the uptake of $\alpha v\beta 3$ antibody conjugated nanoparticles in human dermal micro-vascular endothelial cells (HDMEC), which are known to over express $\alpha v\beta 3$ integrins.

Results of size measurement by DLS revealed that these nanoparticles co-encapsulating doxorubicin and heparins to be 200-300 nm in size. Data from the MTT assays in MCF-7R cells showed synergy between SNACH and doxorubicin when encapsulated in PLGA-PEG nanoparticles. Confocal imaging in HDMEC cells indicates that these nanoparticles have the potential to be used for site specific delivery to the tumor neovascularization. In vivo data in nude mice xenograft (MCF-7R) are shown in Table 5 (doses of doxorubicin and NACH injected subcutaneously were 0.625 mg/kg and 2.5 mg/kg body weight, respectively). Significant decrease in tumor weight was observed in the mice xenograft, when treated with $\alpha v\beta 3$.conjugated nanoparticles co-encapsulating doxorubicin or to greater extent doxorubicin and SNACH compares to its non-encapsulated counterparts. These data indicated distinct improvement in the anti-tumor efficacy using $\alpha v\beta 3$ site directed delivery doxorubicin and SNACH encapsulated in PLGA-PEG nanoparticles.

EXAMPLE 48

Amino Acid Conjugation to SNACH, LMWH or S-SNACH

Below is an example of product when coupling to the carboxylic end of a polypeptide.

For simplicity dipeptide examples are shown. In addition the R1 side chains coming up out the plane of the rings were left as sulfate groups.

The structure below shows conjugation of SNACH or LMWH in polycatioinic polymers such as poly (amidoamine) (PAMAM), poly lysine, and other known polycatioinic polymers.

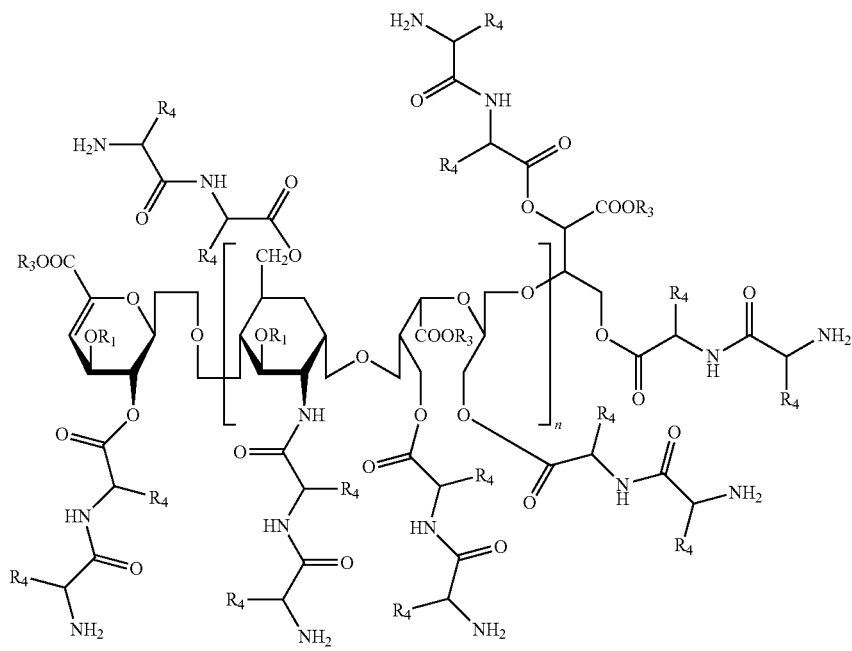
$R_1 = SO_3^-$; $R_3 = $ H or $Na^+$; $R_4 = $ amino acid side chain
EXAMPLE 49
Poly vinyl alcohol (PVA) was the simplest example because it has no other functionality to contend with. Yet, depending upon equivalents of reagents used in the reaction one could end up with multiple SNACH per PVA or vice versa.
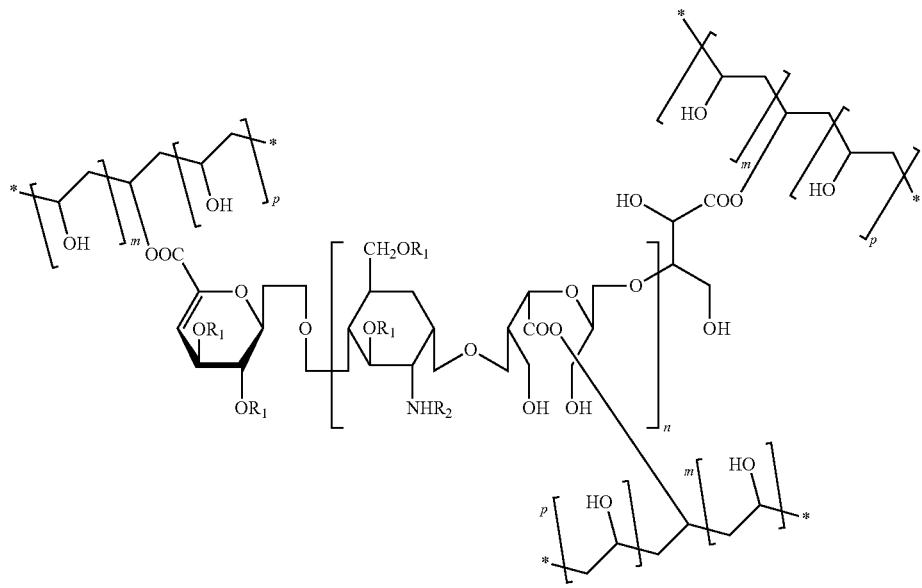
$R_1 = $ H or $SO_3^-$; $R_2 = $ H or Ac or $SO_3^-$;

SNACH, S-SNACH or LMWH may be conjugated to polymer and then nanoparticles may be synthesized using the following four methods.

In a first method 1, heparin derivatives (SNACH, S-SNACH or LMWH) via its carboxylic acid react with polymer hydroxyl group to form ester (e.g., PVA, Cellulose).

In a second method 1, heparin derivatives (SNACH S-SNACH or LMWH) via its carboxylic acid react with polymer with amine group to form amide (e.g., chitosan, poly L-lysine or Poly L-arginine).

In a third method 1, heparin derivatives (SNACH, S-SNACH or LMWH) via its hydroxyl react with polymer carboxylic acid group to form ester (e.g., poly acrylic acid, PLGA, fatty acids such as DHA and EPA).

In a fourth method 1, heparin derivatives (SNACH, S-SNACH or LMWH) via its amine (NH2) react with polymer carboxylic acid group to form amide (e.g., poly acrylic acid PLGA, fatty acids such as DHA and EPA).

Figure 33:
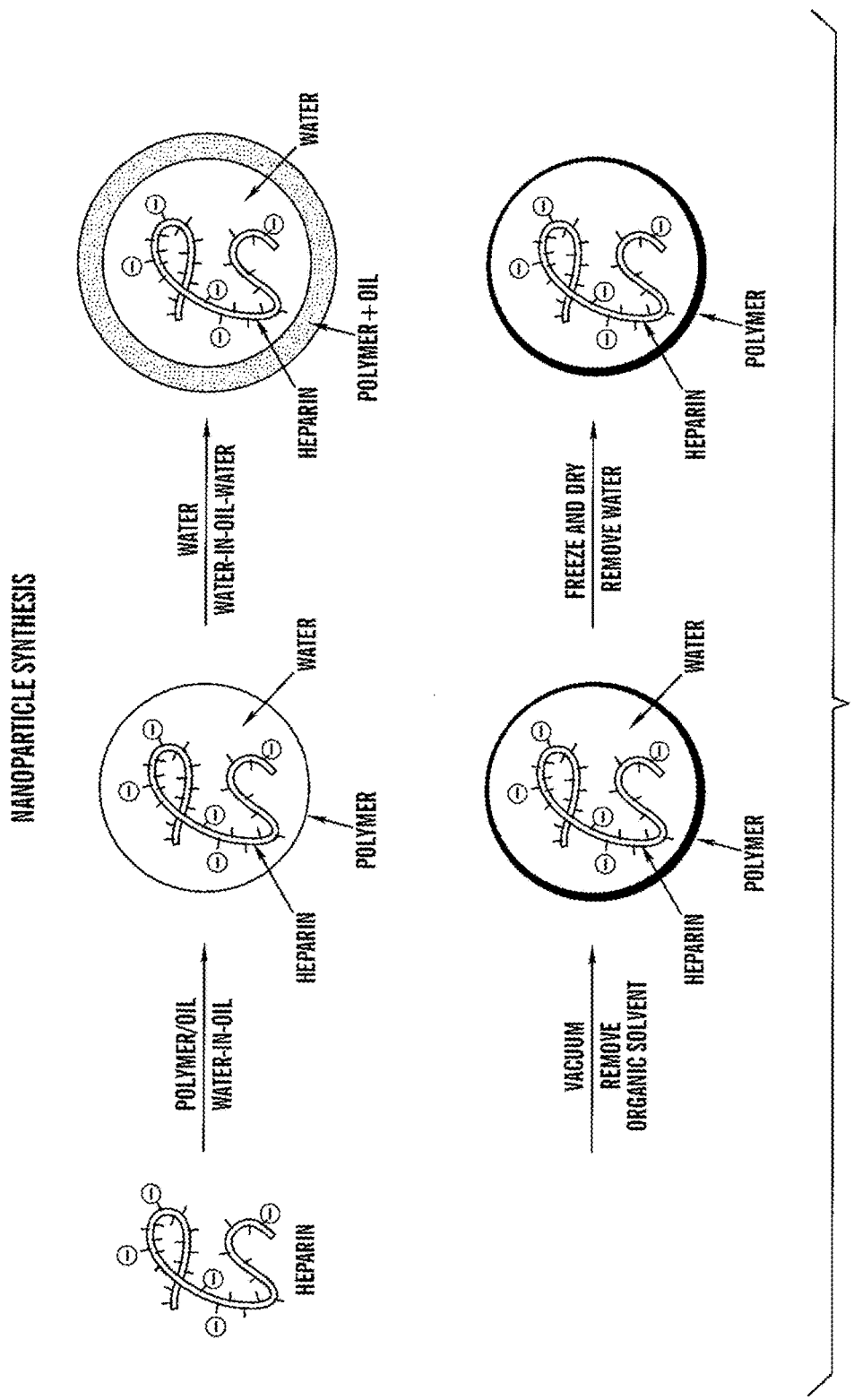
FIG. 33 is a scheme for heparin derivatives (SNACH, S-SNACH or LMWH) nano polymer/nanoparticle synthesis, in accordance with embodiments of the present invention.

FIG. 33 is a scheme for heparin derivatives (SNACH, S-SNACH or LMWH) nano polymer/nanoparticle synthesis.

EXAMPLE 50

The preparation of nanoparticles was based on an oil/water emulsification-solvent evaporation method. A fixed amount of polymer (200 mg) as outlined in Methods 1-4 above, either chitosan, PLGA or their respective mixture (1:1) was used in all formulations. The matrix polymer was dissolved in 3 ml of ethyl acetate. This solution was poured into 10 ml of the aqueous phase containing the appropriate concentration of poly (vinyl alcohol) (Chitosan: 0.001%; Chitosan+PLGA: 0.2%; PLGA: 5%) and an oil/water emulsion was formed by ultra-sonication for varying time intervals (Chitosan+PLGA: 3 min; PLGA: 4 min) in order to obtain equivalent particle diameters of around 100 nm for the three NP types. The solvent was removed under reduced pressure and nanoparticles were dialyzed (Spectrapor® 7, Spectrum Ltd, USA; membrane pore size: 50 000 Da) against distilled water in order to remove the poly (vinyl alcohol) from the external aqueous phase. NP batches were analyzed for their size distribution and their zeta potential using a Zeta sizer II® (Malvern Instruments, UK). The association efficiency between nanoparticles and LMWH was determined as follows: 20 mg of nanoparticles was mixed with 1000 IU of the commercialized LMWH solution by vortexing for 1 minute, nanoparticles were separated from supernatant by centrifugation at 10,000×g for 30 min and the SNACH, S-SNACH or LMWH amount in the supernatant was quantified.

EXAMPLE 51

A double emulsion solvent extraction procedure was used to prepare the heparin derivatives (SNACH, S-SNACH or LMWH)—loaded PLGA. Aqueous solution of heparin derivatives (400 mcg/ml) was emulsified in 2 ml of a methylene chloride solution of PLGA (100 mg/ml). The PLGA heparin derivative mixture was then sonicated for 10 seconds (ultrasonic probe, Sonics & Materials Inc.): 4 ml of 1% poly (vinyl alcohol) (PVA) was added to this solution and vortexed for 10 seconds. This was then diluted in 200 ml of 0.3% PVA solution and stirred for 5 minutes. 400 ml of an aqueous solution of isopropanol (2% by volume) was added to accelerate the extraction of the solvent. After 45 minutes of stirring, the microspheres were collected by centrifugation at 10,000×g for 10 minutes, washed three times in distilled water and freeze-dried overnight.

EXAMPLE 52

Nanoparticles are composed of heparin derivatives—PLGA [Poly (lactide-Co-Glycolic acid)]—PEG (poly ethylene glycol) copolymers. In aqueous media, they spontaneously generate nanoparticles with heparin derivatives and to remove all the reagents in excess, the nanoparticle suspensions were dialyzed. 10,000-100,000 Da molecular weight cut off membrane dialysis was used to purify around. The purified nanoparticle suspensions were then collected and kept at 4 degrees C. until evaluated.

Figure 34:
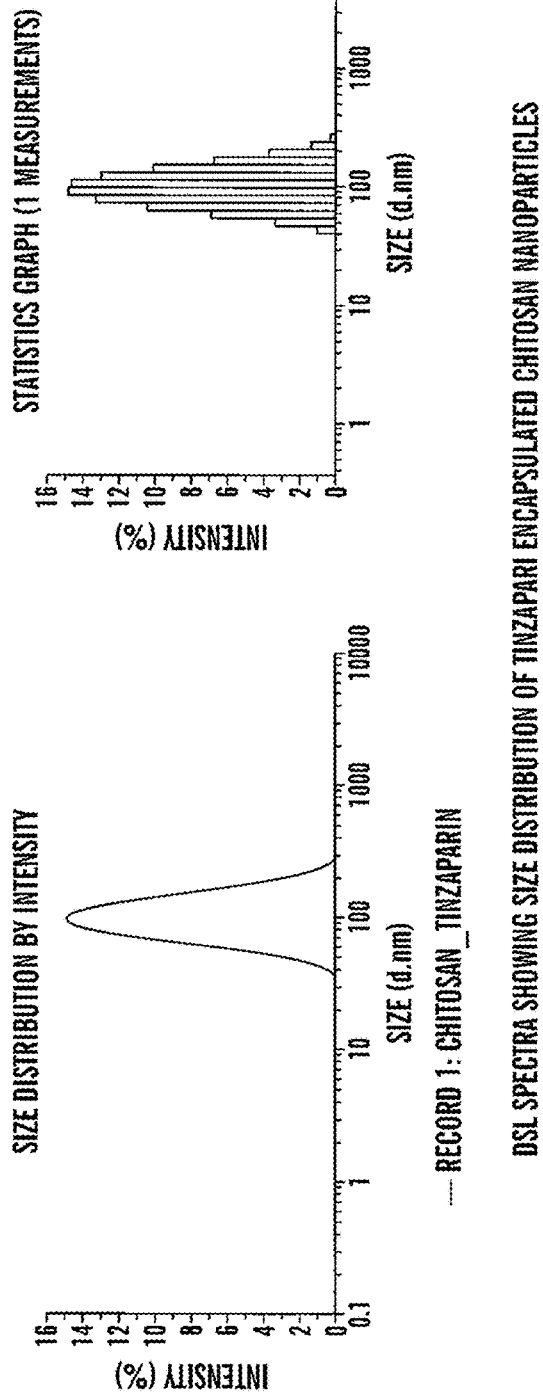
FIG. 34 depicts DLS spectra showing size distribution of tinzaparin encapsulated Chitosan nanoparticles and of tinzaparin encapsulated PLGA-Chitosan nanoparticles, in accordance with embodiments of the present invention.
Figure 34:
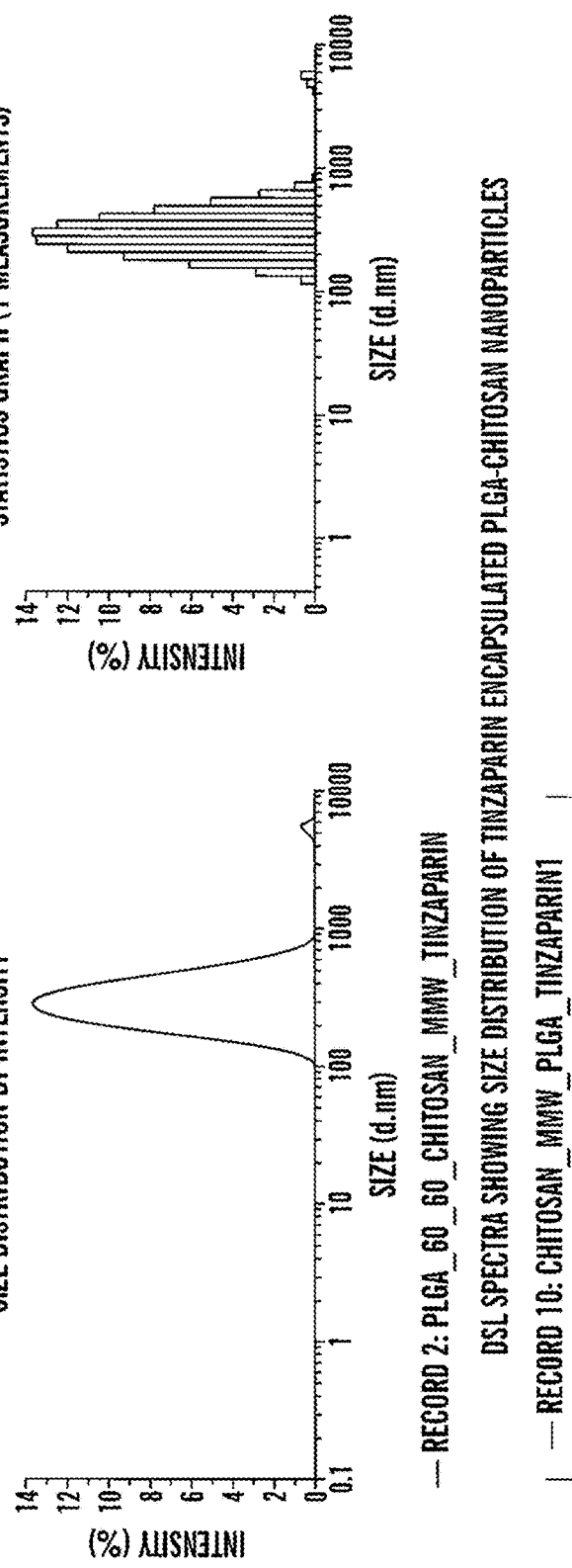

FIG. 34 depicts DLS spectra showing size distribution of tinzaparin encapsulated Chitosan nanoparticles (Panel A) and of tinzaparin encapsulated PLGA-Chitosan nanoparticles (Panel B), in accordance with embodiments of the present invention. The data potential data in FIG. 34 indicate that the (−) charge of tinzaparin can be increased by encapsulation.

Figure 35:
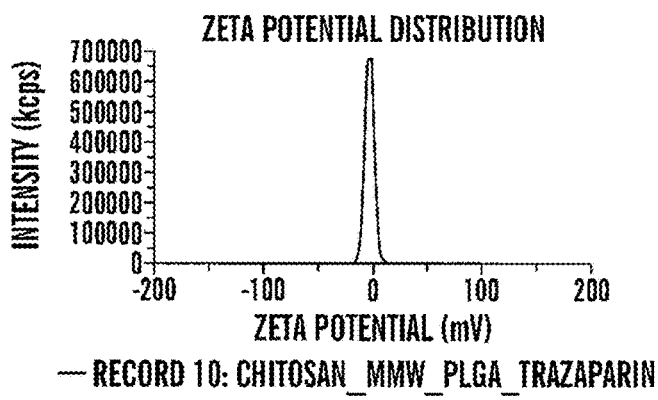
FIG. 35 depicts the zeta potential of tinzaparin, the zeta potential of tinzaparin encapsulated chitosan nanoparticles, and the zeta potential of tinzaparin encapsulated PLGA nanoparticles, in accordance with embodiments of the present invention.

FIG. 35 depicts the zeta potential of tinzaparin, the zeta potential of tinzaparin encapsulated chitosan nanoparticles, and the zeta potential of tinzaparin encapsulated PLGA nanoparticles, in accordance with embodiments of the present invention.

Figure 36:
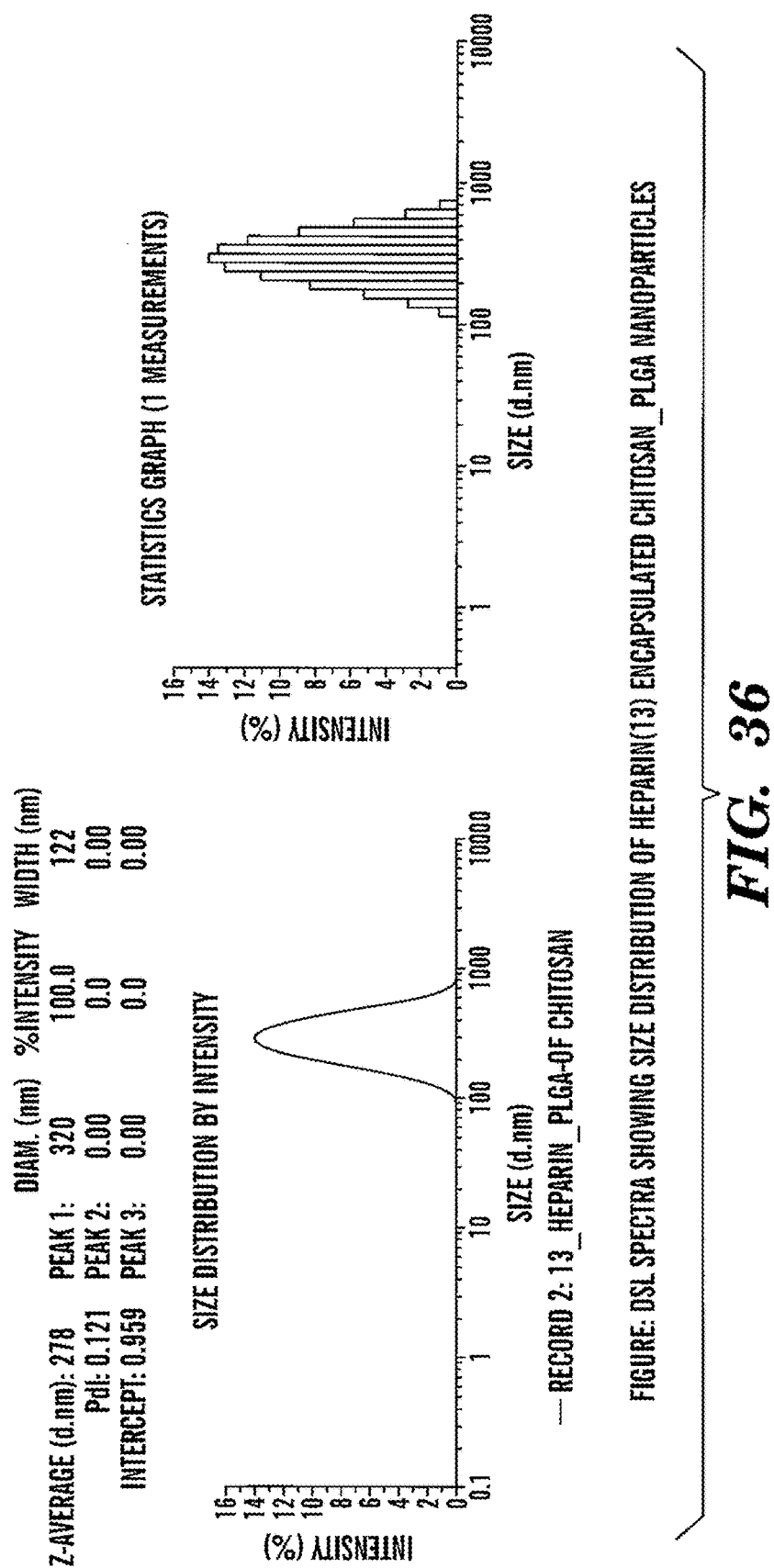
FIG. 36 depicts DLS spectra showing: size distribution of heparin encapsulated Chitosan-PLGA nanoparticles; and size distribution of tinzaparin encapsulated Chitosan-PLGA nanoparticles, in accordance with embodiments of the present invention.
Figure 36:
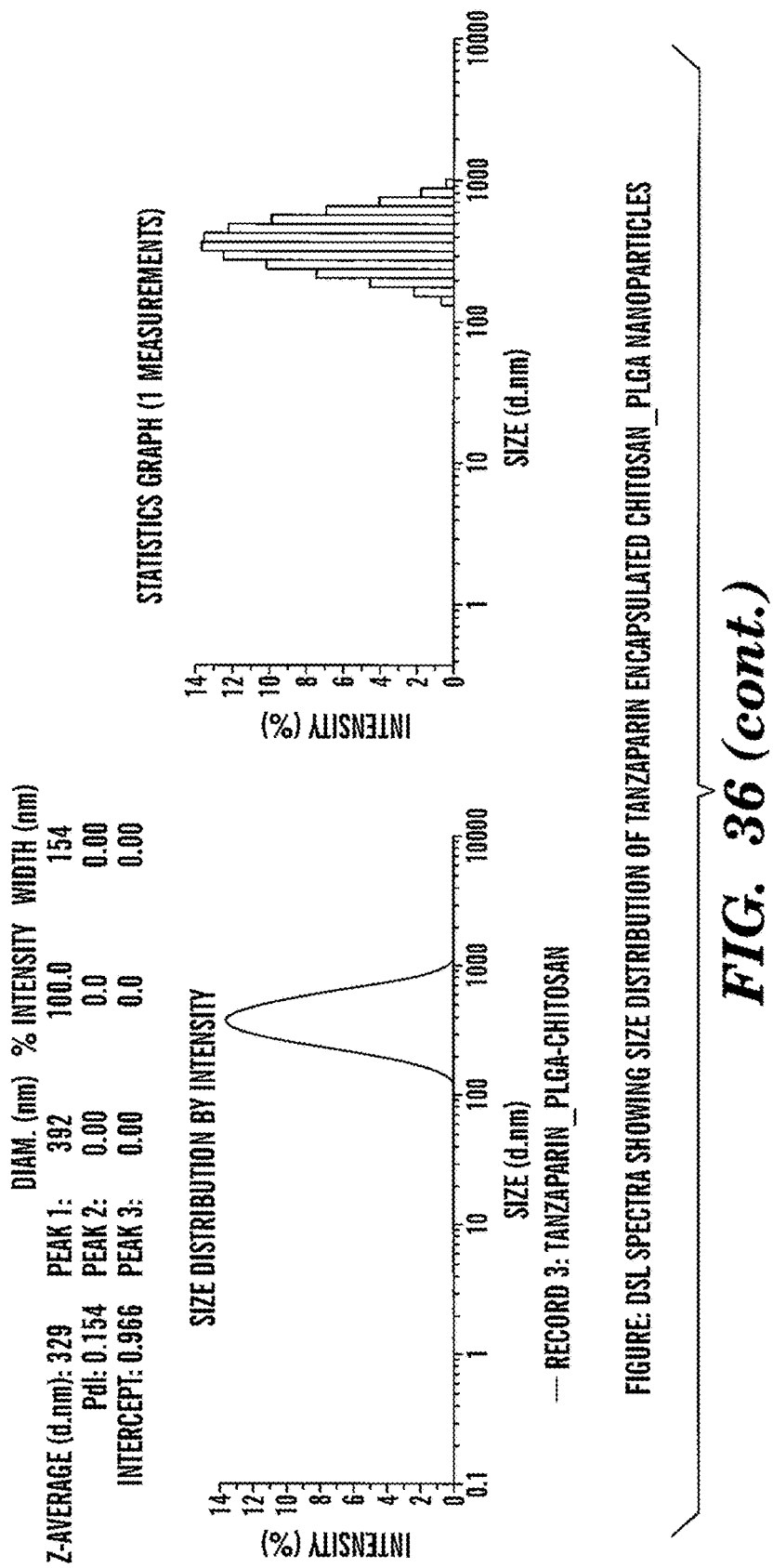

FIG. 36 depicts DLS spectra showing: (a) size distribution of heparin encapsulated Chitosan-PLGA nanoparticles and (b) size distribution of tinzaparin encapsulated Chitosan-PLGA nanoparticles, in accordance with embodiments of the present invention.

FIG. 37 depicts zeta potential of tinzaparin, zeta potential of tinzaparin encapsulated chitosan-PLGA nanoparticles, zeta potential of heparin (13) encapsulated chitosan-PLGA nanoparticles, and zeta potential of heparin (8) encapsulated chitosan-PLGA nanoparticles, in accordance with embodiments of the present invention. Heparin (13) and heparin (8) are sulfated non-anticoagulant LMWH (average molecular weight=6,500 Dalton) and Ultra-LMWH (average molecular weight=4,000 Dalton), respectively.

Figure 38:
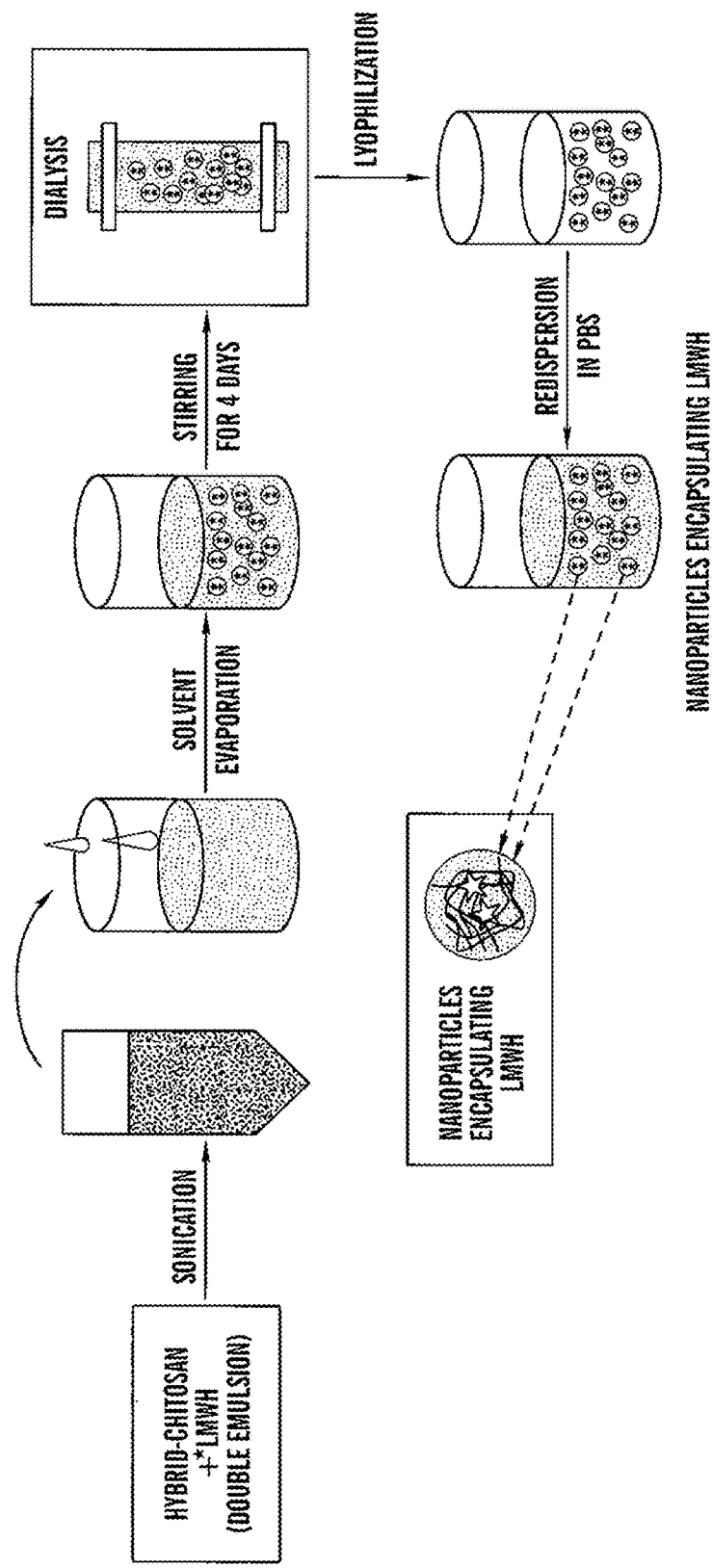
FIG. 38 is a schematic diagram showing the synthesis of chitosan-deoxycholic acid nanoparticles (CH-DC-NPs) encapsulating LMWH or SNACH, in accordance with embodiments of the present invention.

FIG. 38 is a schematic diagram showing the synthesis of chitosan-deoxycholic acid nanoparticles (CH-DC-NPs) encapsulating LMWH or SNACH, in accordance with embodiments of the present invention. In one embodiment, the synthesized formulation in FIG. 38 may be delivered to a subject or patient orally. Hybrid chitosan nanoparticles conjugated to deoxycholic acid (CH-DC-NPs) will be synthesized by double emulsion solvent evaporation method. Thus, the nanoparticulate carrier system encapsulating SNACH or LMWH, composed of both chitosan polymer (known to increase oral bioavailability due to its mucoadhesive properties) and deoxycholic acid (a well-known permeation enhancer), has the tremendous potential to increase the oral bioavailability of the encapsulate SNACH or LMWH by many fold.

The inventor of the present invention has demonstrated, in the laboratory, an ability to synthesize hybrid chitosan polymer conjugated to deoxycholic acid using crabodiimide chemistry to link free —NH2 and —COOH group present in chitosan and deoxycholic acid respectively. This hybrid polymer was used to synthesize CH-DC-NPs nanoparticles and to encapsulate LMWH or SNACH as shown in FIG. 38.

The nanoparticles may be conjugated to bile acids. In one embodiment, the bile acids are cholic acid, deoxycholic acid, and/or lithocholic acid.

Figure 39:
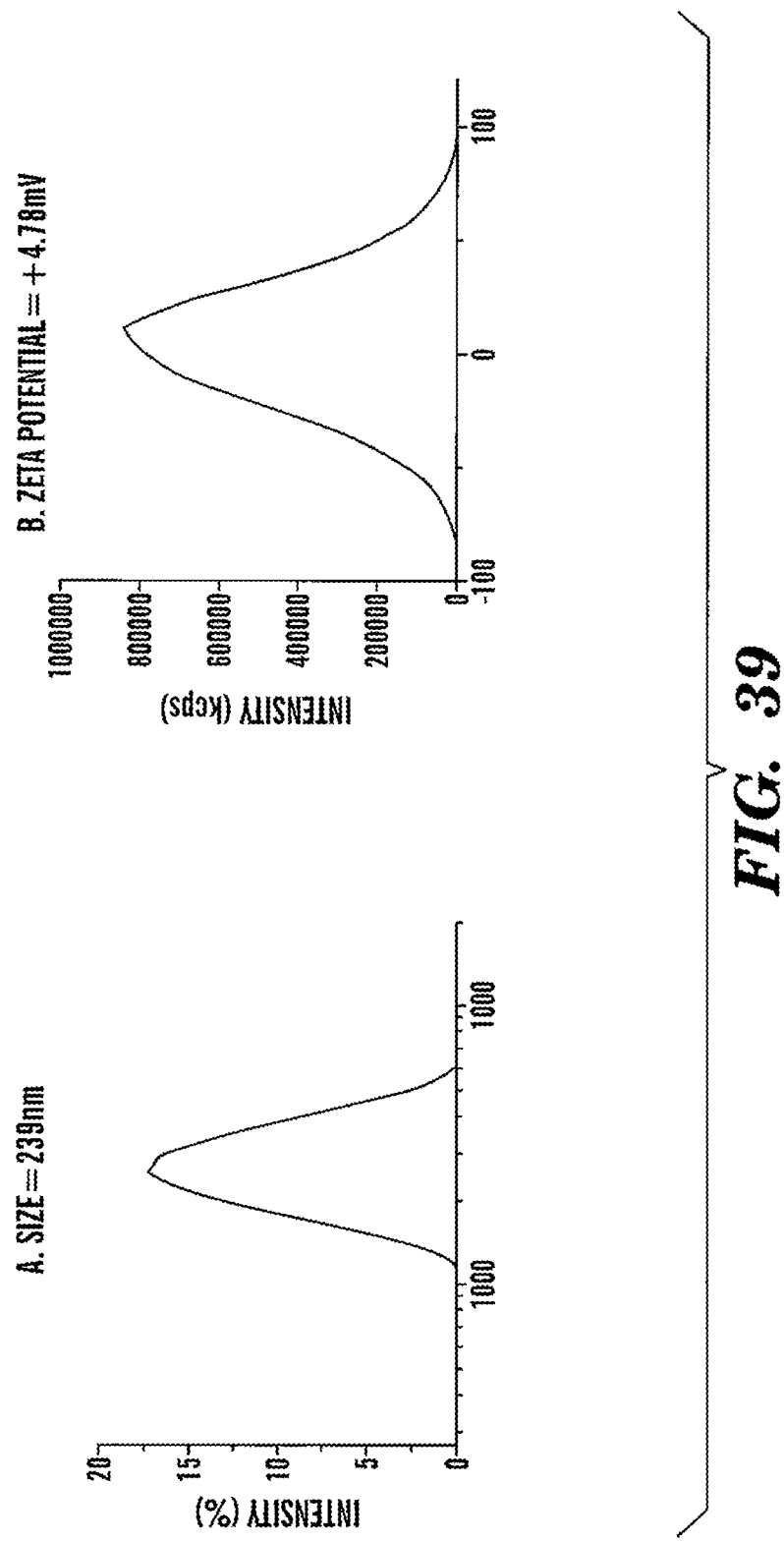
FIG. 39 depicts: A) Size measurement of CH-DA-NPs; and B) Zeta potential measurement of CH-DA-NPs, in accordance with embodiments of the present invention.

FIG. 39 depicts: A) Size measurement of CH-DA-NPs; and B) Zeta potential measurement of CH-DA-NPs, in accordance with embodiments of the present invention.

Figure 40:
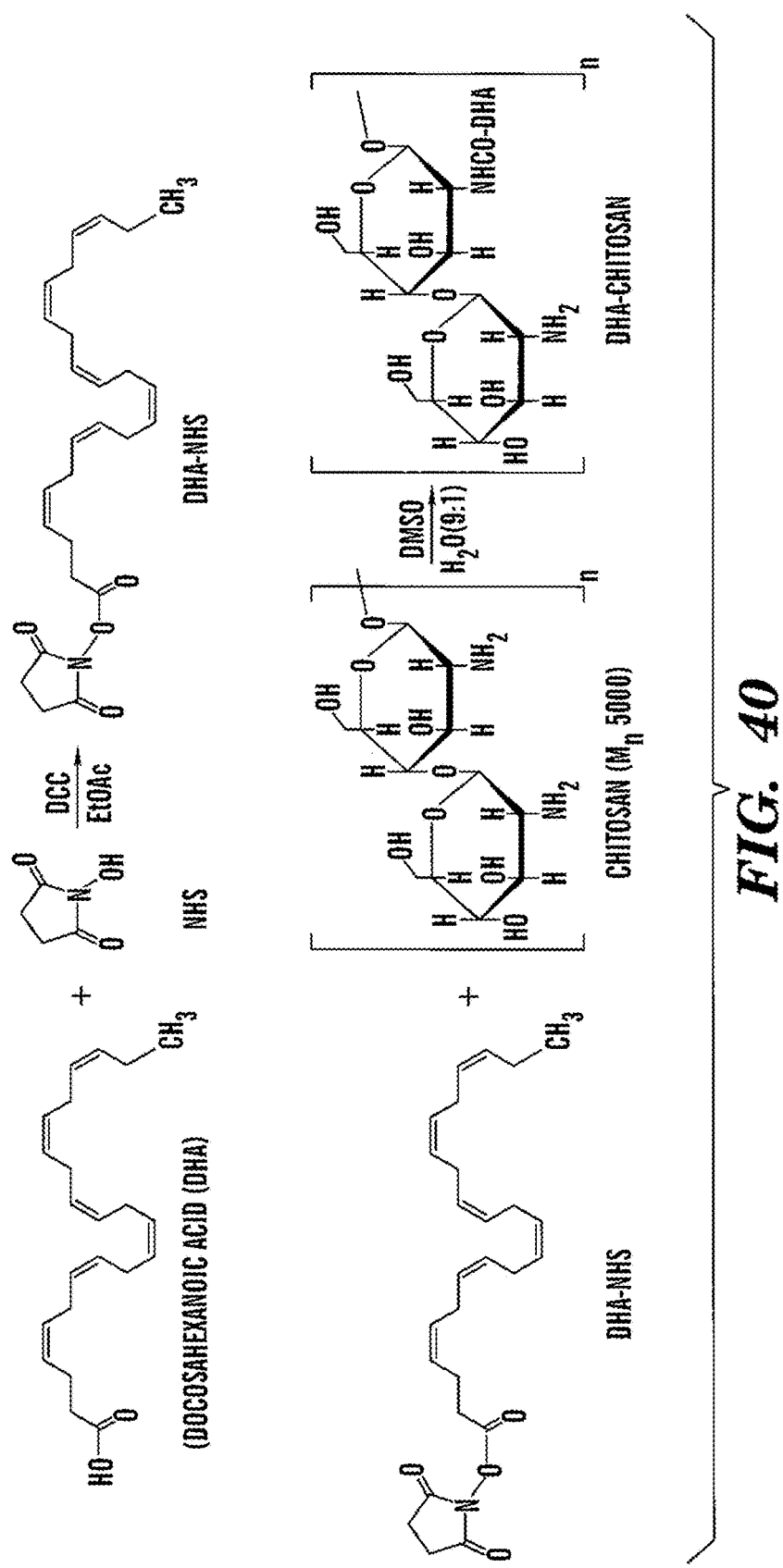
FIG. 40 depicts a synthesis of DHA-Chitosan, in accordance with embodiments of the present invention.

FIG. 40 depicts a synthesis of DHA-Chitosan, in accordance with embodiments of the present invention. Degree of substitution of chitosan by DHA set up as 1.5% and 23%-1H NMR.

FIG. 41 depicts, for Chitosan-SNACH-NPs (Zav=200 nm), a size distribution by intensity and a size in nanometers, in accordance with embodiments of the present invention.

Figure 42:
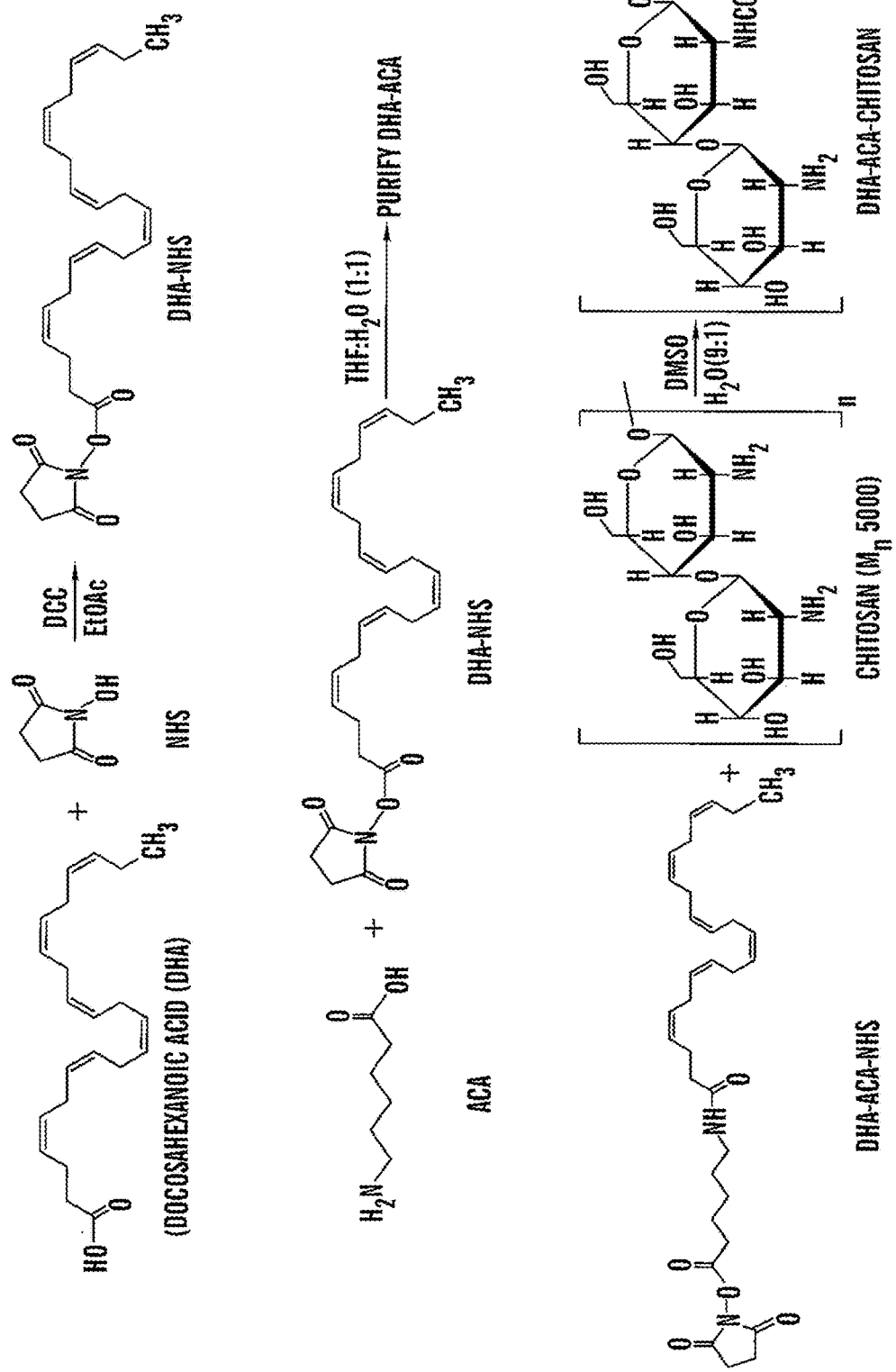
FIG. 42 depicts a synthesis of DHA conjugate of Chitosan, in accordance with embodiments of the present invention.

FIG. 42 depicts a synthesis of DHA conjugate of Chitosan, in accordance with embodiments of the present invention.

FIG. 43 depicts, for Chitosan-DHA/SNACH-NPs (Zav=248 nm), a size distribution by intensity and a size in nanometers, in accordance with embodiments of the present invention.

FIG. 44 depicts, for Chitosan-ACA-DHA/SNACH-NPs (Zav=252 nm), a size distribution by intensity and a size in nanometers, in accordance with embodiments of the present invention.

The present invention provides novel nanoparticle formulations for treatment of pancreatic cancer.

Treatments targeting the hematological complications of cancer may result in improved uptake of chemotherapeutic agents, with inhibition of tumor growth and metastasis. The inventive non-anticoagulant low molecular weight heparin (LMWH), S-NACH (1), which is devoid of bleeding side effects, increased uptake of chemotherapeutic agents into drug-resistant tumors and exhibited potent anti-tumor efficacy in two separate cancer xenograft models. S-NACH also significantly inhibited metastasis in an orthotopic pancreatic cancer model.

Clinical studies have demonstrated that LMWHs can increase survival in some clinical settings. See Karpatkin, S. and E. Pearlstein, *Role of platelets in tumor cell metastases*, Ann Intern Med, 1981, 95(5): p. 636-41. See Gasic, G. J., *Role of plasma, platelets, and endothelial cells in tumor metastasis*, Cancer Metastasis Rev, 1984, 3(2): p. 99-114. See Honn, K. V., D. G. Tang, and Y. Q. Chen, *Platelets and cancer metastasis: more than an epiphenomenon*, Semin Thromb Hemost, 1992, 18(4): p. 392-415.

However, there is an urgent need to develop and optimize novel therapies to address the unique challenges of pancreatic cancer.

Figure 45:
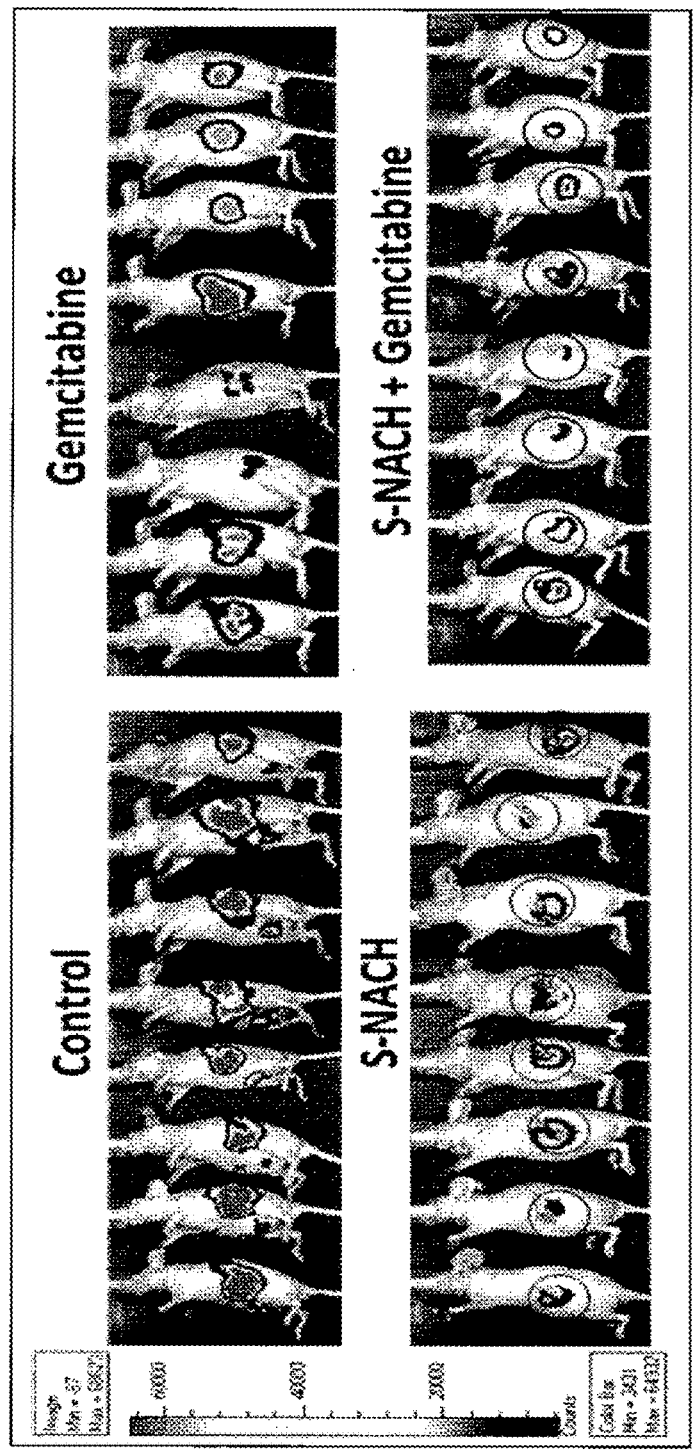
FIG. 45 depicts inhibition of pancreatic tumor growth by S-NACH and Gemcitabine (GEM) in an in vivo mouse orthotopic model, in accordance with embodiments of the present invention.

FIG. 45 depicts inhibition of pancreatic tumor growth by S-NACH and Gemcitabine (GEM) in an in vivo mouse orthotopic model, in accordance with embodiments of the present invention. Luciferase-overexpressing MPanc96-luc cells were orthotopically implanted in the pancreases of athymic nude mice. Before treatment initiation, animals were randomized by tumor mass detected using an IVIS in vivo imaging system. Living Image software was used to quantify non-saturated bioluminescence in regions of interest (ROI). The color bar to the left shows fluorescence signal intensity (red is most intense). Light emission between 5.5×10$^6$-7.0×10$^{10}$ was considered indicative of viable luciferase-labeled tumor cells, while emissions below this range were considered as background. Bioluminescence was quantified as photons/second for each ROI. In vivo tumor kinetic growth and metastasis were monitored by signal intensity. Treatments: S-NACH at 20 mg/kg s. c. daily; GEM at 100 mg/kg injected i. p. twice a week or in combination with heparins. Daily treatment of mice bearing orthotopic pancreatic tumors resulted in suppression of tumor signal intensity in S-NACH and GEM groups. Repeated administration resulted in sustained inhibition of luciferin signal strength. Tumor luminescence increased and expanded in the untreated controls, an indication of metastasis, which was confirmed either by open-cavity imaging of mice or ex vivo imaging of excised tumors from mice (not shown). Fluorescent signals were detectable when tumors were small (10-50 mg), demonstrating the sensitivity of our nanoformulations in targeting to pancreatic tumors via NP with Claudin-4 antibody conjugated to their surfaces.

The present invention provides a nanoformulation, comprising: nanoparticles, each nanoparticle comprising a shell in which a glycosaminoglycan (GAG is encapsulated, said GAG being ionically or covalently bonded to the shell, wherein the GAG is selected from the group consisting of sulfated non-anticoagulant heparin (SNACH), super-sulfated non-anticoagulant heparin (S-SNACH), and a combination thereof, and wherein the shell comprises Poly(lactic-co-glycolic acid) (PLGA), Polyethylene Glycol (PEG)-PLGA, maleimide-PEG-PLGA, chitosan, chitosan-PLGA, methoxy-polyethyleneglycol-poly(lactide-co-glycolide) (MPEG-PLGA)-(maleimide-PEG-PLGA), PLGA-Polycaprolate, or calcium alginate.

In one embodiment, the shell is positively charged, the GAG is negatively charged, and the GAG is ionically bonded to the shell.

In one embodiment, the GAG is covalently bonded to the shell.

In one embodiment, the nanoparticles are conjugated to bile acids. In one embodiment, the bile acids comprise or consist of deoxycholic acid, cholic acid, lithocholic acid, or combinations thereof.

In one embodiment, the nanoparticles are conjugated to fatty acids. In one embodiment, the fatty acids comprise or consist of eicosapentaenoic acid (EPA), docosahexaenoic acid (DHA), or a combination thereof.

In one embodiment, the nanoparticles are conjugated to Poly L-arginine.

In one embodiment, a targeted moiety is conjugated to the shell of the nanoparticle to effectuate a targeted delivery of the nanoparticle to a specified target for increasing the efficacy of a chemotherapeutic agent encapsulated within the shell of the nanoparticle.

The present invention provides a method of using the inventive nanoformulation 1 to treat a cancer in a subject. The method comprises: administering to the subject a therapeutically effective amount of the nanoformulation for treating the cancer.

In one embodiment, the cancer is selected from the group consisting of pancreatic cancer, breast cancer, liver cancer, lung cancer, bladder cancer, and combinations thereof.

In one embodiment, the shell encapsulates a chemotherapeutic agent for treating the cancer. In one embodiment, the chemotherapeutic agent includes doxorubicin, platinum, gemcitabine, or combinations thereof.

In one embodiment, a targeted moiety is conjugated to the shell of the nanoparticle to effectuate a targeted delivery of the nanoparticle to a specified target in the subject for increasing the efficacy of the chemotherapeutic agent for treating the cancer. In one embodiment, the targeted moiety is an integrin avb3 ligand and/or anti-HER2, which may be used for targeting tumors and the microenvironment of the tumors.

In one embodiment, the subject is a human being.

In one embodiment, the subject is a mammal.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A nanoformulation, comprising:
nanoparticles, each nanoparticle comprising a shell within which a glycosaminoglycan (GAG) is encapsulated, said GAG being ionically or covalently bonded to the shell, wherein the GAG is selected from the group consisting of sulfated non-anticoagulant heparin (SNACH), super-sulfated non-anticoagulant heparin (S-SNACH), and a combination thereof, and wherein the shell comprises Poly(lactic-co-glycolic acid) (PLGA), Polyethylene Glycol (PEG)-PLGA, maleimide-PEG-PLGA,chitosan, chitosan-PLGA, a blend of methoxy-polyethyleneglycol-poly(lactide-co-glycolide)(MPEG-PLGA) and maleimide-PEG-PLGA, or calcium alginate, wherein the nanoparticles are conjugated to Poly L-arginine via an amide link between the GAG and the Poly L-arginine, wherein the shell encapsulates a chemotherapeutic agent for treating cancer, and wherein a targeted moiety is conjugated to the shell of the nanoparticle to effectuate a targeted delivery of the nanoparticle to a specified target for increasing the efficacy of the chemotherapeutic agent.

2. The nanoformulation of claim 1, wherein the shell is positively charged, wherein the GAG is negatively charged, and wherein the GAG is ionically bonded to the shell.

3. The nanoformulation of claim 1, wherein the GAG is covalently bonded to the shell.

4. The nanoformulation of claim 1, wherein the GAG comprises SNACH.

5. The nanoformulation of claim 1, wherein the GAG comprises S-SNACH.

6. The nanoformulation of claim 1, wherein the shell of the nanoparticles are conjugated to bile acids.

7. The nanoformulation of claim 6, wherein the bile acids are selected from the group consisting of deoxycholic acid, cholic acid, lithocholic acid, and combinations thereof.

8. The nanoformulation of claim 1, wherein the shell of the nanoparticles are conjugated to fatty acids.

9. The nanoformulation of claim 8, wherein the fatty acids are selected from the group consisting of eicosapentaenoic acid (EPA), docosahexaenoic acid (DHA), and a combination thereof.

10. The nanoformulation of claim 1, wherein the shell comprises chitosan or chitosan-PLGA, and wherein chitosan in the shell is conjugated to Poly L-arginine.

11. The nanoformulation of claim 1, wherein the shell comprises chitosan and does not comprise chitosan-PLGA.

12. The nanoformulation of claim 1, wherein the shell comprises PEG-PLGA.

13. A method of using the nanoformulation of claim 1 to treat a cancer in a subject, said method comprising:
    administering to the subject a therapeutically effective amount of the nanoformulation of claim 1 for treating the cancer.

14. The method of claim 13, wherein the cancer is selected from the group consisting of pancreatic cancer, breast cancer, liver cancer, lung cancer, bladder cancer, and combinations thereof.

15. The method of claim 13, wherein the chemotherapeutic agent includes doxorubicin, platinum, gemcitabine, or combinations thereof.

16. The method of claim 13, wherein the targeted moiety is an integrin αvβ3 ligand and anti-HER2.

17. The method of claim 13, wherein the subject s a human being.

18. The method of claim 13, wherein the subject is a mammal.

* * * * *